United States Patent
Hutchings et al.

(10) Patent No.: US 8,900,591 B2
(45) Date of Patent: Dec. 2, 2014

(54) VACCINES COMPRISING MUTANT GPCRS WITH INCREASED CONFORMATIONAL STABILITY RELATIVE TO PARENT RECEPTORS

(75) Inventors: Catherine Jane Hutchings, Hertfordshire (GB); Malcolm Peter Weir, Hertfordshire (GB); Fiona Hamilton Marshall, Hertfordshire (GB)

(73) Assignee: Heptares Therapeutics Limited, Hertfordshire (GB)

( * ) Notice: Subject to any disclaimer, the term of this patent is extended or adjusted under 35 U.S.C. 154(b) by 0 days.

(21) Appl. No.: 13/817,858

(22) PCT Filed: Aug. 5, 2011

(86) PCT No.: PCT/GB2011/001177
§ 371 (c)(1),
(2), (4) Date: May 6, 2013

(87) PCT Pub. No.: WO2012/022928
PCT Pub. Date: Feb. 23, 2012

(65) Prior Publication Data
US 2013/0224238 A1    Aug. 29, 2013

Related U.S. Application Data

(60) Provisional application No. 61/375,626, filed on Aug. 20, 2010.

(51) Int. Cl.
| | | |
|---|---|---|
| *A61K 39/00* | (2006.01) | |
| *A61K 39/38* | (2006.01) | |
| *A61K 38/00* | (2006.01) | |
| *C07K 14/72* | (2006.01) | |
| *C07K 14/705* | (2006.01) | |

(52) U.S. Cl.
CPC ............. *A61K 39/0005* (2013.01); *A61K 38/00* (2013.01); *C07K 14/705* (2013.01)
USPC .......................... 424/184.1; 514/1.1; 514/20.6

(58) Field of Classification Search
None
See application file for complete search history.

(56) References Cited

U.S. PATENT DOCUMENTS

| | | | |
|---|---|---|---|
| 7,094,593 B1 | 8/2006 | Pausch et al. | |
| 2002/0147170 A1 | 10/2002 | Kopin et al. | |
| 2003/0232331 A1* | 12/2003 | Casman et al. | 435/6 |
| 2005/0123563 A1 | 6/2005 | Doranz et al. | |
| 2007/0154947 A1 | 7/2007 | Broach et al. | |
| 2007/0196389 A1* | 8/2007 | Caligiuri et al. | 424/229.1 |
| 2010/0190188 A1 | 7/2010 | Henderson et al. | |
| 2011/0027910 A1 | 2/2011 | Weir et al. | |
| 2011/0028700 A1 | 2/2011 | Heal | |
| 2011/0046351 A1 | 2/2011 | Weir et al. | |
| 2011/0112037 A1 | 5/2011 | Warne et al. | |
| 2012/0165507 A1 | 6/2012 | Jazayeri-Dezfuly et al. | |
| 2012/0270230 A1* | 10/2012 | Henderson et al. | 435/7.2 |

FOREIGN PATENT DOCUMENTS

| | | |
|---|---|---|
| WO | WO 2007/097820 A2 | 8/2007 |
| WO | WO 2008/114020 A2 | 9/2008 |
| WO | WO 2009/071914 A2 | 6/2009 |
| WO | WO 2009/081136 A2 | 7/2009 |

OTHER PUBLICATIONS

Flanagan CA. Molecular Pharmacology. 68(1):1-3, 2005.*
Ames et al., BacMam recombinant baculoviruses in G protein-coupled receptor drug discovery. Receptors Channels. 2004;10(3-4):99-107.
André et al., Purification of muscarinic acetylcholine receptors by affinity chromatography. EMBO J. 1983;2(4):499-504.
Andresen, A pharmacological primer of biased agonism. Endocr Metab Immune Disord Drug Targets. Jun. 2011;11(2):92-8.
Baker, A full pharmacological analysis of the three turkey β-adrenoceptors and comparison with the human β-adrenoceptors. PLoS One. Nov. 30, 2010;5(11):e15487. doi: 10.1371/journal.pone. 0015487.
Beltrame et al., Modulation of M(2) muscarinic receptor-receptor interaction by immunoglobulin G antibodies from Chagas' disease patients. Clin Exp Immunol. May 2011;164(2):170-9. doi: 10.1111/j.1365-2249.2011.04370.x. Epub Mar. 10, 2011.
Berger et al., Chemokine receptors as HIV-1 coreceptors: roles in viral entry, tropism, and disease. Annu Rev Immunol. 1999;17:657-700.
Bockaert et al., GPCR-GIP networks: a first step in the discovery of new therapeutic drugs? Curr Opin Drug Discov and Dev. 2004. 7:649-657.
Botha et al., Potential plant poisonings in dogs and cats in southern Africa. J S Afr Vet Assoc. Jun. 2009;80(2):63-74.
Bowie, Stabilizing membrane proteins. Curr. Opin. Struct. Biol. 2001. 11(4):397-402.
Calvo-Calle et al., A linear peptide containing minimal T- and B-cell epitopes of *Plasmodium falciparum* circumsporozoite protein elicits protection against transgenic sporozoite challenge. Infect Immun. Dec. 2006;74(12):6929-39. Epub Oct. 9, 2006.
Cannon et al., The KSHV G protein-coupled receptor signals via multiple pathways to induce transcription factor activation in primary effusion lymphoma cells. Oncogene. Jan. 15, 2004;23(2):514-23.
Chambers et al., High-level generation of polyclonal antibodies by genetic immunization. Nat Biotechnol. Sep. 2003;21(9):1088-92. Epub Aug. 10, 2003.
Chapple et al., Multiplexed expression and screening for recombinant protein production in mammalian cells. BMC Biotechnol. 2006. 22:6-49.
Cherezov et al., High Resolution Crystal Structure of an Engineered Human β2-Adrenergic G protein-Coupled Receptor. Science. 2007. 318(5854):1258-1265. Epub Oct. 25, 2007.
Cook et al., Persistent expression of chemokine and chemokine receptor RNAs at primary and latent sites of herpes simplex virus 1 infection. Virol J. Sep. 23, 2004;1:5.

(Continued)

*Primary Examiner* — Robert Landsman
(74) *Attorney, Agent, or Firm* — Wolf, Greenfield & Sacks, P.C.

(57) ABSTRACT

There is provided a G protein coupled receptor (GPCR) or a polynucleotide encoding said GPCR for use as a vaccine. There is also provided methods of antagonizing or agonizing a GPCR in vivo comprising the administration of a GPCR or a polynucleotide encoding a GPCR to a subject. The invention further provides a GPCR for use in inhibiting an activity of a GPCR binding partner in a subject.

7 Claims, 37 Drawing Sheets

(56) References Cited

OTHER PUBLICATIONS

Cuevas et al., M4 muscarinic receptor activation modulates calcium channel currents in rat intracardiac neurons. J Neurophysiol. Oct. 1997;78(4):1903-12.
Dance, From pond scum to pharmacy shelf. Nat Med. Feb. 2010;16(2):146-9. doi: 10.1038/nm0210-146.
Dau et al., Novel targets for antiretroviral therapy: clinical progress to date. Drugs. 2009;69(1):3150. doi: 10.2165/00003495-200969010-00003.
Degrip. Thermal Stability of Rhodopsin and Opsin in Some Novel Detergents. Methods in Enzymology. 1982. 81:256-265.
Del Giudice et al., Genetically derived toxoids for use as vaccines and adjuvants. Vaccine. Oct. 1, 1999;17 Suppl 2:S44-52.
Desmet et al., Anchor profiles of HLA-specific peptides: analysis by a novel affinity scoring method and experimental validation. Proteins. Jan. 1, 2005;58(1):53-69.
Di Paola et al., Cyclooxygenase-dependent thyroid cell proliferation induced by immunoglobulins from patients with Graves' disease. J Clin Endocrinol Metab. Feb. 1997;82(2):670-3.
Do et al., Vaccines in the management of hypertension. Expert Opin Biol Ther. Jul. 2010;10(7):1077-87. doi: 10.1517/14712598.2010.487060.
Doniger et al., Human cytomegalovirus and human herpesvirus 6 genes that transform and transactivate. Clin Microbiol Rev. Jul. 1999;12(3):367-82.
Douglas et al., Increased generation of fibrocytes in thyroid-associated ophthalmopathy. J Clin Endocrinol Metab. Jan. 2010;95(1):430-8. doi: 10.1210/jc.2009-1614. Epub Nov. 6, 2009.
Eddleston et al., Deaths due to absence of an affordable antitoxin for plant poisoning. Lancet. Sep. 27, 2003;362(9389):1041-4.
Eddleston, Applied clinical pharmacology (and public health) in rural Asia. Newsletter British Pharma Soc. Jul. 2010;3(1):13-14.
Eroglu et al., Functional reconstitution of purified metabotropic glutamate receptor expressed in the fly eye. EMBO Rep. May 2002;3(5):491-6. Epub Apr. 18, 2002.
Faham et al., Side-chain contributions to membrane protein structure and stability. J. Mol. Biol. 2004. 335:297-305.
Feng et al., Expression of CB2 cannabinoid receptor in *Pichia pastoris*. Protein Expr Purif. Dec. 2002;26(3):496-505.
Foord et al., International Union of Pharmacology. XLVI. G Protein-Coupled Receptor List. Pharmacol. Rev. 2005. 57:279-288.
Fruchart-Gaillard et al., Identification of various allosteric interaction sites on M1 muscarinic receptor using 125I-Met35-oxidized muscarinic toxin 7. Mol Pharmacol. May 2006;69(5):1641-51. Epub Jan. 26, 2006.
Fujimoto et al., Production of human antibodies to native cytokine receptors using the genetic immunization of KM mice. Hum Antibodies. 2009;18(3):75-80.
Fuller et al., Immunogenicity of hybrid DNA vaccines expressing hepatitis B core particles carrying human and simian immunodeficiency virus epitopes in mice and rhesus macaques. Virology. Aug. 1, 2007;364(2):245-55. Epub Apr. 11, 2007.
Ghochikyan et al., Prototype Alzheimer's disease epitope vaccine induced strong Th2-type anti-Abeta antibody response with Alum to Quil A adjuvant switch. Vaccine. Mar. 20, 2006;24(13):227-582. Epub Dec. 5, 2005.
Gimpl et al., Expression of the human oxytocin receptor in baculovirus-infected insect cells: high-affinity binding is induced by a cholesterol-cyclodextrin complex. Biochemistry. Oct. 24, 1995;34(42):13794-801.
Grisshamer et al. Expression of a rat neurotensin receptor in *Escherichia coli*. Biochem J. 1993. 295(2):571-576.
Grisshammer et al., Overexpression of integral membrane proteins for structural studies. Q. Rev. Biophys. 1995. 28:315-422.
Grisshammer et al., Quantitative evaluation of neurotensin receptor purification by immobilized metal affinity chromatography. Protein Expr Purif. Oct. 1997;11(1):53-60.
Guerra et al., Defining the global spatial limits of malaria transmission in 2005. Adv Parasitol. 2006;62:157-79.

Hamilton et al., Glycosylation engineering in yeast: the advent of fully humanized yeast. Curr Opin Biotechnol. Oct. 2007;18(5):387-92. Epub Oct. 24, 2007.
Hansen, Carolus: Targeting cytokines. BioCentury. Aug. 2010; A11.
Harrison et al., Protein N-glycosylation in the baculovirus-insect cell expression system and engineering of insect cells to produce "mammalianized" recombinant glycoproteins. Adv Virus Res. 2006;68:159-91.
Herrington et al., Safety and immunogenicity in man of a synthetic peptide malaria vaccine against *Plasmodium falciparum* sporozoites. Nature. Jul. 16-22, 1987;328(6127):257-9.
Herse et al., Prevalence of agonistic autoantibodies against the angiotensin II type 1 receptor and soluble fms-like tyrosine kinase 1 in a gestational age-matched case study. Hypertension. Feb. 2009;53(2):393-8. doi: 10.1161/Hypertensionaha.108.124115. Epub Dec. 8, 2008. Online Supplement.
Huang et al., A snake venom phospholipase A2 with high affinity for muscarinic acetylcholine receptors acts on guinea pig ileum. Toxicon. May 2008;51(6):1008-16. doi: 10.1016/j.toxicon.2008.01.006. Epub Jan. 17, 2008.
Huang et al., Unnatural amino acid replacement in a yeast G protein-coupled receptor in its native environment. Biochemistry. May 20, 2008;47(20):5638-48. doi: 10.1021/bi701866e. Epub Apr. 18, 2008.
Hutchings et al.,Therapeutic antibodies directed at G protein-coupled receptors. MAbs. Nov.-Dec. 2010;2(6):594-606. doi: 10.4161/mabs.2.6.13420. Epub Nov. 1, 2010.
Ingold et al., Vascular CXCR4 expression—a novel antiangiogenic target in gastric cancer? PLoS One. Apr. 8, 2010;5(4):e10087. doi: 10.1371/journal.pone.0010087.
Jaakola et al., G-protein-coupled receptor domain overexpression in *Halobacterium salinarum*: long-range transmembrane interactions in heptahelical membrane proteins. Proteins. Aug. 15, 2005;60(3):412-23.
Jaakola et al., The 2.6 Å Crystal Structure of a Human A2A Adenosine Receptor Bound to an Antagonist. Science. 2008. 322:1211-1217.
Jacobson et al., Antiviral activity of single-dose PRO 140, a CCR5 monoclonal antibody, in HIV-infected adults. J Infect Dis. Nov. 1, 2008;198(9):1345-52. doi: 10.1086/592169.
Jaenicke et al., The stability of proteins in extreme environments. Current Opinion in Structural Biology. 1998. 8:738-748.
Jahns et al., Direct evidence for a β1-adrenergic receptor-directed autoimmune attack as a cause of idiopathic dilated cardiomyopathy. J. Clinical Investigation. 2004. 113(10):1419-1429.
Jerusalinsky et al., Muscarinic toxins from the venom of *Dendroaspis* snakes with agonist-like actions. Toxicon. Apr. 1995;33(4):389-97.
Kaptein et al., Generation of polyclonal antibodies directed against G protein-coupled receptors using electroporation-aided DNA immunization. J Pharmacol Toxicol Methods. Jul.-Aug. 2008;58(1):27-31. doi: 10.1016/j.vascn.2007.11.002. Epub Dec. 3, 2007.
Kemp et al., Activating autoantibodies against the calcium-sensing receptor detected in two patients with autoimmune polyendocrine syndrome type 1. J Clin Endocrinol Metab. Dec. 2009;94(12):4749-56. doi: 10.1210/jc.2009-1080. Epub Oct. 16, 2009.
Kenakin et al., Protean agonists. Keys to active receptor states? Ann. N.Y. Acad. Sci. 1997. 812:116-125.
Kifor et al., Activating antibodies to the calcium-sensing receptor in two patients with autoimmune hypoparathyroidism. J Clin Endocrinol Metab. Feb. 2004;89(2):548-56.
Kim et al., G-CSF down-regulation of CXCR4 expression identified as a mechanism for mobilization of myeloid cells. Blood. Aug. 1, 2006;108(3):812-20. Epub Mar. 14, 2006.
Kindberg et al., A deletion in the chemokine receptor 5 (CCR5) gene is associated with tickborne encephalitis. J Infect Dis. Jan. 15, 2008;197(2):266-9. doi: 10.1086/524709.
Klammt et al., Cell-free expression as an emerging technique for the large scale production of integral membrane protein. FEBS J. Sep. 2006;273(18):4141-53. Epub Aug. 23, 2006.
Koivula et al., The three-finger toxin MTalpha is a selective alpha(2B)-adrenoceptor antagonist. Toxicon. Sep. 1, 2010;56(3):440-7. doi: 10.1016/j.toxicon.2010.05.001. Epub May 11, 2010.

(56) References Cited

OTHER PUBLICATIONS

Koo et al., Functional epitope of muscarinic type 3 receptor which interacts with autoantibodies from Sjogren's syndrome patients. Rheumatology (Oxford). Jun. 2008;47(6):828-33. doi: 10.1093/rheumatology/ken064. Epub Apr. 9, 2008.

Kovács et al., Demonstration of autoantibody binding to muscarinic acetylcholine receptors in the salivary gland in primary Sjögren's syndrome. Clin Immunol. Aug. 2008;128(2):269-76. doi: 10.1016/j.clim.2008.04.001. Epub May 27, 2008.

Krajewski et al., Site-directed mutagenesis of m1-toxin1: two amino acids responsible for stable toxin binding to M(1) muscarinic receptors. Mol Pharmacol. Oct. 2001;60(4):725-31.
Kyte et al., A Simple Method for Displaying the Hydropathic Character of a Protein. J. Mol. Biol. 1982. 157:105-132.
Lagane et al., CXCR4 dimerization and beta-arrestin-mediated signaling account for the enhanced chemotaxis to CXCL12 in WHIM syndrome. Blood. Jul. 1, 2008;112(1):34-44. doi: 10.1182/blood-2007-07-102103. Epub Apr. 24, 2008.
Lau et al., Changing single side chains can greatly enhance the resistance of a membrane protein to irreversible inactivation. J. Mol. Biol. 1999. 290:559-564.
Lembo et al., The ribonucleotide reductase R1 homolog of murine cytomegalovirus is not a functional enzyme subunit but is required for pathogenesis. J Virol. Apr. 2004;78(8):4278-88.
Li et al., Structure of Bovine Rhodopsin in a Trigonal Crystal Form. J. Mol. Biol. 2004. 343:1409-1438.
Lim et al., Genetic deficiency of chemokine receptor CCR5 is a strong risk factor for symptomatic West Nile virus infection: a meta-analysis of 4 cohorts in the US epidemic. J Infect Dis. Jan. 15, 2008;197(2):262-5. doi: 10.1086/524691.
Loudon et al., GM-CSF increases mucosal and systemic immunogenicity of an H1N1 influenza DNA vaccine administered into the epidermis of non-human primates. PLoS One. Jun. 8, 2010;5(6):e11021. doi: 10.1371/journal.pone.0011021.
Lundstrom et al., Structural genomics on membrane proteins: comparison of more than 100 GPCRs in 3 expression systems. J Struct Funct Genomics. Jun. 2006;7(2):77-91. Epub Nov. 22, 2006.
Luther et al., Alpha 1-adrenergic receptor antibodies in patients with primary hypertension. Hypertension. Feb. 1997;29(2):678-82.
Magnani et al., Co-evolving stability and conformational homogeneity of the human adenosine A2a receptor. PNAS. 2008. 105(31):10744-10749.
Makita et al., An acquired hypocalciuric hypercalcemia autoantibody induces allosteric transition among active human Ca-sensing receptor conformations. Proc Natl Acad Sci U S A. Mar. 27, 2007;104(13):5443-8. Epub Mar. 19, 2007.
Mancia et al., Expression of recombinant G-protein coupled receptors for structural biology. Mol Biosyst. Oct. 2007;3(10):723-34. Epub Sep. 7, 2007.
Marheineke et al., Lipid composition of *Spodoptera frugiperda* (Sf9) and *Trichoplusia ni* (Tn) insect cells used for baculovirus infection. FEBS Lett. Dec. 11, 1998;441(1):49-52.
Martin et al., A simple vector system to improve performance and utilisation of recombinant antibodies. BMC Biotechnology. 2006. 6:46.
Marullo et al., Human beta 2-adrenergic receptors expressed in *Escherichia coli* membranes retain their pharmacological properties. Proc Natl Acad Sci U S A. Oct. 1988;85(20):7551-5.
Mayfield et al., *Chlamydomonas reinhardtii* chloroplasts as protein factories. Curr Opin Biotechnol. Apr. 2007;18(2):126-33. Epub Feb. 20, 2007.
Mc Guire et al., Oligoclonality, impaired class switch and B-cell memory responses in WHIM syndrome. Clin Immunol. Jun. 2010;135(3):412-21. doi: 10.1016/j.clim.2010.02.006. Epub Mar. 11, 2010.
Mendis et al., The neglected burden of *Plasmodium vivax* malaria. Am J Trop Med Hyg. Jan.-Feb. 2001;64(1-2 Suppl):97-106.
Mijares et al., From agonist to antagonist: Fab fragments of an agonist-like monoclonal antibeta(2)-adrenoceptor antibody behave as antagonists. Mol Pharmacol. Aug. 2000;58(2):373-9.
Minneman et al., A Comparison of the Beta-Adrenergic Receptor of the Turkey Erythrocyte with Mammalian Beta1 and Beta2 Receptors. Mol. Pharmacol. 1980. 17:1-7.
Mor et al., Mimicking the structure of the V3 epitope bound to HIV-1 neutralizing antibodies. Biochemistry. Apr. 21, 2009;48(15):3288-303. doi: 10.1021/bi802308n.
Müller et al., Immunoglobulin adsorption in patients with idiopathic dilated cardiomyopathy. Circulation. Feb. 1, 2000;101(4):385-91.
Müller et al., Involvement of chemokine receptors in breast cancer metastasis. Nature. Mar. 1, 2001;410(6824):50-6.
Negroni et al., Immunoglobulin G from breast cancer patients in stage I stimulates muscarinic acetylcholine receptors in MCF7 cells and induces proliferation. Participation of nitric oxide synthase-derived nitric oxide. J Clin Immunol. May 2010;30(3):474-84. doi: 10.1007/s10875-010-9370-0. Epub Feb. 16, 2010.
Neubig et al., International Union of Pharmacology Committee on Receptor Nomenclature and Drug Classification. XXXVIII. Update on Terms and Symbols in Quantitative Pharmacology. Pharmacol. Rev. 2003. 55:597-606.
Niebauer et al., Characterization of monoclonal antibodies directed against the rat neurotensin receptor NTS1. J Recept Signal Transduct Res. 2006;26(5-6):395-415.
Niu et al., A novel GFP-fused eukaryotic membrane protein expression system in *Lactococcus lactis* and its application to overexpression of an Elongase. Curr Microbiol. Nov. 2008;57(5):423-8. doi: 10.1007/s00284-008-9223-8. Epub Sep. 4, 2008.
Olson et al., CCR5 monoclonal antibodies for HIV-1 therapy. Curr Opin HIV AIDS. Mar. 2009;4(2):104-11. doi: 10.1097/COH.0b013e3283224015.
Overington et al., How many drug targets are there? Natur Rev. Drug Discovery. 2006. 5:993-996.
Palczewski et al., Crystal Structure of Rhodopsin: A G Protein-Coupled Receptor. Science. 2000. 289:739-745.
Pallais et al., Acquired hypocalciuric hypercalcemia due to autoantibodies against the calcium-sensing receptor. N Engl J Med. Jul. 22, 2004;351(4):362-9.
Parker et al., Truncation of the Extended Carboxyl-terminal Domain Increases the Expression and Regulatory Activity of the Avian,& Adrenergic Receptor. J. Biol. Chem. 1991. 266:9987-9996.
Parker et al., Carboxyl terminal domains in the avian β1-adrenergic receptor that regulate agonist-promoted endocytosis. J. Biol. Chem. 1995. 270:6482-6487. Erratum in: J Biol Chem 1995. 270(17):10358.
Parker et al., Reconstitutively Active G Protein-coupled Receptors Purified from Baculovirus-infected Insect Cells. J. Biol. Chem. 1991. 266:519-527.
Patenge et al., Extensive proteolysis inhibits high-level production of eukaryal G protein-coupled receptors in the archaeon *Haloferax volcanii*. FEMS Microbiol Lett. Feb. 1, 1999;171(1):27-35.
Paulsen et al., Epstein-Barr virus-encoded BILF1 is a constitutively active G protein-coupled receptor. J Virol. Jan. 2005;79(1):536-46.
Potter, Snake toxins that bind specifically to individual subtypes of muscarinic receptors. Life Sci. Apr. 27, 2001;68(22-23):2541-7.
Prabhakar et al., Current perspective on the pathogenesis of Graves' disease and ophthalmopathy. Endocr Rev. Dec. 2003;24(6):802-35.
Rajagopalan et al., Beta-cardiotoxin: a new three-finger toxin from *Ophiophagus hannah* (king cobra) venom with beta-blocker activity. Faseb J. Nov. 2007;21(13):3685-95. Epub Jul. 6, 2007.
Rasmussen et al., Crystal structure of the human β2 adrenergic g-protein-coupled receptor. Nature. 2007. 450:383-387.
Reeves et al., Structure and function in rhodopsin: a tetracycline-inducible system in stable mammalian cell lines for high-level expression of opsin mutants. Proc Natl Acad Sci U S A. Oct. 15, 2002;99(21):13413-8. Epub Oct. 7, 2002.
Ribeiro et al., A vaccine encoding conserved promiscuous HIV CD4 epitopes induces broad T cell responses in mice transgenic to multiple common HLA class II molecules. PLoS One. Jun. 11, 2010;5(6):e11072. doi: 10.1371/journal.pone.0011072.
Roberts et al., Clinical safety and efficacy of a powdered Hepatitis B nucleic acid vaccine delivered to the epidermis by a commercial prototype device. Vaccine. Sep. 23, 2005;23(40):4867-78.

(56) References Cited

OTHER PUBLICATIONS

Robertson et al., The properties of thermostabilized G protein-coupled receptors (StaRs) and their use in drug discovery. Neuropharmacology 60: 36-44, 2011.

Rosenbaum et al., GPCR Engineering Yields High-Resolution Structural Insights into b2-Adrenergic Receptor Function. Science. 2007. 318:1266-1273.

Roy et al., Employing Rhodobacter sphaeroides to functionally express and purify human G protein-coupled receptors. Biol Chem. Jan. 2008;389(1):69-78.

Samson et al., Resistance to HIV-1 infection in caucasian individuals bearing mutant alleles of the CCR-5 chemokine receptor gene. Nature. Aug. 22, 1996;382(6593):722-5.

Sander et al., Expression of the human D2S dopamine receptor in the yeasts *Saccharomyces cerevisiae* and *Schizosaccharomyces pombe*: a comparative study. FEBS Lett. May 9, 1994;344(1):41-6.

Schaffner et al., A Rapid, Sensitive, and Specific Method for the Determination of Protein in Dilute Solution. Anal. Biochem. 1973. 56:502-514.

Schofield et al., Application of phage display to high throughput antibody generation and characterization. Genome Biology. 2007. 8(11):R254.

Serrano-Vega et al., Conformational thermostabilisation of the β1-adrenergic receptor in a detergent-resistant form. PNAS. 2008 105(3):877-882.

Sheng et al., In vivo adsorption of autoantibodies in myasthenia gravis using Nanodisc-incorporated acetylcholine receptor. Exp Neurol. Oct. 2010;225(2):320-7. doi: 10.1016/j.expneurol.2010.07.003. Epub Jul. 15, 2010.

Shibata et al. Thermostabilization of the Neurotensin Receptor NTS1, J. Mol. Biol. 2009 390(2):262-277.

Sinclair et al., Kinetics of digoxin and anti-digoxin antibody fragments during treatment of digoxin toxicity. Br J Clin Pharmacol. Sep. 1989;28(3):352-6.

Smit et al., Virally encoded G protein-coupled receptors: targets for potentially innovative anti-viral drug development. Curr Drug Targets. Jul. 2003;4(5):431-41.

Smulski et al., Structural basis of the cross-reaction between an antibody to the *Trypanosoma cruzi* ribosomal P2beta protein and the human beta1 adrenergic receptor. Faseb J. Jul. 2006;20(9):1396-406.

Staudt et al., Immunoadsorption in dilated cardiomyopathy: 6-month results from a randomized study. Am Heart J. Oct. 2006;152(4):712. e1-6.

Straub et al., Expression cloning of a cDNA encoding the mouse pituitary thyrotropin-releasing hormone receptor. Proc Natl Acad Sci U S A. Dec. 1990;87(24):9514-8.

Surman et al., Generation of polyclonal rabbit antisera to mouse melanoma associated antigens using gene gun immunization. J Immunol Methods. May 1, 1998;214(1-2):51-62.

Tan et al., FGF and stress regulate CREB and ATF-1 via a pathway involving p38 MAP kinase and MAPKAP kinase-2. EMBO J. 1996. 15(17):4629-4642.

Tate. Overexpression of mammalian integral membrane proteins for structural studies. FEBS Lett. 2001. 504:94-98.

Tate. Baculovirus-Mediated Expression of Neurotransmitter Transporters. Methods Enzymol. 1998. 296:443-455.

Tateno et al., Production and characterization of the recombinant human mu-opioid receptor from transgenic silkworms. J Biochem. Jan. 2009;145(1):37-42. doi: 10.1093/jb/mvn147. Epub Nov. 4, 2008.

Thompson et al., Clustal W: improving the sensitivity of progressive multiple sequence alignment through sequence weighting, position-specific gap penalties and weight matrix choice Nucl. Acids Res. 1994. 22:4673-4680.

Tournamille et al., Disruption of a GATA motif in the Duffy gene promoter abolishes erythroid gene expression in Duffy-negative individuals. Nat Genet. Jun. 1995;10(2):224-8.

Tsutsumi et al., Inhibitors of the Chemokine Receptor CXCR4: Chemotherapy of AIDS, Metastatic Cancer, Leukemia and Rheumatoid Arthritis. Letters Drug Design Discovery. 2007;4(1):20-26.

Tucker et al., Purification of a rat neurotensin receptor expressed in *Escherichia coli*. Biochem. J. 1996. 317(Pt. 3):891-899.

Wallukat et al., Specific removal of beta1-adrenergic autoantibodies from patients with idiopathic dilated cardiomyopathy. N Engl J Med. Nov. 28, 2002;347(22):1806.

Warne et al., Structure of a β1-adrenergic G protein-coupled receptor. Nature. 2008. 454:486-491.

Warne et al., Expression and purification of truncated, non-glycosylated turkey beta-adrenergic receptors for crystallization. Biochim. Biophys. Acta. 2003. 1610:133-140.

Weiss et al., Purification and characterization of the human adenosine A2a receptor functionally expressed in *Escherichia coli*. Eur. J. Biochem. 2002. 269:82-92.

Wenzel et al., Potential relevance of alpha(1)-adrenergic receptor autoantibodies in refractory hypertension. PLoS One. 2008;3(11):e3742. doi: 10.1371/journal.pone.0003742. Epub Nov. 17, 2008.

White, The progress of membrane protein structure determination. Protein Science. 2004. 13:1948-1949.

Yager et al., Prospects for developing an effective particle-mediated DNA vaccine against influenza. Expert Rev Vaccines. Sep. 2009;8(9):1205-20. doi: 10.1586/erv.09.82.

Yarden et al., The avian beta-adrenergic receptor: Primary structure and membrane topology. Proc. Natl. Acad. Sci. USA. 1986. 83:6795-6799.

Zhou et al., Angiotensin receptor agonistic autoantibody-mediated tumor necrosis factor-alpha induction contributes to increased soluble endoglin production in preeclampsia. Circulation. Jan. 26, 2010;121(3):436-44. doi: 10.1161/CIRCULATIONAHA.109.902890. Epub Jan. 11, 2010.

Zhou et al., Building a Thermostable Membrane Protein. J. Biol. Chem. 2000. 275:6975-6979.

Alberts et al., Solubilizing membrane proteins with a mild detergent. Molecular Biology of the Cell. 2002;4th Edition. New York: Garland Science. Figure 10-24.

Hulme et al., Phenotypic classification of mutants: a tool for understanding ligand binding and activation of muscarinic acetylcholine receptors. Biochem Soc Trans. Aug. 2007;35(Pt 4):742-5.

Schimerlik, Overview of membrane protein solubilization. Current Protocols in Neuroscience 2001;5.9.1-5.9.5. Abstract.

\* cited by examiner

Figure 1A
Alignment of the turkey β-adrenergic receptor with human β1, β2 and β3

```
adrb1_melga    1            MGDGWLPPDCGPHNRSGGGGATAAPTGSR----------------  29
adrb1_human    1 MGAGVLVLGASE------PGNLSSAAPLPDGAATAARLLVPASPPASLLP  44
adrb2_human    1        MGQ---------PGNGSAFLLAPNRSHAPD----------------  21
adrb3_human    1       MAPW-------PHENSSLAPWPDLPTLAP-------------N     23
                          *   *
                                                            a
adrb1_melga   30 -QVSAEL-LSQQWEAGMSLLMALVVLLIVAGNVLVIAAIGTQRLQTLTN   77
adrb1_human   45 PASESPEPLSQQWTAGMGLLMALIVLLIVAGNVLVIVAIAKTPRLQTLTN   94
adrb2_human   22 -HDVTQQ-RDEVWVVGMGIVMSLIVLAIVFGNVLVITAIAKFERLQTVTN   69
adrb3_human   24 TANTSGLPGVPWEAALAGALLALAVLATVGGNLLVIVAIAWTPRLQTMTN   73
                                                            bc
adrb1_melga   78 LFITSLACADLVMGLLVVPFGATLVVRGTWLWGSFLCECWTSLDVLCVTA  127
adrb1_human   95 LFIMSLASADLVMGLLVVPFGATIVVWGRWEYGSFFCELWTSVDVLCVTA  144
adrb2_human   70 YFITSLACADLVMGLAVVPFGAAHILMKMWTFGNFWCEFWTSIDVLCVTA  119
adrb3_human   74 VFVTSLAAADLVMGLLVVPPAATLALTGHWPLGATGCELWTSVDVLCVTA  123
                           d                e
adrb1_melga  128 SIETLCVIAIDRYLAITSPFRYQSLMTRARAKVIICTVWAISALVSFLPI  177
adrb1_human  145 SIETLCVIALDRYLAITSPFRYQSLLTRARARGLVCTVWAISALVSFLPI  194
adrb2_human  120 SIETLCVIAVDRYFAITSPFKYQSLLTKNKARVIILMVWIVSGLTSFLPI  169
adrb3_human  124 SIETLCALAVDRYLAVTNPLRYGALVTKRCARTAVVLVWVVSAAVSFAPI  173
                                                                     f
adrb1_melga  178 MMHWWRDEDP-QALKCYQDPGCCDFVTNRAYAIASSIISFYIPLLIMIFV  226
adrb1_human  195 LMHWWRAESD-EARRCYNDPKCCDFVTNRAYAIASSVVSFYVPLCIMAFV  243
adrb2_human  170 QMHWYRATHQ-EAINCYANETCCDFFTNQAYAIASSIVSFYVPLVIMVFV  218
adrb3_human  174 MSQWWRVGADAEAQRCHSNPRCCAFASNMPYVLLSSSVSFYLPLLVMLFV  223
                                                           g
adrb1_melga  227 LLRWYREAKEQIRKIDRCEGRFYGSQE-----QPQ---PPPLPQHQPILG- 268
adrb1_human  244 YLRVFREAQKQVKKIDSCERRFLGGPARPPSPSPSPVPAPAPPPGPPRPA  293
adrb2_human  219 YSRVFQEAKRQLQKIDKSEGRFHVQN--------------LSQVEQDGR-  253
adrb3_human  224 YARVFVVATRQLRLLRGELGRFPPEES-PPAPSRSLAPAPVGTCAPPE--  270
                                                       h
adrb1_melga  269 ---------NGRASKRKTSRVMAMREHKALKTLGIIMGVFTLCWLPFFLV  309
adrb1_human  294 AAAATAPLANGRAGKRRPSRLVALREQKALKTLGIIMGVFTLCWLPFFLA  343
adrb2_human  254 ---------TGHGLRR--SSKFCLKEHKALKTLGIIMGTFTLCWLPFFIV  292
adrb3_human  271 --------GVPACGRRPARLLPLREHRALCTLGLIMGTFTLCWLPFFLA  311
                        i    j   k  l
adrb1_melga  310 NIVNVFNR-DLVPDWLFVFFNWLGYANSAMNPIIYCRSPDFRKAFKRLLC  358
adrb1_human  344 NVVKAFHR-ELVPDRLFVFFNWLGYANSAFNPIIYCRSPDFRKAFQRLLC  392
adrb2_human  293 NIVHVIQD-NLIRKEVYILLNWIGYVNSGFNPLIYCRSPDFRIAFQELLC  341
adrb3_human  312 NVLRALGGPSLVPGPAFLALNWLGYANSAFNPLIYCRSPDFRSAFRRLLC  361
```

Figure 1B

```
adrb1_melga  359 FPRKADRRLHAGGQPAPLPGGFISTLGSPEHSPGGTWSDCNGGTRGGSES 408
adrb1_human  393 CARRAARRRHATHGDRPR---------------ASGCLARPGPPPS 423
adrb2_human  342 LRRSSLKAYGNG-----------------YS------SNGNTGEQSG--- 365
adrb3_human  362 RCGRRLP-------PEP---------------------CAAARPALFPS 382 adrb1_melga  409 SLEERHSKTSRSESKMEREKNILATTRFYCTFLGNGDKAVFCTVLRIVKL 458
adrb1_human  424 PGAASDDDD--------DDVVGATPPARLLEPWAGCNGGAAADSDSSLDE 465
adrb2_human  366 ----YHVEQ------EKENK-------LLCEDLPGTEDFVGHQGTVPSDN 398
adrb3_human  383 GVPAARS----------------SPAQPRLCQRLDGASWGVS         408 adrb1_melga  459 FEDATCTCPHTHKLKMKWRFKQHQA 483
adrb1_human  466 PCRPGFASESKV             477
adrb2_human  399 IDSQGRNCSTNDSLL          413
adrb3_human  409                          408
```

SEE BELOW FOR KEY

■ Position of mutations in m23
▲ Position of other thermostabilising mutations
▨ Position of transmembrane domains
▩ Position of helix 8

Where other amino acid substitutions gave significant thermostability, the position is labelled with a lower case letter and the mutations are listed below in order of decreasing thermostability.

a. R68S
b. V89L
c. M90V, A
d. I129V, A, G
e. S151E, Q
f. L221V, I
g. R229Q, A
h. A282L, V, Q
i. D322A, P
j. F327A, G, M, V
k. A334L, S, I
l. F338M, A, V, I

Figure 2A
Alignment of human adenosine receptors

```
AA2AR_human    1            MPIMGSSVYITVELAIAVLAILGNVLVCWAVWLNSNLQNVTNYF  44
AA2BR_human    1            MLLETQDALYVALELVIAALSVAGNVLVCAAVGTANTLQTPTNYF 45
AA3R_human     1  MPNNSTALSLANVTYITMEIFIGLCAIVGNVLVICVVKLNPSLQTTTFYF 50
AA1R_human     1  MP---PSISAFQAAYIGIEVLIALVSVPGNVLVIWAVRVNQALRDATFCF 47

AA2AR_human    45 VVSLAAADIAVGVLAIPFAITISTGFCAACHGCLFIACFVLVLTQSSIFS  94
AA2BR_human    46 LVSLAAADVAVGLFAIPFAITISLGFCTDFYGCLFLACFVLVLTQSSIFS  95
AA3R_human     51 IVSLALADIAVGVLVMPLAIVVSLGITIHFYSCLFMTCLLLIFTHASIMS 100
AA1R_human     48 IVSLAVADVAVGALVIPLAILINIGPQTYFHTCLMVACPVLILTQSSILA  97

AA2AR_human    95 LLAIAIDRYIAIRIPLRYNGLVTGTRAKGIIAICWVLSFAIGLTPMLGWN 144
AA2BR_human    96 LLAVAVDRYLAICVPLRYKSLVTGTRARGVIAVLWVLAFGIGLTPFLGWN 145
AA3R_human    101 LLAIAVDRYLRVKLTVRYKRVTTHRRIWLALGLCWLVSFLVGLTPMFGWN 150
AA1R_human     98 LLAIAVDRYLRVKIPLRYKMVVTPRRAAVAIAGCWILSFVVGLTPMFGWN 147

AA2AR_human   145 -------NCGQPKEGKNHSQGCGEGQVACLFEDVVPMNYMVYFNFFACVL 187
AA2BR_human   146 SKDSATNNCTEPWDGTTNESCC---LVKCLFENVVPMSYMVYFNFFGCVL 192
AA3R_human    151 -------MKLTSEYHRNVT------FLSCQFVSVMRMDYMVYFSFLTWIF 187
AA1R_human    148 -------NLSAVERAWAANGSMGEPVIKCEFEKVISMEYMVYFNFFVWVL 190

AA2AR_human   188 VPLLLMLGVYLRIFLAARRQLKQMESQPLPGERARSTLQKEVHAAKSLAI 237
AA2BR_human   193 PPLLIMLVIYIKIFLVACRQLQRTELMDHS----RTTLQREIHAAKSLAM 238
AA3R_human    188 IPLVVMCAIYLDIFYIIRNKLSLNLSNSK---ETGAFYGREFKTAKSLFL 234
AA1R_human    191 PPLLLMVLIYLEVFYLIRKQLNKKVSASSG--DPQKYYGKELKIAKSLAL 238
```

Figure 2B

```
AA2AR_human  238 IWGLFALCWLPHIINCFTFFCPDCS-HAPLWLMYLAIVLSHTNSVVNPF 286
AA2BR_human  239 IVGIFALCWLPVHAVNCVTLFQPAQGKNKPKWAMNMAILLSHANSVVNPI 288
AA3R_human   235 VLFLFALSWLPLSIINCIIYFNG----EVPQLVLYMGILLSHANSMMNPI 280
AA1R_human   239 ILFLFALSWLPLHILNCITLFCPSC--HKPSILTYIAIFLTHGNSAMNPI 286

AA2AR_human  287 IYAYRIREFRQTFRKIIRSHVLRQQEPFKAAGTSARVLAAHGSDGEQVSL 336
AA2BR_human  289 VYAYRNRDFRYTFHKIISRYLLCQ----------ADVKSGNGQAGVQPAL 328
AA3R_human   281 VYAYKIKKFKETYLLILKACVVCHP----------SDSLDTSIEKNSE   318
AA1R_human   287 VYAFRIQKFRVTFLKIWNDHFRCQP----------APPIDEDLPEERPDD 326

AA2AR_human  337 RLNGHPPGVWANGSAPHPERRPNGYALGLVSGGSAQESQGNTGLPDVELL 386
AA2BR_human  329 GVGL                                               332
AA3R_human   319                                                    318
AA1R_human   327                                                    326

AA2AR_human  387 SHELKGVCPEPPGLDDPLAQDGAGVS 412
AA2BR_human  333                            332
AA3R_human   319                            318
AA1R_human   327                            326
```

A    Mutations determined by agonist binding
     Mutations determined by antagonist binding
     Position of transmembrane domains
     Position of helix 8

Figure 3A
Alignment of neurotensin receptors

```
NTR1_rat    1   MHLNSSVPQGTPGEPDAQPFSGPQSEMEATFLALSLSNGSGNTSESDTAG   50
NTR1_human  1   MRLNSSAP-GTPGTPAADPFQRAQAGLEEALLAPGFGNASGNASERVLAA   49
NTR2_human  1        METSSP--RPPRPSSNPG---------------------------LS   18
                 . .*  *      *   *  .  *

NTR1_rat    51  PNSDLDVNTDIYSKVLVTAIYLALFVVGTVGNSVTAFTLARKKSLQSLQS  100
NTR1_human  50  PSSELDVNTDIYSKVLVTAVYLALFVVGTVGNTVTAFTLARKKSLQSLQS   99
NTR2_human  19  LDARLGVDTRLWAKVLFTALYALIWALGAAGNALSVHVVLKAR--AGRAG   66
                  . *  *       ********************************  .

NTR1_rat    101 TVRYHLGSLALSDLLILLLAMPVELYNFIWVHHPWAFGDAGCRGYYFLRD  150
NTR1_human  100 TVHYHLGSLALSDLLTLLLAMPVELYNFIWVHHPWAFGDAGCRGYYFLRD  149
NTR2_human  67  RLRHHVLSLALAGLLLLLVGVPVELYSFVWFHYPWVFGDLGCRGYYFVHE  116
                ***************************. * * **  ************

NTR1_rat    151 ACTYATALNVASLSVERYLAICHPFKAKTLMSRSRTKKFISAIWLASALL  200
NTR1_human  150 ACTYATALNVASLSVERYLAICHPFKAKTLMSRSRTKKFISAIWLASALL  199
NTR2_human  117 LCAYATVLSVAGLSAERCLAVCQPLRARSLLTPRRTRWLVALSWAASIGL  166
                 ***** *  * ** ** ** ** . .* . *. ***************

NTR1_rat    201 AIPMLFTMGLQNR--SGDG-THPGGLVCTPIVDTATVKVVIQVNTFMSPL  247
NTR1_human  200 AVPMLFTMGEQNR--SADG-QHAGGLVCTPTIHTATVKVVIQVNTFMSFI  246
NTR2_human  167 ALPMAVIMGQKHELETADGEPEPASRVCTVLVSRTALQVFIQVNVLVSFV  216
                * **    * *     * *   * **   * .** ******* *** .

NTR1_rat    248 FPMLVISILNTVCANKLTVMVHQAAEQ---G-----RVCEVGTHNGLEHS  289
NTR1_human  247 FPMVVISVLNTIIANKLTVMVRQAAEQ---G-----QVCTVGG----EHS  284
NTR2_human  217 LPLALTAFLNGVTVSHLLALCSQVPSTSTPGSSTPSRLELLSEEGLLSFI  266
                 *          *  . . *    *    *            *
```

Figure 3B

```
NTR1_rat    290 TFNMPIE------------PGRVQALRHGVLVLRAVVIAFVVCWLPYHVR 327
NTR1_human  285 TFSMAIE------------PGRVQALRHGVRVLRAVVIAFVVCWLPYHVR 322
NTR2_human  267 VWKKTFIQGGQVSLVRHKDVRRIRSLQRSVQVLRAIVVMYVICWLPYHAR 316

NTR1_rat    328 RLMFCYISDEQWTTFLFDFYHYFYMLTNALFYVSSAINPILYNLVSANFR 377
NTR1_human  323 RLMFCYISDEQWTPFLYDFYHYFYMVTNALFYVSSTINPILYNLVSANFR 372
NTR2_human  317 RLMYCYVPDDAWTDPLYNFYHYFYMVTNTLFYVSSAVTPLLYNAVSSSFR 366

NTR1_rat    378 QVFLSTLACLCPGWRHRKKKRPTFSRKPNSMSSNHAFSTSATRETLY    424
NTR1_human  373 HIFLATLACLCPVWRRRRK-RPAFSRKADSVSSNHTLSSNATRETLY    418
NTR2_human  367 KLFLEAVSSLC-GEHHPMKRLPPKPQSPTLMDTASGFGD--PPETR    409
```

A    Mutations determined by heating in the absence of neurotensin
     Mutations determined by heating in the presence of neurotensin
€    Mutations that significantly improve expression levels in E. coli
     Position of transmembrane domains
     Position of helix 8

(a) H103: Thermostability obtained with A, N, S, V, L, M
       Only H103N and H103S gave wt levels of expression

```
adrB2_human  280  GTVTCTIT---PFFTVTTVHVTQD---------------------NLIRKEVYILLNWIGYVNSGFNPLIYCRS  332
NTR1_rat     315  IAFVVCWLPYHVRRIMFCYISDEQW---------------------PLFDFYHYFYMLTNALFYVSSAINPILYNLV  387
muscM1_human 372  LAFILTWTPYNIMVLVSTFCKD---------------------CVPETIWELGYWLCYVNSTINPMCYALC  442
adrB1_melga  297  GVFTLCWLPFFLVNIVNVFNR---------------------DLVPDWLFVFFNWIGYANSAFNPIIYCRS  344
ADORA2A      240  GLFALCWLPLHIINCFTFFCPD---------------------CSHAPLWLMYLAIVLSHTNSVVNPFIYAYR  329 adrB2_human  329  -PDFRIAFQELLCLRRSS---------------LKAYGNGYSSNGNTGEQSGYHVEQE----------  372
NTR1_rat     373  SANFRQVFLSTLACLCPVWRHRRKK---------RPTFRKPMQVSSMHAFSTSA-----------  419
muscM1_human 422  NKAFRDTFRLLLLCRWDKRRWRKIPKRPGS---VHRTPSRQC---------------------------  460
adrB1_melga  346  -PDFRKAFKRLLCFPRKADRRLHAGGQPAPLPGGFISTLGSPEHSPGGTWSDCNGGTRGG---------  406
ADORA2A      292  IREFRQTFRKIIRSHVLRQQEPFKAAGTSARVLAAHGSDGEQVSLRLNGHPPGVWANGSA---------  352 adrB2_human  372  KENKLLCEDLPGTEDFVGHQGTVP---------------SDNIDSQGRNCSTNDSLL---------  413
NTR1_rat     419  TRETLY-----------------------------------------------------------  424
muscM1_human 460  ------------------------------------------------------------------  460
adrB1_melga  406  SESSLEERHSKTSRSESKMEREKNILATTLATTRFYCTPLGNDKAVFCTVIRIVLPEDATCT---------  466
ADORA2A      352  PHPERRPNGYALGLVSGGSAQESQGNTGLPDVELLSHELKGVCPEPPGLDDPLAQDGAGV---------  412 adrB2_human  413  ----------------------------------------  413
NTR1_rat     424  ----------------------------------------  424
muscM1_human 460  ----------------------------------------  460
adrB1_melga  466  CPHHLSIKMKMEFKQHQA---------------------  483
ADORA2A      412  Q---------------------------------------  412
```

Figure 6A
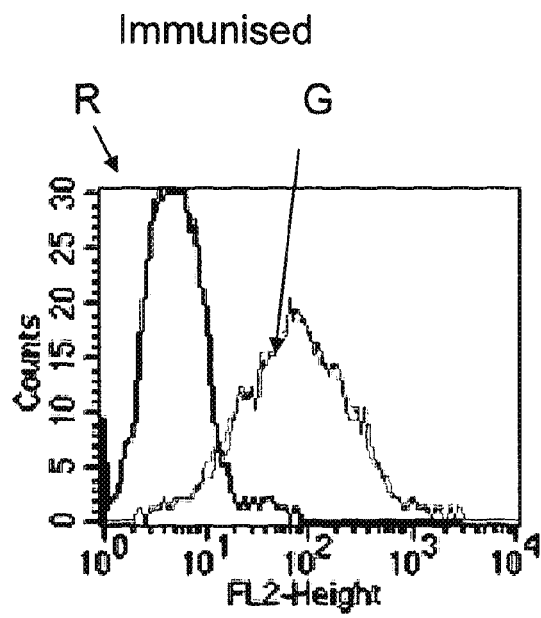
mouse 1
dilution 1:1000
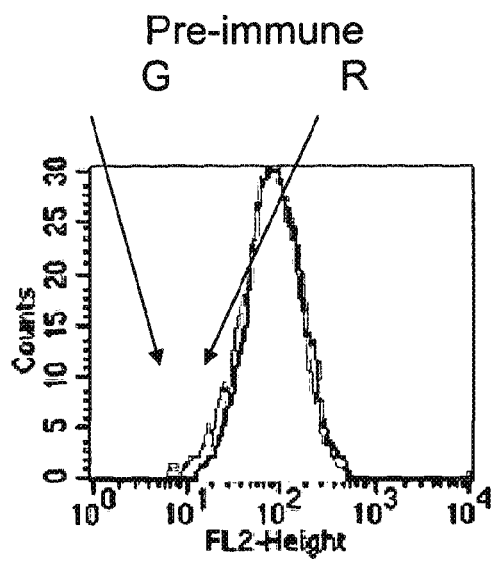
mouse 1
dilution 1:1000

Figure 6B
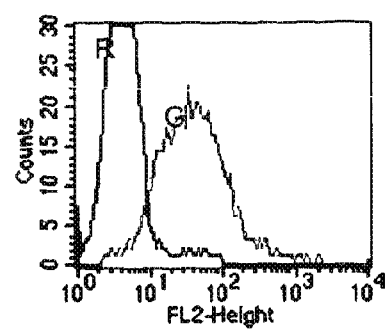
mouse 2
dilution 1:1000
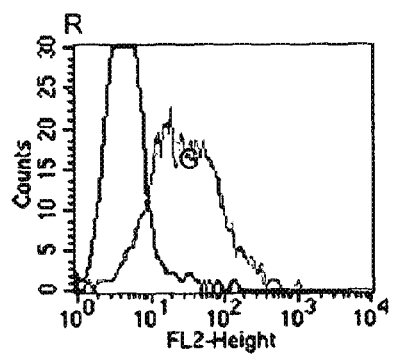
mouse 4
dilution 1:1000
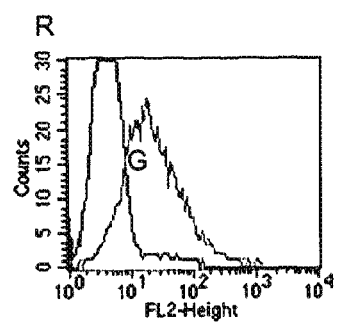
mouse 5
dilution 1:1000

Figure 7
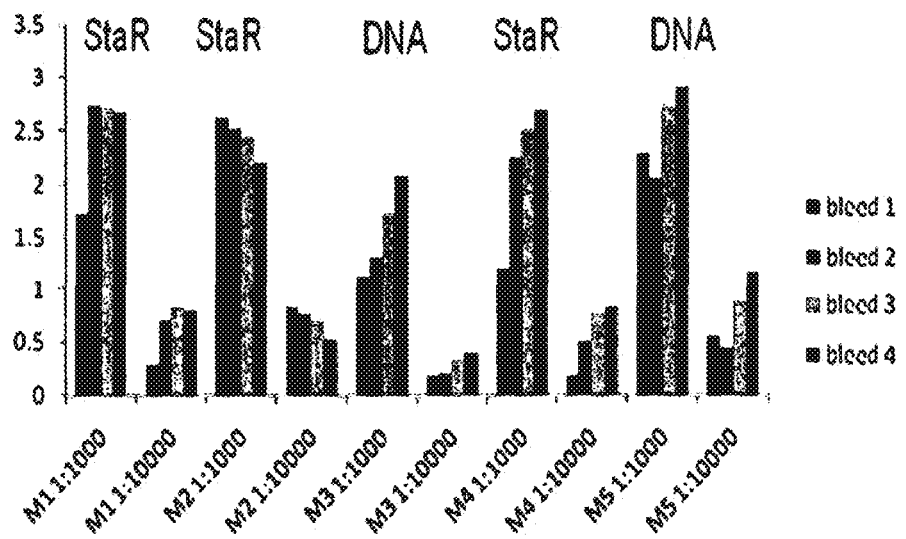
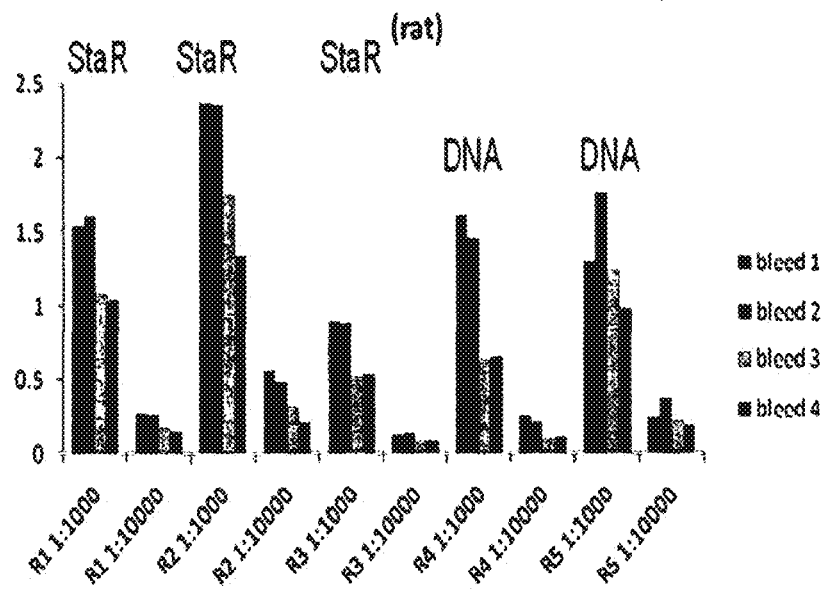

A. Controls – detection of N terminally HA-tagged WT and StaR

B. Mouse sera – native conditions

C. Rat sera – native conditions

Figure 9A
A. Comparison of sera MFI in mouse and rat
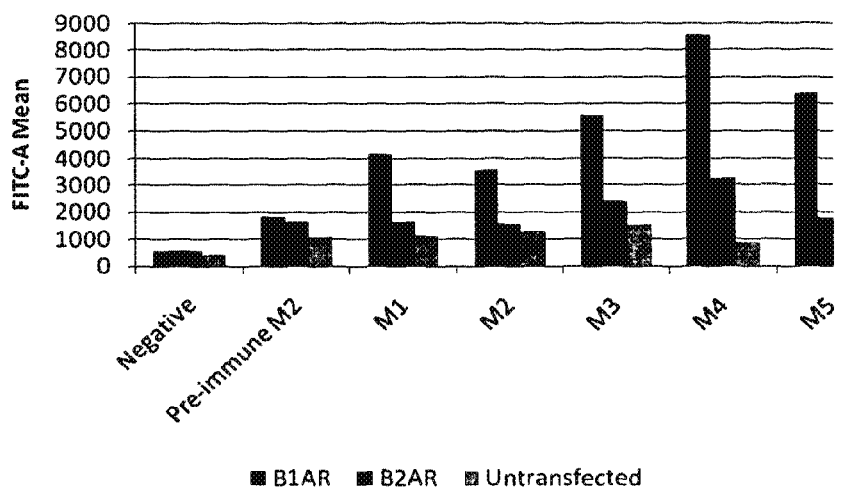
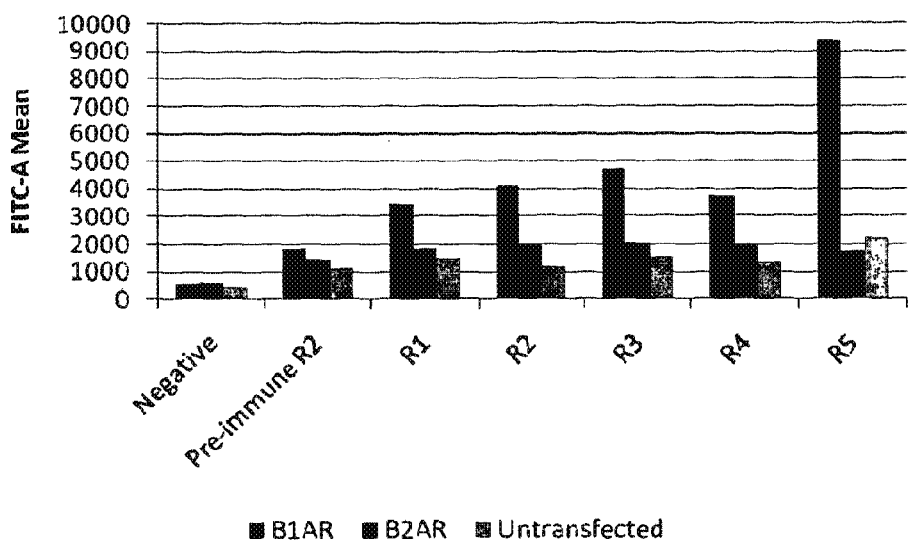

Figure 9B
B. Histogram profiles
Mouse 4
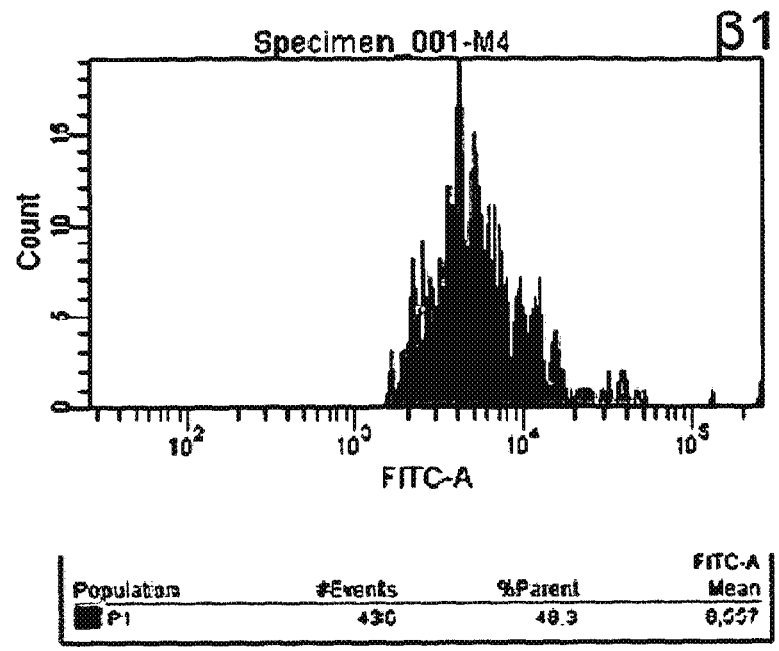
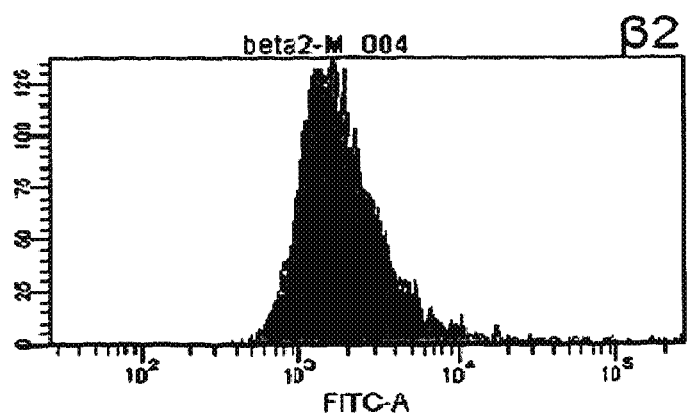

A. Mice immunised with StaR cDNA

Figure 11B
B. Mice immunised with WT receptor
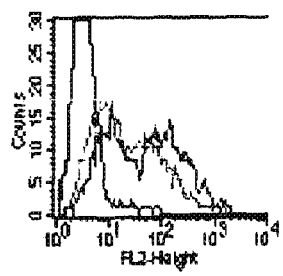
mouse 1
dilution 1:1000
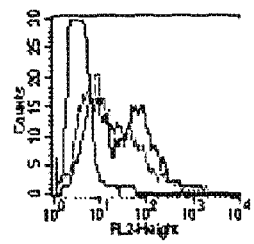
mouse 2
dilution 1:1000
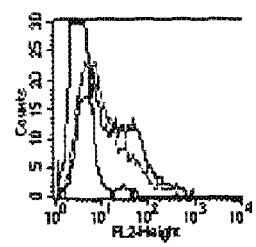
mouse 3
dilution 1:1000
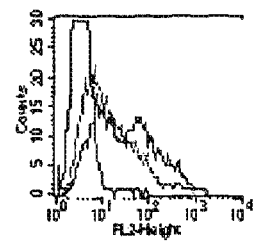
mouse 4
dilution 1:1000

Figure 16
Rat – DNA+protein: greater immune response observed than first study
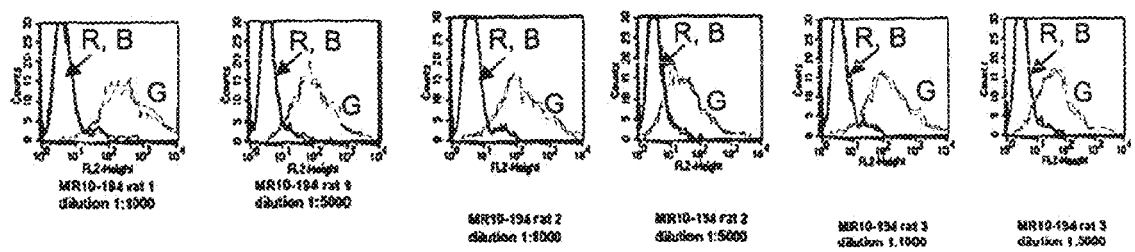
Mouse – DNA+protein: robust immune response
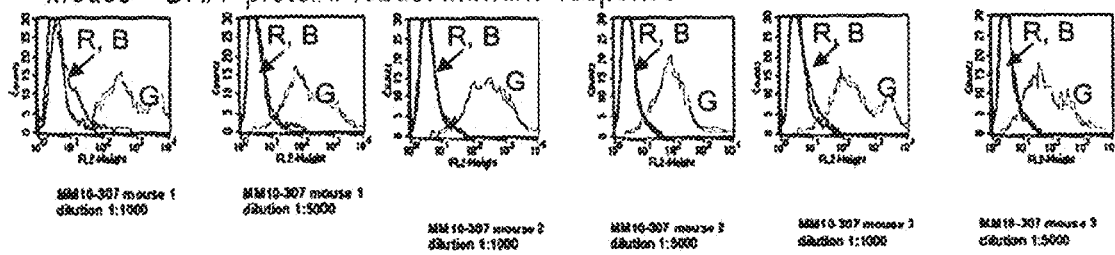
Green Interim bleed on cells transfected with β1AR
Red Interim bleed on cells transfected with irrelevant cDNA
Blue Pre-immune bleed on cells transfected with β1AR

Figure 17
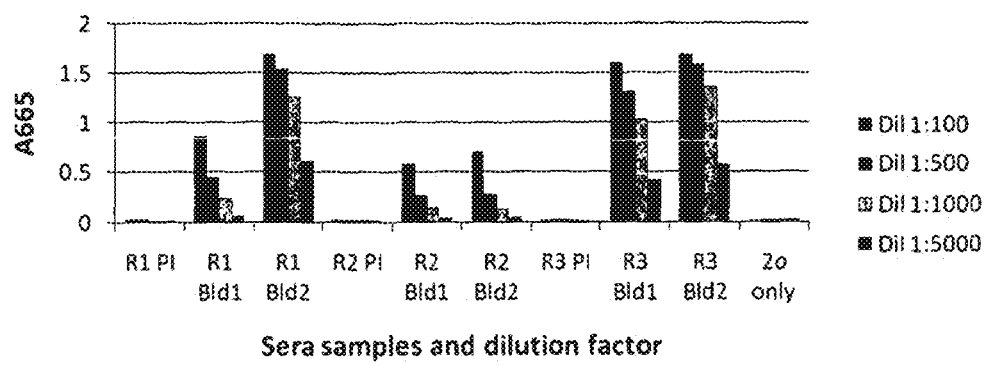
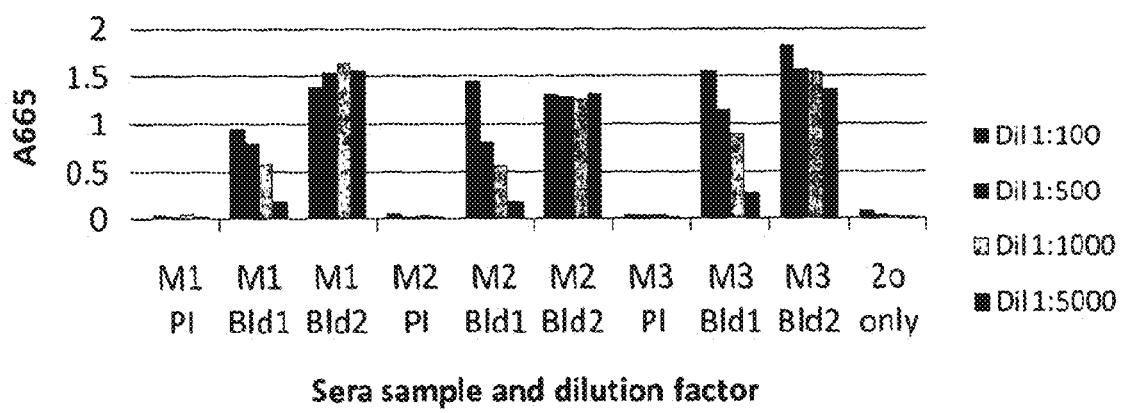

Figure 19
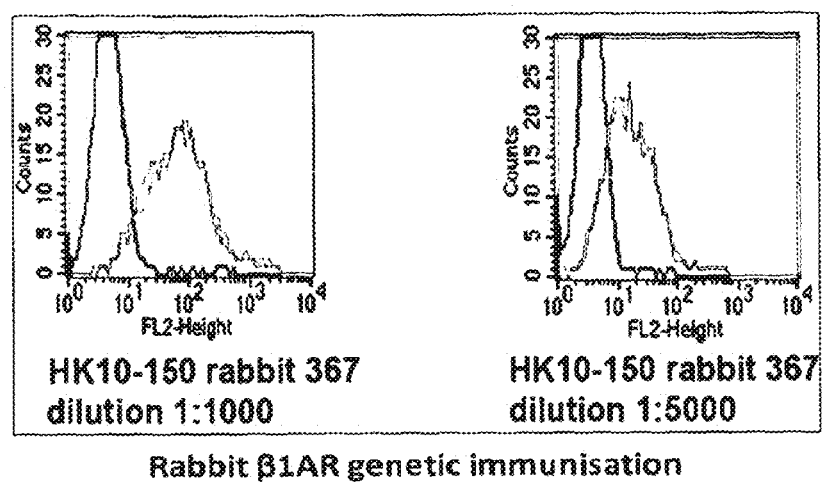
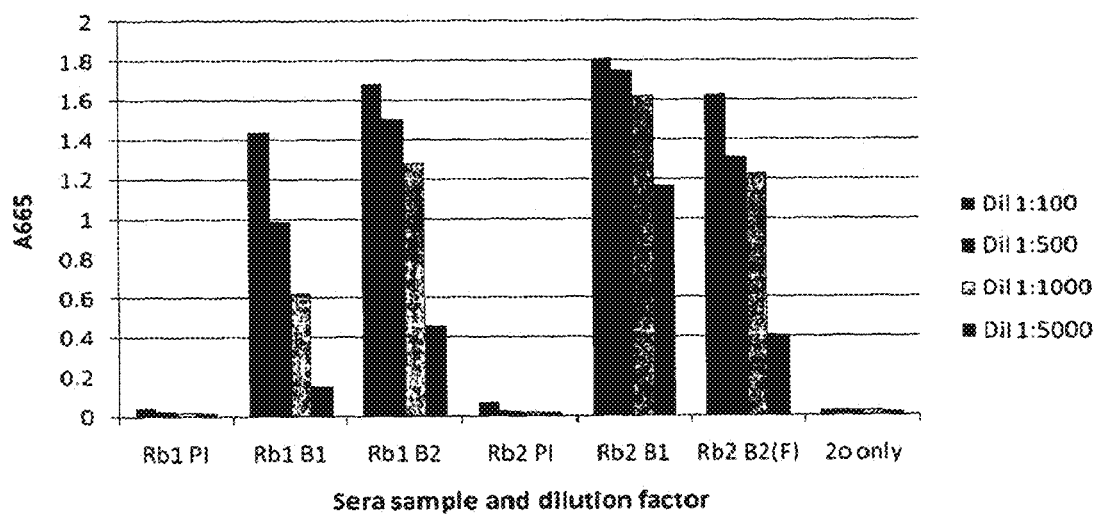

SEQUENCE LISTING

```
<160> NUMBER OF SEQ ID NOS: 12

<210> SEQ ID NO 1
<211> LENGTH: 483
<212> TYPE: PRT
<213> ORGANISM: Meleagris gallopavo

<400> SEQUENCE: 1

Met Gly Asp Gly Trp Leu Pro Pro Asp Cys Gly Pro His Asn Arg Ser
1               5                   10                  15

Gly Gly Gly Gly Ala Thr Ala Ala Pro Thr Gly Ser Arg Gln Val Ser
            20                  25                  30

Ala Glu Leu Leu Ser Gln Gln Trp Glu Ala Gly Met Ser Leu Leu Met
        35                  40                  45
```

-continued

```
Ala Leu Val Val Leu Ile Val Ala Gly Asn Val Leu Ile Ala
 50              55                  60

Ala Ile Gly Arg Thr Gln Arg Leu Gln Thr Leu Thr Asn Leu Phe Ile
 65              70                  75                  80

Thr Ser Leu Ala Cys Ala Asp Leu Val Met Gly Leu Leu Val Val Pro
                 85                  90                  95

Phe Gly Ala Thr Leu Val Val Arg Gly Thr Trp Leu Trp Gly Ser Phe
                100                 105                 110

Leu Cys Glu Cys Trp Thr Ser Leu Asp Val Leu Cys Val Thr Ala Ser
            115                 120                 125

Ile Glu Thr Leu Cys Val Ile Ala Ile Asp Arg Tyr Leu Ala Ile Thr
        130                 135                 140

Ser Pro Phe Arg Tyr Gln Ser Leu Met Thr Arg Ala Arg Ala Lys Val
145                 150                 155                 160

Ile Ile Cys Thr Val Trp Ala Ile Ser Ala Leu Val Ser Phe Leu Pro
                165                 170                 175

Ile Met Met His Trp Trp Arg Asp Glu Asp Pro Gln Ala Leu Lys Cys
                180                 185                 190

Tyr Gln Asp Pro Gly Cys Cys Asp Phe Val Thr Asn Arg Ala Tyr Ala
            195                 200                 205

Ile Ala Ser Ser Ile Ile Ser Phe Tyr Ile Pro Leu Leu Ile Met Ile
        210                 215                 220

Phe Val Tyr Leu Arg Val Tyr Arg Glu Ala Lys Glu Gln Ile Arg Lys
225                 230                 235                 240

Ile Asp Arg Cys Glu Gly Arg Phe Tyr Gly Ser Gln Glu Gln Pro Gln
                245                 250                 255

Pro Pro Pro Leu Pro Gln His Gln Pro Ile Leu Gly Asn Gly Arg Ala
                260                 265                 270

Ser Lys Arg Lys Thr Ser Arg Val Met Ala Met Arg Glu His Lys Ala
            275                 280                 285

Leu Lys Thr Leu Gly Ile Ile Met Gly Val Phe Thr Leu Cys Trp Leu
        290                 295                 300

Pro Phe Phe Leu Val Asn Ile Val Asn Val Phe Asn Arg Asp Leu Val
305                 310                 315                 320

Pro Asp Trp Leu Phe Val Phe Phe Asn Trp Leu Gly Tyr Ala Asn Ser
                325                 330                 335

Ala Phe Asn Pro Ile Ile Tyr Cys Arg Ser Pro Asp Phe Arg Lys Ala
                340                 345                 350

Phe Lys Arg Leu Leu Cys Phe Pro Arg Lys Ala Asp Arg Arg Leu His
            355                 360                 365

Ala Gly Gly Gln Pro Ala Pro Leu Pro Gly Gly Phe Ile Ser Thr Leu
        370                 375                 380

Gly Ser Pro Glu His Ser Pro Gly Gly Thr Trp Ser Asp Cys Asn Gly
385                 390                 395                 400

Gly Thr Arg Gly Gly Ser Glu Ser Ser Leu Glu Glu Arg His Ser Lys
                405                 410                 415

Thr Ser Arg Ser Glu Ser Lys Met Glu Arg Glu Lys Asn Ile Leu Ala
                420                 425                 430

Thr Thr Arg Phe Tyr Cys Thr Phe Leu Gly Asn Gly Asp Lys Ala Val
            435                 440                 445

Phe Cys Thr Val Leu Arg Ile Val Lys Leu Phe Glu Asp Ala Thr Cys
450                 455                 460
```

```
Thr Cys Pro His Thr His Lys Leu Lys Met Lys Trp Arg Phe Lys Gln
465                 470                 475                 480

His Gln Ala

<210> SEQ ID NO 2
<211> LENGTH: 477
<212> TYPE: PRT
<213> ORGANISM: Homo sapiens

<400> SEQUENCE: 2

Met Gly Ala Gly Val Leu Val Leu Gly Ala Ser Glu Pro Gly Asn Leu
1               5                   10                  15

Ser Ser Ala Ala Pro Leu Pro Asp Gly Ala Ala Thr Ala Ala Arg Leu
            20                  25                  30

Leu Val Pro Ala Ser Pro Pro Ala Ser Leu Leu Pro Pro Ala Ser Glu
        35                  40                  45

Ser Pro Glu Pro Leu Ser Gln Gln Trp Thr Ala Gly Met Gly Leu Leu
    50                  55                  60

Met Ala Leu Ile Val Leu Leu Ile Val Ala Gly Asn Val Leu Val Ile
65                  70                  75                  80

Val Ala Ile Ala Lys Thr Pro Arg Leu Gln Thr Leu Thr Asn Leu Phe
                85                  90                  95

Ile Met Ser Leu Ala Ser Ala Asp Leu Val Met Gly Leu Leu Val Val
            100                 105                 110

Pro Phe Gly Ala Thr Ile Val Val Trp Gly Arg Trp Glu Tyr Gly Ser
        115                 120                 125

Phe Phe Cys Glu Leu Trp Thr Ser Val Asp Val Leu Cys Val Thr Ala
    130                 135                 140

Ser Ile Glu Thr Leu Cys Val Ile Ala Leu Asp Arg Tyr Leu Ala Ile
145                 150                 155                 160

Thr Ser Pro Phe Arg Tyr Gln Ser Leu Leu Thr Arg Ala Arg Ala Arg
                165                 170                 175

Gly Leu Val Cys Thr Val Trp Ala Ile Ser Ala Leu Val Ser Phe Leu
            180                 185                 190

Pro Ile Leu Met His Trp Trp Arg Ala Glu Ser Asp Glu Ala Arg Arg
        195                 200                 205

Cys Tyr Asn Asp Pro Lys Cys Cys Asp Phe Val Thr Asn Arg Ala Tyr
    210                 215                 220

Ala Ile Ala Ser Ser Val Val Ser Phe Tyr Val Pro Leu Cys Ile Met
225                 230                 235                 240

Ala Phe Val Tyr Leu Arg Val Phe Arg Glu Ala Gln Lys Gln Val Lys
                245                 250                 255

Lys Ile Asp Ser Cys Glu Arg Arg Phe Leu Gly Gly Pro Ala Arg Pro
            260                 265                 270

Pro Ser Pro Ser Pro Ser Pro Val Pro Ala Pro Ala Pro Pro Pro Gly
        275                 280                 285

Pro Pro Arg Pro Ala Ala Ala Ala Thr Ala Pro Leu Ala Asn Gly
    290                 295                 300

Arg Ala Gly Lys Arg Arg Pro Ser Arg Leu Val Ala Leu Arg Glu Gln
305                 310                 315                 320

Lys Ala Leu Lys Thr Leu Gly Ile Ile Met Gly Val Phe Thr Leu Cys
                325                 330                 335

Trp Leu Pro Phe Phe Leu Ala Asn Val Val Lys Ala Phe His Arg Glu
            340                 345                 350
```

```
Leu Val Pro Asp Arg Leu Phe Val Phe Phe Asn Trp Leu Gly Tyr Ala
            355                 360                 365

Asn Ser Ala Phe Asn Pro Ile Ile Tyr Cys Arg Ser Pro Asp Phe Arg
        370                 375                 380

Lys Ala Phe Gln Gly Leu Leu Cys Cys Ala Arg Arg Ala Ala Arg Arg
385                 390                 395                 400

Arg His Ala Thr His Gly Asp Arg Pro Arg Ala Ser Gly Cys Leu Ala
                405                 410                 415

Arg Pro Gly Pro Pro Ser Pro Gly Ala Ala Ser Asp Asp Asp
            420                 425                 430

Asp Asp Val Val Gly Ala Thr Pro Pro Ala Arg Leu Leu Glu Pro Trp
            435                 440                 445

Ala Gly Cys Asn Gly Gly Ala Ala Ala Asp Ser Asp Ser Ser Leu Asp
    450                 455                 460

Glu Pro Cys Arg Pro Gly Phe Ala Ser Glu Ser Lys Val
465                 470                 475

<210> SEQ ID NO 3
<211> LENGTH: 413
<212> TYPE: PRT
<213> ORGANISM: Homo sapiens

<400> SEQUENCE: 3

Met Gly Gln Pro Gly Asn Gly Ser Ala Phe Leu Leu Ala Pro Asn Arg
1               5                   10                  15

Ser His Ala Pro Asp His Asp Val Thr Gln Gln Arg Asp Glu Val Trp
            20                  25                  30

Val Val Gly Met Gly Ile Val Met Ser Leu Ile Val Leu Ala Ile Val
        35                  40                  45

Phe Gly Asn Val Leu Val Ile Thr Ala Ile Ala Lys Phe Glu Arg Leu
    50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Met
                85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
        115                 120                 125

Val Asp Arg Tyr Phe Ala Ile Thr Ser Pro Phe Lys Tyr Gln Ser Leu
    130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
        195                 200                 205

Tyr Val Pro Leu Val Ile Met Val Phe Val Tyr Ser Arg Val Phe Gln
    210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
                245                 250                 255
```

Gly Leu Arg Arg Ser Ser Lys Phe Cys Leu Lys Glu His Lys Ala Leu
                260                 265                 270

Lys Thr Leu Gly Ile Ile Met Gly Thr Phe Thr Leu Cys Trp Leu Pro
            275                 280                 285

Phe Phe Ile Val Asn Ile Val His Val Ile Gln Asp Asn Leu Ile Arg
        290                 295                 300

Lys Glu Val Tyr Ile Leu Leu Asn Trp Ile Gly Tyr Val Asn Ser Gly
305                 310                 315                 320

Phe Asn Pro Leu Ile Tyr Cys Arg Ser Pro Asp Phe Arg Ile Ala Phe
                325                 330                 335

Gln Glu Leu Leu Cys Leu Arg Arg Ser Ser Leu Lys Ala Tyr Gly Asn
            340                 345                 350

Gly Tyr Ser Ser Asn Gly Asn Thr Gly Glu Gln Ser Gly Tyr His Val
        355                 360                 365

Glu Gln Glu Lys Glu Asn Lys Leu Leu Cys Glu Asp Leu Pro Gly Thr
370                 375                 380

Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
                405                 410

<210> SEQ ID NO 4
<211> LENGTH: 408
<212> TYPE: PRT
<213> ORGANISM: Homo sapiens

<400> SEQUENCE: 4

Met Ala Pro Trp Pro His Glu Asn Ser Ser Leu Ala Pro Trp Pro Asp
1               5                   10                  15

Leu Pro Thr Leu Ala Pro Asn Thr Ala Asn Thr Ser Gly Leu Pro Gly
            20                  25                  30

Val Pro Trp Glu Ala Ala Leu Ala Gly Ala Leu Leu Ala Leu Ala Val
        35                  40                  45

Leu Ala Thr Val Gly Gly Asn Leu Leu Val Ile Val Ala Ile Ala Trp
    50                  55                  60

Thr Pro Arg Leu Gln Thr Met Thr Asn Val Phe Val Thr Ser Leu Ala
65                  70                  75                  80

Ala Ala Asp Leu Val Met Gly Leu Leu Val Val Pro Pro Ala Ala Thr
                85                  90                  95

Leu Ala Leu Thr Gly His Trp Pro Leu Gly Ala Thr Gly Cys Glu Leu
            100                 105                 110

Trp Thr Ser Val Asp Val Leu Cys Val Thr Ala Ser Ile Glu Thr Leu
        115                 120                 125

Cys Ala Leu Ala Val Asp Arg Tyr Leu Ala Val Thr Asn Pro Leu Arg
    130                 135                 140

Tyr Gly Ala Leu Val Thr Lys Arg Cys Ala Arg Thr Ala Val Val Leu
145                 150                 155                 160

Val Trp Val Val Ser Ala Ala Val Ser Phe Ala Pro Ile Met Ser Gln
                165                 170                 175

Trp Trp Arg Val Gly Ala Asp Ala Glu Ala Gln Arg Cys His Ser Asn
            180                 185                 190

Pro Arg Cys Cys Ala Phe Ala Ser Asn Met Pro Tyr Val Leu Leu Ser
        195                 200                 205

Ser Ser Val Ser Phe Tyr Leu Pro Leu Leu Val Met Leu Phe Val Tyr

```
                    210                 215                 220
Ala Arg Val Phe Val Ala Thr Arg Gln Leu Arg Leu Leu Arg Gly
225                 230                 235                 240

Glu Leu Gly Arg Phe Pro Pro Glu Glu Ser Pro Pro Ala Pro Ser Arg
            245                 250                 255

Ser Leu Ala Pro Ala Pro Val Gly Thr Cys Ala Pro Pro Glu Gly Val
            260                 265                 270

Pro Ala Cys Gly Arg Arg Pro Ala Arg Leu Leu Pro Leu Arg Glu His
            275                 280                 285

Arg Ala Leu Cys Thr Leu Gly Leu Ile Met Gly Thr Phe Thr Leu Cys
290                 295                 300

Trp Leu Pro Phe Phe Leu Ala Asn Val Leu Arg Ala Leu Gly Gly Pro
305                 310                 315                 320

Ser Leu Val Pro Gly Pro Ala Phe Leu Ala Leu Asn Trp Leu Gly Tyr
                325                 330                 335

Ala Asn Ser Ala Phe Asn Pro Leu Ile Tyr Cys Arg Ser Pro Asp Phe
                340                 345                 350

Arg Ser Ala Phe Arg Arg Leu Leu Cys Arg Cys Gly Arg Arg Leu Pro
            355                 360                 365

Pro Glu Pro Cys Ala Ala Ala Arg Pro Ala Leu Phe Pro Ser Gly Val
370                 375                 380

Pro Ala Ala Arg Ser Ser Pro Ala Gln Pro Arg Leu Cys Gln Arg Leu
385                 390                 395                 400

Asp Gly Ala Ser Trp Gly Val Ser
                405

<210> SEQ ID NO 5
<211> LENGTH: 412
<212> TYPE: PRT
<213> ORGANISM: Homo sapiens

<400> SEQUENCE: 5

Met Pro Ile Met Gly Ser Ser Val Tyr Ile Thr Val Glu Leu Ala Ile
1               5                   10                  15

Ala Val Leu Ala Ile Leu Gly Asn Val Leu Val Cys Trp Ala Val Trp
            20                  25                  30

Leu Asn Ser Asn Leu Gln Asn Val Thr Asn Tyr Phe Val Val Ser Leu
        35                  40                  45

Ala Ala Ala Asp Ile Ala Val Gly Val Leu Ala Ile Pro Phe Ala Ile
    50                  55                  60

Thr Ile Ser Thr Gly Phe Cys Ala Ala Cys His Gly Cys Leu Phe Ile
65                  70                  75                  80

Ala Cys Phe Val Leu Val Leu Thr Gln Ser Ser Ile Phe Ser Leu Leu
                85                  90                  95

Ala Ile Ala Ile Asp Arg Tyr Ile Ala Ile Arg Ile Pro Leu Arg Tyr
            100                 105                 110

Asn Gly Leu Val Thr Gly Thr Arg Ala Lys Gly Ile Ile Ala Ile Cys
        115                 120                 125

Trp Val Leu Ser Phe Ala Ile Gly Leu Thr Pro Met Leu Gly Trp Asn
    130                 135                 140

Asn Cys Gly Gln Pro Lys Glu Gly Lys Asn His Ser Gln Gly Cys Gly
145                 150                 155                 160

Glu Gly Gln Val Ala Cys Leu Phe Glu Asp Val Val Pro Met Asn Tyr
                165                 170                 175
```

```
Met Val Tyr Phe Asn Phe Ala Cys Val Leu Val Pro Leu Leu Leu
            180                 185                 190

Met Leu Gly Val Tyr Leu Arg Ile Phe Leu Ala Ala Arg Gln Leu
        195                 200                 205

Lys Gln Met Glu Ser Gln Pro Leu Pro Gly Glu Arg Ala Arg Ser Thr
210                 215                 220

Leu Gln Lys Glu Val His Ala Ala Lys Ser Leu Ala Ile Ile Val Gly
225                 230                 235                 240

Leu Phe Ala Leu Cys Trp Leu Pro Leu His Ile Ile Asn Cys Phe Thr
                245                 250                 255

Phe Phe Cys Pro Asp Cys Ser His Ala Pro Leu Trp Leu Met Tyr Leu
            260                 265                 270

Ala Ile Val Leu Ser His Thr Asn Ser Val Val Asn Pro Phe Ile Tyr
            275                 280                 285

Ala Tyr Arg Ile Arg Glu Phe Arg Gln Thr Phe Arg Lys Ile Ile Arg
        290                 295                 300

Ser His Val Leu Arg Gln Gln Glu Pro Phe Lys Ala Ala Gly Thr Ser
305                 310                 315                 320

Ala Arg Val Leu Ala Ala His Gly Ser Asp Gly Glu Gln Val Ser Leu
                325                 330                 335

Arg Leu Asn Gly His Pro Pro Gly Val Trp Ala Asn Gly Ser Ala Pro
            340                 345                 350

His Pro Glu Arg Arg Pro Asn Gly Tyr Ala Leu Gly Leu Val Ser Gly
            355                 360                 365

Gly Ser Ala Gln Glu Ser Gln Gly Asn Thr Gly Leu Pro Asp Val Glu
        370                 375                 380

Leu Leu Ser His Glu Leu Lys Gly Val Cys Pro Glu Pro Pro Gly Leu
385                 390                 395                 400

Asp Asp Pro Leu Ala Gln Asp Gly Ala Gly Val Ser
                405                 410

<210> SEQ ID NO 6
<211> LENGTH: 332
<212> TYPE: PRT
<213> ORGANISM: Homo sapiens

<400> SEQUENCE: 6

Met Leu Leu Glu Thr Gln Asp Ala Leu Tyr Val Ala Leu Glu Leu Val
1               5                   10                  15

Ile Ala Ala Leu Ser Val Ala Gly Asn Val Leu Val Cys Ala Ala Val
            20                  25                  30

Gly Thr Ala Asn Thr Leu Gln Thr Pro Thr Asn Tyr Phe Leu Val Ser
        35                  40                  45

Leu Ala Ala Ala Asp Val Ala Val Gly Leu Phe Ala Ile Pro Phe Ala
    50                  55                  60

Ile Thr Ile Ser Leu Gly Phe Cys Thr Asp Phe Tyr Gly Cys Leu Phe
65                  70                  75                  80

Leu Ala Cys Phe Val Leu Val Leu Thr Gln Ser Ser Ile Phe Ser Leu
                85                  90                  95

Leu Ala Val Ala Val Asp Arg Tyr Leu Ala Ile Cys Val Pro Leu Arg
            100                 105                 110

Tyr Lys Ser Leu Val Thr Gly Thr Arg Ala Arg Gly Val Ile Ala Val
        115                 120                 125

Leu Trp Val Leu Ala Phe Gly Ile Gly Leu Thr Pro Phe Leu Gly Trp
    130                 135                 140
```

```
Asn Ser Lys Asp Ser Ala Thr Asn Asn Cys Thr Glu Pro Trp Asp Gly
145                 150                 155                 160

Thr Thr Asn Glu Ser Cys Cys Leu Val Lys Cys Leu Phe Glu Asn Val
                165                 170                 175

Val Pro Met Ser Tyr Met Val Tyr Phe Asn Phe Phe Gly Cys Val Leu
            180                 185                 190

Pro Pro Leu Leu Ile Met Leu Val Ile Tyr Ile Lys Ile Phe Leu Val
            195                 200                 205

Ala Cys Arg Gln Leu Gln Arg Thr Glu Leu Met Asp His Ser Arg Thr
210                 215                 220

Thr Leu Gln Arg Glu Ile His Ala Ala Lys Ser Leu Ala Met Ile Val
225                 230                 235                 240

Gly Ile Phe Ala Leu Cys Trp Leu Pro Val His Ala Val Asn Cys Val
                245                 250                 255

Thr Leu Phe Gln Pro Ala Gln Gly Lys Asn Lys Pro Lys Trp Ala Met
            260                 265                 270

Asn Met Ala Ile Leu Leu Ser His Ala Asn Ser Val Val Asn Pro Ile
            275                 280                 285

Val Tyr Ala Tyr Arg Asn Arg Asp Phe Arg Tyr Thr Phe His Lys Ile
            290                 295                 300

Ile Ser Arg Tyr Leu Leu Cys Gln Ala Asp Val Lys Ser Gly Asn Gly
305                 310                 315                 320

Gln Ala Gly Val Gln Pro Ala Leu Gly Val Gly Leu
                325                 330

<210> SEQ ID NO 7
<211> LENGTH: 318
<212> TYPE: PRT
<213> ORGANISM: Homo sapiens

<400> SEQUENCE: 7

Met Pro Asn Asn Ser Thr Ala Leu Ser Leu Ala Asn Val Thr Tyr Ile
1               5                   10                  15

Thr Met Glu Ile Phe Ile Gly Leu Cys Ala Ile Val Gly Asn Val Leu
                20                  25                  30

Val Ile Cys Val Val Lys Leu Asn Pro Ser Leu Gln Thr Thr Thr Phe
            35                  40                  45

Tyr Phe Ile Val Ser Leu Ala Leu Ala Asp Ile Ala Val Gly Val Leu
50                  55                  60

Val Met Pro Leu Ala Ile Val Val Ser Leu Gly Ile Thr Ile His Phe
65                  70                  75                  80

Tyr Ser Cys Leu Phe Met Thr Cys Leu Leu Leu Ile Phe Thr His Ala
                85                  90                  95

Ser Ile Met Ser Leu Leu Ala Ile Ala Val Asp Arg Tyr Leu Arg Val
            100                 105                 110

Lys Leu Thr Val Arg Tyr Lys Arg Val Thr Thr His Arg Arg Ile Trp
            115                 120                 125

Leu Ala Leu Gly Leu Cys Trp Leu Val Ser Phe Leu Val Gly Leu Thr
130                 135                 140

Pro Met Phe Gly Trp Asn Met Lys Leu Thr Ser Glu Tyr His Arg Asn
145                 150                 155                 160

Val Thr Phe Leu Ser Cys Gln Phe Val Ser Val Met Arg Met Asp Tyr
                165                 170                 175

Met Val Tyr Phe Ser Phe Leu Thr Trp Ile Phe Ile Pro Leu Val Val
```

```
            180                 185                 190
Met Cys Ala Ile Tyr Leu Asp Ile Phe Tyr Ile Ile Arg Asn Lys Leu
            195                 200                 205

Ser Leu Asn Leu Ser Asn Ser Lys Glu Thr Gly Ala Phe Tyr Gly Arg
210                 215                 220

Glu Phe Lys Thr Ala Lys Ser Leu Phe Leu Val Leu Phe Leu Phe Ala
225                 230                 235                 240

Leu Ser Trp Leu Pro Leu Ser Ile Ile Asn Cys Ile Tyr Phe Asn
                    245                 250                 255

Gly Glu Val Pro Gln Leu Val Leu Tyr Met Gly Ile Leu Leu Ser His
                260                 265                 270

Ala Asn Ser Met Met Asn Pro Ile Val Tyr Ala Tyr Lys Ile Lys Lys
            275                 280                 285

Phe Lys Glu Thr Tyr Leu Leu Ile Leu Lys Ala Cys Val Val Cys His
        290                 295                 300

Pro Ser Asp Ser Leu Asp Thr Ser Ile Glu Lys Asn Ser Glu
305                 310                 315

<210> SEQ ID NO 8
<211> LENGTH: 326
<212> TYPE: PRT
<213> ORGANISM: Homo sapiens

<400> SEQUENCE: 8

Met Pro Pro Ser Ile Ser Ala Phe Gln Ala Ala Tyr Ile Gly Ile Glu
1               5                   10                  15

Val Leu Ile Ala Leu Val Ser Val Pro Gly Asn Val Leu Val Ile Trp
            20                  25                  30

Ala Val Lys Val Asn Gln Ala Leu Arg Asp Ala Thr Phe Cys Phe Ile
        35                  40                  45

Val Ser Leu Ala Val Ala Asp Val Ala Val Gly Ala Leu Val Ile Pro
    50                  55                  60

Leu Ala Ile Leu Ile Asn Ile Gly Pro Gln Thr Tyr Phe His Thr Cys
65                  70                  75                  80

Leu Met Val Ala Cys Pro Val Leu Ile Leu Thr Gln Ser Ser Ile Leu
                85                  90                  95

Ala Leu Leu Ala Ile Ala Val Asp Arg Tyr Leu Arg Val Lys Ile Pro
            100                 105                 110

Leu Arg Tyr Lys Met Val Val Thr Pro Arg Arg Ala Ala Val Ala Ile
        115                 120                 125

Ala Gly Cys Trp Ile Leu Ser Phe Val Val Gly Leu Thr Pro Met Phe
    130                 135                 140

Gly Trp Asn Asn Leu Ser Ala Val Glu Arg Ala Trp Ala Ala Asn Gly
145                 150                 155                 160

Ser Met Gly Glu Pro Val Ile Lys Cys Glu Phe Glu Lys Val Ile Ser
                165                 170                 175

Met Glu Tyr Met Val Tyr Phe Asn Phe Phe Val Trp Val Leu Pro Pro
            180                 185                 190

Leu Leu Leu Met Val Leu Ile Tyr Leu Glu Val Phe Tyr Leu Ile Arg
        195                 200                 205

Lys Gln Leu Asn Lys Lys Val Ser Ala Ser Ser Gly Asp Pro Gln Lys
    210                 215                 220

Tyr Tyr Gly Lys Glu Leu Lys Ile Ala Lys Ser Leu Ala Leu Ile Leu
225                 230                 235                 240
```

```
Phe Leu Phe Ala Leu Ser Trp Leu Pro Leu His Ile Leu Asn Cys Ile
                245                 250                 255

Thr Leu Phe Cys Pro Ser Cys His Lys Pro Ser Ile Leu Thr Tyr Ile
            260                 265                 270

Ala Ile Phe Leu Thr His Gly Asn Ser Ala Met Asn Pro Ile Val Tyr
        275                 280                 285

Ala Phe Arg Ile Gln Lys Phe Arg Val Thr Phe Leu Lys Ile Trp Asn
    290                 295                 300

Asp His Phe Arg Cys Gln Pro Ala Pro Pro Ile Asp Glu Asp Leu Pro
305                 310                 315                 320

Glu Glu Arg Pro Asp Asp
                325

<210> SEQ ID NO 9
<211> LENGTH: 424
<212> TYPE: PRT
<213> ORGANISM: Rattus norvegicus

<400> SEQUENCE: 9

Met His Leu Asn Ser Val Pro Gln Gly Thr Pro Gly Glu Pro Asp
1               5                   10                  15

Ala Gln Pro Phe Ser Gly Pro Gln Ser Glu Met Glu Ala Thr Phe Leu
            20                  25                  30

Ala Leu Ser Leu Ser Asn Gly Ser Gly Asn Thr Ser Glu Ser Asp Thr
        35                  40                  45

Ala Gly Pro Asn Ser Asp Leu Asp Val Asn Thr Asp Ile Tyr Ser Lys
    50                  55                  60

Val Leu Val Thr Ala Ile Tyr Leu Ala Leu Phe Val Val Gly Thr Val
65                  70                  75                  80

Gly Asn Ser Val Thr Ala Phe Thr Leu Ala Arg Lys Lys Ser Leu Gln
                85                  90                  95

Ser Leu Gln Ser Thr Val His Tyr His Leu Gly Ser Leu Ala Leu Ser
            100                 105                 110

Asp Leu Leu Ile Leu Leu Leu Ala Met Pro Val Glu Leu Tyr Asn Phe
        115                 120                 125

Ile Trp Val His His Pro Trp Ala Phe Gly Asp Ala Gly Cys Arg Gly
    130                 135                 140

Tyr Tyr Phe Leu Arg Asp Ala Cys Thr Tyr Ala Thr Ala Leu Asn Val
145                 150                 155                 160

Ala Ser Leu Ser Val Glu Arg Tyr Leu Ala Ile Cys His Pro Phe Lys
                165                 170                 175

Ala Lys Thr Leu Met Ser Arg Ser Arg Thr Lys Lys Phe Ile Ser Ala
            180                 185                 190

Ile Trp Leu Ala Ser Ala Leu Leu Ala Ile Pro Met Leu Phe Thr Met
    195                 200                 205

Gly Leu Gln Asn Arg Ser Gly Asp Gly Thr His Pro Gly Gly Leu Val
210                 215                 220

Cys Thr Pro Ile Val Asp Thr Ala Thr Val Lys Val Val Ile Gln Val
225                 230                 235                 240

Asn Thr Phe Met Ser Phe Leu Phe Pro Met Leu Val Ile Ser Ile Leu
                245                 250                 255

Asn Thr Val Ile Ala Asn Lys Leu Thr Val Met Val His Gln Ala Ala
            260                 265                 270

Glu Gln Gly Arg Val Cys Thr Val Gly Thr His Asn Gly Leu Glu His
        275                 280                 285
```

Ser Thr Phe Asn Met Thr Ile Glu Pro Gly Arg Val Gln Ala Leu Arg
        290                 295                 300

His Gly Val Leu Val Leu Arg Ala Val Val Ile Ala Phe Val Val Cys
305                 310                 315                 320

Trp Leu Pro Tyr His Val Arg Arg Leu Met Phe Cys Tyr Ile Ser Asp
                325                 330                 335

Glu Gln Trp Thr Thr Phe Leu Phe Asp Phe Tyr His Tyr Phe Tyr Met
            340                 345                 350

Leu Thr Asn Ala Leu Phe Tyr Val Ser Ser Ala Ile Asn Pro Ile Leu
        355                 360                 365

Tyr Asn Leu Val Ser Ala Asn Phe Arg Gln Val Phe Leu Ser Thr Leu
370                 375                 380

Ala Cys Leu Cys Pro Gly Trp Arg His Arg Arg Lys Lys Arg Pro Thr
385                 390                 395                 400

Phe Ser Arg Lys Pro Asn Ser Met Ser Ser Asn His Ala Phe Ser Thr
                405                 410                 415

Ser Ala Thr Arg Glu Thr Leu Tyr
            420

<210> SEQ ID NO 10
<211> LENGTH: 418
<212> TYPE: PRT
<213> ORGANISM: Homo sapiens

<400> SEQUENCE: 10

Met Arg Leu Asn Ser Ser Ala Pro Gly Thr Pro Gly Thr Pro Ala Ala
1               5                   10                  15

Asp Pro Phe Gln Arg Ala Gln Ala Gly Leu Glu Glu Ala Leu Leu Ala
            20                  25                  30

Pro Gly Phe Gly Asn Ala Ser Gly Asn Ala Ser Glu Arg Val Leu Ala
        35                  40                  45

Ala Pro Ser Ser Glu Leu Asp Val Asn Thr Asp Ile Tyr Ser Lys Val
    50                  55                  60

Leu Val Thr Ala Val Tyr Leu Ala Leu Phe Val Val Gly Thr Val Gly
65                  70                  75                  80

Asn Thr Val Thr Ala Phe Thr Leu Ala Arg Lys Lys Ser Leu Gln Ser
                85                  90                  95

Leu Gln Ser Thr Val His Tyr His Leu Gly Ser Leu Ala Leu Ser Asp
            100                 105                 110

Leu Leu Thr Leu Leu Ala Met Pro Val Glu Leu Tyr Asn Phe Ile
        115                 120                 125

Trp Val His His Pro Trp Ala Phe Gly Asp Ala Gly Cys Arg Gly Tyr
    130                 135                 140

Tyr Phe Leu Arg Asp Ala Cys Thr Tyr Ala Thr Ala Leu Asn Val Ala
145                 150                 155                 160

Ser Leu Ser Val Glu Arg Tyr Leu Ala Ile Cys His Pro Phe Lys Ala
                165                 170                 175

Lys Thr Leu Met Ser Arg Ser Arg Thr Lys Lys Phe Ile Ser Ala Ile
            180                 185                 190

Trp Leu Ala Ser Ala Leu Leu Ala Val Pro Met Leu Phe Thr Met Gly
        195                 200                 205

Glu Gln Asn Arg Ser Ala Asp Gly Gln His Ala Gly Gly Leu Val Cys
    210                 215                 220

Thr Pro Thr Ile His Thr Ala Thr Val Lys Val Val Ile Gln Val Asn

```
                225                 230                 235                 240
            Thr Phe Met Ser Phe Ile Phe Pro Met Val Val Ile Ser Val Leu Asn
                            245                 250                 255

Thr Ile Ile Ala Asn Lys Leu Thr Val Met Val Arg Gln Ala Ala Glu
                        260                 265                 270

Gln Gly Gln Val Cys Thr Val Gly Glu His Ser Thr Phe Ser Met
                    275                 280                 285

Ala Ile Glu Pro Gly Arg Val Gln Ala Leu Arg His Gly Val Arg Val
                290                 295                 300

Leu Arg Ala Val Val Ile Ala Phe Val Val Cys Trp Leu Pro Tyr His
            305                 310                 315                 320

Val Arg Arg Leu Met Phe Cys Tyr Ile Ser Asp Glu Gln Trp Thr Pro
                            325                 330                 335

Phe Leu Tyr Asp Phe Tyr His Tyr Phe Tyr Met Val Thr Asn Ala Leu
                        340                 345                 350

Phe Tyr Val Ser Ser Thr Ile Asn Pro Ile Leu Tyr Asn Leu Val Ser
                    355                 360                 365

Ala Asn Phe Arg His Ile Phe Leu Ala Thr Leu Ala Cys Leu Cys Pro
                370                 375                 380

Val Trp Arg Arg Arg Lys Arg Pro Ala Phe Ser Arg Lys Ala Asp
            385                 390                 395                 400

Ser Val Ser Ser Asn His Thr Leu Ser Ser Asn Ala Thr Arg Glu Thr
                            405                 410                 415

Leu Tyr

<210> SEQ ID NO 11
<211> LENGTH: 409
<212> TYPE: PRT
<213> ORGANISM: Homo sapiens

<400> SEQUENCE: 11

Met Glu Thr Ser Ser Pro Arg Pro Pro Arg Pro Ser Ser Asn Pro Gly
            1               5                   10                  15

Leu Ser Leu Asp Ala Arg Leu Gly Val Asp Thr Arg Leu Trp Ala Lys
                        20                  25                  30

Val Leu Phe Thr Ala Leu Tyr Ala Leu Ile Trp Ala Leu Gly Ala Ala
                    35                  40                  45

Gly Asn Ala Leu Ser Val His Val Val Leu Lys Ala Arg Ala Gly Arg
                50                  55                  60

Ala Gly Arg Leu Arg His His Val Leu Ser Leu Ala Leu Ala Gly Leu
            65                  70                  75                  80

Leu Leu Leu Leu Val Gly Val Pro Val Glu Leu Tyr Ser Phe Val Trp
                            85                  90                  95

Phe His Tyr Pro Trp Val Phe Gly Asp Leu Gly Cys Arg Gly Tyr Tyr
                        100                 105                 110

Phe Val His Glu Leu Cys Ala Tyr Ala Thr Val Leu Ser Val Ala Gly
                    115                 120                 125

Leu Ser Ala Glu Arg Cys Leu Ala Val Cys Gln Pro Leu Arg Ala Arg
                130                 135                 140

Ser Leu Leu Thr Pro Arg Arg Thr Arg Trp Leu Val Ala Leu Ser Trp
            145                 150                 155                 160

Ala Ala Ser Leu Gly Leu Ala Leu Pro Met Ala Val Ile Met Gly Gln
                            165                 170                 175

Lys His Glu Leu Glu Thr Ala Asp Gly Glu Pro Glu Pro Ala Ser Arg
```

```
            180                 185                 190
Val Cys Thr Val Leu Val Ser Arg Thr Ala Leu Gln Val Phe Ile Gln
            195                 200                 205

Val Asn Val Leu Val Ser Phe Val Leu Pro Leu Ala Leu Thr Ala Phe
        210                 215                 220

Leu Asn Gly Val Thr Val Ser His Leu Leu Ala Leu Cys Ser Gln Val
225                 230                 235                 240

Pro Ser Thr Ser Thr Pro Gly Ser Ser Thr Pro Ser Arg Leu Glu Leu
                245                 250                 255

Leu Ser Glu Glu Gly Leu Leu Ser Phe Ile Val Trp Lys Lys Thr Phe
            260                 265                 270

Ile Gln Gly Gly Gln Val Ser Leu Val Arg His Lys Asp Val Arg Arg
        275                 280                 285

Ile Arg Ser Leu Gln Arg Ser Val Gln Val Leu Arg Ala Ile Val Val
290                 295                 300

Met Tyr Val Ile Cys Trp Leu Pro Tyr His Ala Arg Arg Leu Met Tyr
305                 310                 315                 320

Cys Tyr Val Pro Asp Asp Ala Trp Thr Asp Pro Leu Tyr Asn Phe Tyr
                325                 330                 335

His Tyr Phe Tyr Met Val Thr Asn Thr Leu Phe Tyr Val Ser Ser Ala
            340                 345                 350

Val Thr Pro Leu Leu Tyr Asn Ala Val Ser Ser Ser Phe Arg Lys Leu
        355                 360                 365

Phe Leu Glu Ala Val Ser Ser Leu Cys Gly Glu His His Pro Met Lys
370                 375                 380

Arg Leu Pro Pro Lys Pro Gln Ser Pro Thr Leu Met Asp Thr Ala Ser
385                 390                 395                 400

Gly Phe Gly Asp Pro Pro Glu Thr Arg
                405

<210> SEQ ID NO 12
<211> LENGTH: 460
<212> TYPE: PRT
<213> ORGANISM: Homo sapiens

<400> SEQUENCE: 12

Met Asn Thr Ser Ala Pro Pro Ala Val Ser Pro Asn Ile Thr Val Leu
1               5                   10                  15

Ala Pro Gly Lys Gly Pro Trp Gln Val Ala Phe Ile Gly Ile Thr Thr
            20                  25                  30

Gly Leu Leu Ser Leu Ala Thr Val Thr Gly Asn Leu Leu Val Leu Ile
        35                  40                  45

Ser Phe Lys Val Asn Thr Glu Leu Lys Thr Val Asn Asn Tyr Phe Leu
    50                  55                  60

Leu Ser Leu Ala Cys Ala Asp Leu Ile Ile Gly Thr Phe Ser Met Asn
65                  70                  75                  80

Leu Tyr Thr Thr Tyr Leu Leu Met Gly His Trp Ala Leu Gly Thr Leu
                85                  90                  95

Ala Cys Asp Leu Trp Leu Ala Leu Asp Tyr Val Ala Ser Asn Ala Ser
            100                 105                 110

Val Met Asn Leu Leu Leu Ile Ser Phe Asp Arg Tyr Phe Ser Val Thr
        115                 120                 125

Arg Pro Leu Ser Tyr Arg Ala Lys Arg Thr Pro Arg Arg Ala Ala Leu
    130                 135                 140
```

-continued

```
Met Ile Gly Leu Ala Trp Leu Val Ser Phe Val Leu Trp Ala Pro Ala
145                 150                 155                 160

Ile Leu Phe Trp Gln Tyr Leu Val Gly Glu Arg Thr Val Leu Ala Gly
                165                 170                 175

Gln Cys Tyr Ile Gln Phe Leu Ser Gln Pro Ile Ile Thr Phe Gly Thr
                180                 185                 190

Ala Met Ala Ala Phe Tyr Leu Pro Val Thr Val Met Cys Thr Leu Tyr
        195                 200                 205

Trp Arg Ile Tyr Arg Glu Thr Glu Asn Arg Ala Arg Glu Leu Ala Ala
        210                 215                 220

Leu Gln Gly Ser Glu Thr Pro Gly Lys Gly Gly Gly Ser Ser Ser Ser
225                 230                 235                 240

Ser Glu Arg Ser Gln Pro Gly Ala Glu Gly Ser Pro Glu Thr Pro Pro
                245                 250                 255

Gly Arg Cys Cys Arg Cys Cys Arg Ala Pro Arg Leu Leu Gln Ala Tyr
                260                 265                 270

Ser Trp Lys Glu Glu Glu Glu Asp Glu Gly Ser Met Glu Ser Leu
        275                 280                 285

Thr Ser Ser Glu Gly Glu Glu Pro Gly Ser Glu Val Val Ile Lys Met
        290                 295                 300

Pro Met Val Asp Pro Glu Ala Gln Ala Pro Thr Lys Gln Pro Pro Arg
305                 310                 315                 320

Ser Ser Pro Asn Thr Val Lys Arg Pro Thr Lys Lys Gly Arg Asp Arg
                325                 330                 335

Ala Gly Lys Gly Gln Lys Pro Arg Gly Lys Glu Gln Leu Ala Lys Arg
                340                 345                 350

Lys Thr Phe Ser Leu Val Lys Glu Lys Lys Ala Ala Arg Thr Leu Ser
        355                 360                 365

Ala Ile Leu Leu Ala Phe Ile Leu Thr Trp Thr Pro Tyr Asn Ile Met
        370                 375                 380

Val Leu Val Ser Thr Phe Cys Lys Asp Cys Val Pro Glu Thr Ile Trp
385                 390                 395                 400

Glu Leu Gly Tyr Trp Leu Cys Tyr Val Asn Ser Thr Ile Asn Pro Met
                405                 410                 415

Cys Tyr Ala Leu Cys Asn Lys Ala Phe Arg Asp Thr Phe Arg Leu Leu
                420                 425                 430

Leu Leu Cys Arg Trp Asp Lys Arg Arg Trp Arg Lys Ile Pro Lys Arg
        435                 440                 445

Pro Gly Ser Val His Arg Thr Pro Ser Arg Gln Cys
450                 455                 460
```

VACCINES COMPRISING MUTANT GPCRS WITH INCREASED CONFORMATIONAL STABILITY RELATIVE TO PARENT RECEPTORS

RELATED APPLICATIONS

This application is a national stage filing under 35 U.S.C. §371 of international application PCT/GB2011/001177, filed Aug. 5, 2011, which was published under PCT Article 21(2) in English, and claims the benefit under 35 U.S.C. §119(e) of U.S. Provisional Application Ser. No. 61/375,626, filed on Aug. 20, 2010, the disclosure of each of which is herein incorporated by reference in its entirety.

The present invention relates to the use of G-protein coupled receptors (GPCRs) or polynucleotides encoding said GPCRs, as a vaccine.

GPCRs constitute a very large family of proteins that control many physiological processes and are the targets of many effective drugs. Thus, they are of considerable pharmacological importance. A list of GPCRs is given in Foord et al (2005) Pharmacol Rev. 57, 279-288, which is incorporated herein by reference. GPCRs are generally unstable when isolated, and despite considerable efforts, it has only been possible to crystallise bovine rhodopsin, which naturally is exceptionally stable and the beta 2 adrenergic receptor which was crystallised as a fusion protein or in complex with an antibody fragment.

GPCRs are druggable targets, and reference is made particularly to Overington et al (2006) Nature Rev. Drug Discovery 5, 993-996 which indicates that over a quarter of present drugs have a GPCR as a target.

GPCRs are thought to exist in multiple distinct conformations which are associated with different pharmacological classes of ligand such as agonists and antagonists, and to cycle between these conformations in order to function (Kenakin T. (1997) Ann N Y Acad Sci 812, 116-125). Switching between conformations contributes to the difficulty in obtaining crystal structures of receptors.

The generation of conformation-specific binding partners to GPCRs is hindered by several factors. For example, GPCRs generally have poor stability when removed from their native membrane environment that severely restricts the range of conditions that can be explored without their immediate denaturation or precipitation. The inability to produce purified GPCRs in their native conformation prevents their use in a wide range of screening paradigms which depend on the use of purified receptors. Thus, GPCR screening has traditionally depended on assays in which the receptor is present in cell membranes or whole cells.

Many GPCRs represent important therapeutic targets which could be exploited by biotherapeutics such as antibodies. The generation of therapeutic antibodies for GPCRs has been extremely difficult. The usual route taken to produce antibodies would be to use small peptide fragments of the receptor for immunization. However such fragments do not retain their native conformation and often result in antibodies that can bind to and label the receptor but have no functional agonist or antagonist activity. Due to the unique physical conformation of GPCRs it is also known that biotherapeutics such as antibodies recognise combinations of polypeptide 'loops', features that are lost when peptide fragments are used in isolation. It is well known that the local membrane environment of GPCRs maintains the tertiary conformation of the protein, and governs which epitopes are present on the extracellular surface. These epitopes can in theory be recognised, however it is difficult to raise antibodies to membranes or membrane fragments containing a target GPCR as these preparations inevitably contain other non-target GPCRs and membrane-associated proteins, and other membrane components such as lipoproteins, apolipoproteins, lipids, phosophoinsositol lipids and liposaccharides which can act as non-desired antigens in the antibody selection and production process.

Whilst GPCRs offer great potential as therapeutic targets, we have now appreciated that one may use the GPCRs themselves directly as a vaccine.

In a first aspect of the invention there is provided a GPCR or a polynucleotide encoding said GPCR for use as a vaccine.

By "vaccine" we mean an immunogenic molecule that is administered to a subject or patient in order to produce a desired effect in vivo. In the case of the GPCR molecules of the invention, this desired effect will be antagonism or agonism of a receptor. The desired effect will depend on the receptor and biological pathway being targeted. However, a preferred effect is a desired therapeutic or prophylactic effect.

By "GPCR" we mean a G protein coupled receptor or polypeptide that has the signalling activity of a GPCR and retains an intact 7TM region. The GPCR molecules of the invention are preferably full length wild type sequences including natural polymorphisms or mutant GPCR molecules that have been altered so as to improve one or more properties of the GPCR e.g. stability.

The GPCRs of the invention can include wildtype and mutant GPCRs wherein mutant GPCRs may be stabilised GPCRs biased towards a particular conformation such as agonist or antagonist. Such conformationally stabilised GPCRs are then used for vaccination.

Either a polynucleotide sequence (eg DNA) or protein can be administered to harness the patient's immune response in order to stimulate the generation of an individual's own antibodies to produce the desired effect in vivo. It is preferred if the vaccine comprises an expression vector comprising a GPCR sequence which can be expressed upon administration to a patient to produce the encoded GPCR which in turn generates an immune response to bring about a desired effect in vivo.

We have previously developed a methodology for the stabilisation of a GPCR in a biologically relevant conformation (see WO 2009/081136) describing the production of stabilised GPCRs known as StaRs that enables the purification of recombinant G protein coupled receptors that maintain their conformation, stability and function when purified from the cell membrane. In addition, this platform technology also provides the means to engineer receptors biased either towards agonist conformation or the antagonist conformation (see also Magnani et al, 2008; Serrano-Vega et al, 2008; Shibata et al, 2009). All of the preferred mutant and stabilised GPCRs described therein are preferred for use in the present invention. Such stabilised receptors have a number of advantages, for example stability, elevated yields of purified protein, reduced denaturation and reduced non-specific binding.

The stability of the mutant GPCRs in a range of detergents, surfactants and solubilisation buffers enables their purification outside of their normal membrane environment. Therefore, the GPCR can be provided in an isolated form removed from non-desired antigens such as non-target GPCRs, membrane associated proteins and other membrane components such as lipoproteins, apolipoproteins, lipis, phosphoinositol lipids and liposaccharides.

Where a stable mutant GPCR is used in the present invention it is preferably selected and prepared using any of the methods as described in PCT applications WO 2008/114020, WO 2009/114020 and WO 2009/081136.

Suitable GPCRs for use in the practice of the invention include, but are not limited to β-adrenergic receptor, adenosine receptor, in particular adenosine $A_{2a}$ receptor, and neurotensin receptor (NTR). Other suitable GPCRs are well known in the art and include those listed in Overington et al supra. In addition, the International Union of Pharmacology produces a list of GPCRs (Foord et al (2005) *Pharmacol. Rev.* 57, 279-288, and this list is periodically updated at http://www.iuphar-db.org/GPCR/ReceptorFamiliesForward).

The amino acid sequences (and the nucleotide sequences of the cDNAs which encode them) of many GPCRs are readily available, for example by reference to GenBank. In particular, Foord et al supra gives the human gene symbols and human, mouse and rat gene IDs from Entrez Gene (ncbi.nlm.nih.gov/entrez). It should be noted, also, that because the sequence of the human genome is substantially complete, the amino acid sequences of human GPCRs can be deduced therefrom.

Although the GPCR may be derived from any source, it is particularly preferred if it is from a eukaryotic source. It is particularly preferred if it is derived from a vertebrate source such as a mammal or a bird. It is particularly preferred if the GPCR is derived from rat, mouse, rabbit or dog or non-human primate or man, or from chicken or turkey. For the avoidance of doubt, we include within the meaning of "derived from" that a cDNA or gene was originally obtained using genetic material from the source, but that the protein may be expressed in any host cell subsequently. Thus, it will be plain that a eukaryotic GPCR (such as an avian or mammalian GPCR) may be expressed in a prokaryotic host cell, such as *E. coli*, but be considered to be avian- or mammalian-derived, as the case may be.

In some instances, the GPCR may be composed of more than one different subunit. For example, the calcitonin gene-related peptide receptor requires the binding of a single transmembrane helix protein (RAMP1) to acquire its physiological ligand binding characteristics. Effector, accessory, auxiliary or GPCR-interacting proteins which combine with the GPCR to form or modulate a functional complex are well known in the art and include, for example, receptor kinases, G-proteins and arrestins (Bockaert et al (2004) *Curr Opinion Drug Discov and Dev* 7, 649-657).

Preferably the GPCR has increased stability in a particular conformation relative to a parent GPCR. By increased stability we include the meaning of a mutant GPCR showing less denaturation under denaturing conditions such as heat, a detergent, a chaotropic agent or extreme of pH, compared to the parent GPCR.

Conveniently the stabilised GPCR has increased stability in the antagonist conformation, or in the agonist conformation.

By "agonist conformation" we mean the GPCR exists in a three dimensional conformation that causes agonistic effects.

By "antagonist conformation" we mean we mean the GPCR exists in a three dimensional conformation that causes antagonistic effects.

In a further aspect of the invention there is provided a method of antagonising or agonising a GPCR receptor in vivo comprising administering to a subject a vaccine according to the invention.

Preferably the GPCR or polynucleotide encoding the same is administered to the subject at two or more intervals.

Conveniently the subject is a mammal, preferably a human.

In one embodiment the GPCR may be combined with an adjuvant, for use as a vaccine. In the embodiment in which the GPCR is administered as an expression vector, the expression vector may further comprise a sequence which can be expressed to produce an adjuvant in vivo.

Adjuvant strategies are often used to enhance immune responses, however it is also known that the choice of adjuvant has to be carefully selected for compatibility with the immunogen (as well as for use in humans). Examples of suitable adjuvants are provided below.

Lipid A (monophosphoryl lipid A-MPL) is based on lipids extracted from bacterial membranes and may provide stabilisation properties to a GPCR once administered into the mammalian bloodstream. MPL is also a potent stimulator of the immune system, and has been used as an adjuvant in humans. Other adjuvants, such as Gerbu's MM (created specifically for generating mouse monoclonals) and Pharma (created specifically for generating antibodies in larger mammals, such as rabbits) have also undergone preliminary evaluation. These adjuvants contain components such as GMDP, a glycopeptide derived from *L. bulgaricus* cell walls that induces T-cell responses that provide long-lasting immunity, and cationic nanoparticles in a colloidal suspension that replace the classical "water-in-oil" emulsions. Such adjuvants may provide further stabilisation properties to GPCRs during vaccination. Other additions to these adjuvants include Cimetidine, which is a histamine antagonist and generally enhances immune responsivity, and Saponin, which is used as a stimulator of the immune system. Freunds adjuvant may also be used although since it is known to be denaturing particularly for conformational epitopes, it may not always be suitable.

Although adjuvants such as lipid A may be used it is a feature of the present invention that in certain embodiments no adjuvants are necessary.

GPCRs naturally exist in multiple conformations ranging from the fully inactive ground state (R) to the fully activated state (R*). For any given receptor, equilibrium exists between these two states that determines the basal level of activity in cells. Once solubilised, a receptor may continue to exist in multiple conformations and transition between states, which can contribute to instability and resultant unfolding. Different conformations will have different levels of stability. The flexibility of GPCRs, which is fundamental to their signalling function, represents one of the greatest impediments to maintaining the stability of solubilised receptors.

Various expression systems have been developed for the expression of GPCRs, each with their own particular advantages and disadvantages. To dates the majority of the work has focused on four main expression systems: bacterial (*E. coli*), yeasts (*Saccharomyces cerevisiae, Schizosaccharomyces pombe, Pichia pastoris*) insect cells (*Spodoptera frugiperda* Sf9, Sf21, *Trichoplusia ni* Hi5 and *Drosophila* Schneider S2) and mammalian cells (CHO, HEK, COS-1 etc). However, other systems have been investigated; these include cell-free expression systems and the more unusual use of whole organisms (*Drosophila melanogater, Xenopus laevis* and Silkworm). All of these expression systems are applicable for the expression and purification of StaR protein.

Bacterial Expression

Whilst a number of systems are available for heterologous protein production, *E. coli* remains one of the most attractive because of its ease of use with respect to both cloning and the scale up of protein expression. There are two possible strategies that may be used for the expression of GPCRs in a bacterial expression system:

(a) expression of functional, membrane-inserted receptors;

(b) expression of incorrectly folded, aggregated protein to which a refolding strategy is applied to obtain a functionally active receptor.

Initial successes in using bacterial expression to achieve the soluble expression of functionally active GPCR involved the use of fusion proteins, as exemplified by $\beta_2$AR as an N-terminal fusion with $\beta$-galactosidase; resulting in expression levels of 0.4 pmol/mg (Marullo et al, 1988). In addition, the combination of promoter and fusion partners can also be used for enhanced soluble expression, for example, NTR receptor (Grisshammer et al, 1993; Tucker & Grisshammer, 1996) and the human adenosine $A_{2a}$ receptor (Weiss & Grisshammer, 2002) where the expression constructs included an MBP fusion partner with an N-terminal signal peptide and the replacement of the tac promoter with a weaker lac promoter. The exact role of the fusion partner is unclear, but it is thought that the MBP may drive the correct insertion of the fused GPCR into the membrane through its translocation to the periplasm (Mancia & Hendrikson, 2007). The MBP fusion partner also assists purification of the expressed receptor.

Other modifications that have been used to improve upon the MBP fusion system has involved the generation of a triple-protein fusion construct (MBP-GPCR-TRX) that appears to further stabilize the receptor and improve expression and purification (Grisshammer & Tucker, 1997; Niebauer et al, 2006). Other factors influencing expression levels are the E. coli strain used and the growth temperature, codon optimisation, however expression is only the first stage in the purification pathway and further steps involving protein solubilisation, purification and renaturation are also required.

Other prokaryotic expression systems which can be utilised for the expression of GPCRs include *Haloferax volcanii* (Patenge & Soppa, 1999) and *Halobacterium salinarum* (Jaakola et al, 2005). Although, *Lactococcus lactis*, has been extensively used for the expression of a number of membrane proteins (Niu et al, 2008), no GPCRs have yet been reported to be expressed using this system.

The photosynthetic bacterium *Rhodobacter sphaeroides* has also been used for the production of human GPCRs whereby over-expression of recombinant receptors is placed under the control of the moderately strong and highly regulated super-operonic photosynthetic promoter pufQ and represents a scalable system (Roy et al, 2008).

Yeast Expression

Yeast systems contain a number of desirable attributes required for the high level expression of GPCRs needed for structural studies. Like E. coli, yeasts grow quickly and are easy and inexpensive to grow. They can be cultured to high cell densities and scale up can be achieved using fermentation technology. Furthermore, yeast expression systems allow for isotopic labeling and non-natural amino acid incorporation, both of which are important factors when considering an expression system for structural studies.

While yeast systems possess a number of the same benefits as do bacterial systems, they also have several advantages. Yeast, have compartmentalised organelles, allowing for more natural protein expression and folding, with subsequent insertion into the plasma membrane. Furthermore, unlike E. coli they can perform the majority of post-translational modifications, although glycosylation is substantially different to that observed in mammalian cells (Hamilton & Gerngross, 2007) there are examples of GPCRs that are not glycosylated in yeast (Sander et al, 1994).

However, the introduction of yeast strains engineered to provide a mammalian glycosylation profile may represent an improvement over the original expression strains. A number of different strains of yeast have been used for the over-expression of GPCRs including *Saccharomyces cerevisiae* (Huang et al, 2008), *Pichia pastori* (Feng et al, 2002) and *Schizosaccharomyces pombe* (Sander et al, 1994).

The process has been further simplified with the availability of a number of commercial expression systems, such as Invitrogen's *Pichia pastoris* system.

Insect Expression

To date, insect cell expression has provided the most commonly used expression system for the structural determination of GPCRs. The recent structural determination of the human $\beta_2$-adrenergic (Cherezov et al, 2007; Rasmussen et al, 2007) and $A_{2A}$ adenosine (Jaakola et al, 2008) receptors was achieved using *Spodoptera frugiperda* $Sf_9$ cells, whilst the structural determination of the turkey $\beta_1$AR (Warne et al, 2008) was achieved using *Trichoplusia ni* $Hi_5$ cells.

The relative success of insect cell expression, particularly in the structural biology of GPCRs, relates to their ability to generate multi-milligram quantities of high quality protein. A wide range of insect cells are commercially available including: *S. frugiperda* $Sf_9$, $Sf_{21}$, $Hi_5$ and *Drosophila* Schneider S2 cells, allowing screening of different cells to improve expression levels. The eukaryotic, baculovirus-based, expression system has been used for over 20 years, and relies on the viral transfection of insect cells to achieve protein production. Subsequently, a number of technological advances have resulted in the establishment of commercially available systems, which are more efficient and user friendly than the original system.

As with yeast expression, insect cell expression provides a platform in which most post-translational modifications required for functional protein can be achieved. In some cases, insect cell expression results in heterogeneous protein glycosylation, therefore, there has been considerable interest in the modification of insect cells, such as the Mimic™ $Sf_9$ insect cells, which have a more homogeneous human-like glycosylation machinery (Harrison & Jarvis, 2006).

Insect cells are typically grown at 27° C. and the types of lipid required to maintain membrane fluidity at this temperature are different to that of a native mammalian cell membrane. Insect cell membranes are very low in cholesterol and have no phosphatidyl serine in their plasma membranes.

In addition, they have comparatively high phosphatidyl inositol content and post-infection enrichment in phosphatidylcholine is observed (Marheineke et al, 1998). In GPCRs, an altered lipid environment can lead to modifications in ligand binding, as has been observed for the oxytocin receptor, due to heterogeneous expression of low-affinity and high-affinity receptors. The addition of cholesterol to the growth media results in a more homogeneous receptor population with a shift towards high-affinity ligand binding (Gimp) et al, 1995).

Scale up of protein production using relatively simple culture techniques can easily be accomplished in a biosafety level 1 laboratory environment (Ames et al, 2004). Insect cells are semi-adherent, allowing growth under attached conditions (rollers, micro-carriers) or in suspension.

Mammalian Expression

Mammalian cells have been used to express a wide range of GPCRs in different classes (Lundstrom et al, 2006). Mammalian cells have all the cellular machinery required to correctly translate, fold, modify and insert the protein into the cell membrane.

Heterologous protein production can be achieved through transient or stable expression and a wide variety of cell lines are available (e.g. CHO, HEK, COS-1 etc). Transient expression of GPCRs has been widely used for a number of years. Transiently transfected cells usually express protein through the cytomegalovirus (CMV) promoter after 48-72 hours post transfection, with a steady decrease thereafter.

This system provides a quick and relatively easy method of screening protein expression and allows for rapid site directed mutagenesis. Whilst lipid-based transfection methods have proved impractical for large-scale protein expression, other methods can be employed such as the use of recombinant virus (e.g. adenovirus) or Semliki Forest virus (SFV). To date, much of the work carried out on viral transfections has centered on the use of SFV which has a very high rate of success in the expression of GPCRs (Lundstrom et al, 2006).

Stably transected mammalian cell systems provide a constant source of recombinant protein. Like the transient transfection cell system, the gene of interest is placed under the control of a strong promoter such as the CMV promoter. The use of inducible promoters may be particularly advantageous with respect to membrane proteins as constitutive expression can potentially lead to cell toxicity (Reeves et al, 2002). In order to obtain a stable cell-line the expression construct is stably integrated into the host's cell genome; this typically requires the use of a selective marker (e.g. antibiotic resistance) as integration events are rare.

Advances in generating stable cell-lines have made this process simpler. For example, the lenti virus and the FLP-IN T-REX™ expression system which allows the generation of stable mammalian cell lines exhibiting tetracycline-inducible expression by placing a tetracycline-inducible promoter into the genome via Flp recombinase-mediated DNA recombination at the FRT site.

The use of GFP coupled with fluorescence-activated-cell sorting (FACS) allows the rapid selection of high protein expressers within mixed cell populations. The use of IRES-GFP technology has improved upon regular GFP-fusion selection by placing an internal ribosome entry site (IRES) downstream of the promoter and the coding sequence for the 'gene of interest', followed by the coding sequence for GFP. This allows for a single bicistronic messenger RNA encoding both genes to be produced. The two separate proteins are then translated from the same message, and their expression levels are thereby coupled. The use of IRES-GFP provides a monitor for the levels of target protein expression.

Additionally, mammalian cells, such as HEK293, are able to grow in suspension making them amenable to fermentation. Anchorage dependent cells can be grown in cell factories or on microcarrier beads.

Cell-Free Expression

Since the 1950s, in vitro transcription translation (IVT), has been successfully used to express soluble cytosolic protein and has recently been applied to the expression of more complex mammalian membrane proteins (Klammt et al, 2006). Advantages offered by cell-free (CF) protein expression include that the system does not depend on cellular integrity and does not require complex culture conditions. Although a number of CF systems exist, the three main sources are rabbit reticulocyte extract, wheat germ extract and *E. coli* extract.

CF expression systems are typically used in batch expression and the basic system contains all of the high molecular weight machinery required for transcription and translation. Modifications to the technology, whereby the cellular machinery is compartmentalised within a semi-permeable membrane to allow continuous feeding of low molecular weight precursors into the system, are known to increase both yield and rate of protein production.

Other Expression Systems

A number of other strategies for GPCR expression also have been investigated. One such strategy has been the use of whole organisms to express GPCRs. A wide range of organisms have been used to express GPCRs including *Xenopus oocytes* (eg, pituitary thyrotropin-releasing hormone receptor via mRNA microinjection Straub et al, 1990), *Drosophila melanogaster* (metabotropic glutamate receptor in photoreceptor cells Eroglu et al, 2002), transgenic silkworms (μ-opioid receptor Tateno et al, 2009) and other transgenic animals have also been used as a method to express GPCRs, such as adenovirus mediated expression of the chemokine receptor CXCR1 in transgenic mice.

*Chlamydomonas reinhardtii* chloroplasts are also used as protein factories (Mayfield et al, 2007) where there is a particular focus in the use of these cells for the production of protein-based therapeutics, such as (but not limited to) antibodies. Eukaryotic algae offer the potential to produce high yields of recombinant proteins more rapidly and at much lower cost than traditional cell culture. Additionally, transgenic algae can be grown in complete containment, reducing any risk of environmental contamination. This system might also be used for the oral delivery of therapeutic proteins or StaR vaccines, as green algae are edible, do not contain endotoxins or human viral or prion contaminants and are relatively cheap to produce merely requiring a source of water and sunlight (Dance, 2010)

Finally, manipulation of culture conditions also offers a route to improve expression levels. Optimisation of the culture conditions through the addition of additives such as ligands, amino acids, DMSO, and by altering temperature can increase expression by nearly 10-fold.

The question of yield relates both to the quantity and quality of protein produced. The gold standard for assessing the quality of protein is by measuring the ligand binding properties of the protein. Thus the $B_{max}$ values, which are relative measurements of specific activity expressed in moles of ligand bound to the protein divided by the amount of total protein, offer the best means to measure the quality of the protein.

Purification of the GPCR protein requires extraction of the protein of interest from the host cell/culture media. GPCR purification typically requires an initial cell-lysis step which in itself is governed by the type of expression system used. Due to the mechanical strength of their cell walls, both bacterial and yeast cells require a greater degree of force to achieve efficient cell lysis in comparison with insect and mammalian cells. In order to afford efficient cell lysis in bacteria and yeast, cells typically require the use of a French Press or a bead beater.

In contrast, mammalian and insect cells require much less mechanical force and can be lysed using fluidizers and freeze/thaw methods. When considering the method for lysis, care has to be paid to prevent denaturation of the GPCR through sheer force or thermal denaturation. Furthermore, the inclusion of protease inhibitors (e.g. pepstatin, leupeptin) to prevent proteolytic degradation of GPCRs upon lysis is of particular importance (Rosenbaum et al, 2007).

The large scale expression of GPCRs typically results in the generation of a large amount of biomass of which only a small percentage contains the protein of interest. The generation of membrane preparations offers an effective method to crudely purify the GPCR away from the majority of the cytosolic protein.

The most effective method to generate high quality membrane preparations is through the use of ultracentrifugation and stringent washing of the membrane preparation with high salt and acid/alkaline washes. The generation of high quality membrane preparation was exemplified in the recent structural determination of the human $A_{2A}$ structure, where the membrane preparation was washed up to 9 times with a high osmotic buffer containing 1.0 M NaCl; this subsequently facilitated a one step immobilised metal affinity chromatography (IMAC) purification (Jaakola et al, 2008).

As with the purification of all membrane proteins, GPCRs need to be extracted from the lipidic environment that they were expressed in, and subsequently solubilised into a surrogate detergent. The key to this step is establishing the critical solubilisation concentration (CSC), which is the minimal concentration of detergent required to disrupt the cell membrane into micellar dispersion. In addition, it is essential to use a detergent that does not inactivate the ligand binding properties of the receptor. It is assumed that if ligands can still bind to a detergent solubilised protein, then it is likely that the 3D structure is in a physiologically relevant state. A large and diverse range of detergents is available and can be classified into 3 main classes, namely non-ionic, zwitterionic and ionic.

As detergents and membrane proteins interact in an unpredictable manner, it is impossible to anticipate which is the most appropriate detergent to use in the purification process; this needs to be determined experimentally. However, within the 3 main classes of detergents previously described they can be sub-divided into detergents which are mild enough to maintain activity and structural integrity, and those that are harsh with a higher probability of protein denaturation.

When solubilising a receptor, detergent concentrations of 0.5-2% w/v are typically required, using detergent/protein ratios of 1:1 to 3:1. The concentration of the detergent is an important factor as detergent solubilised GPCRs and therefore StaRs will exist as protein detergent complexes (PDC). At low concentrations, detergents exist as monomers, and as the concentration increases above their CMC (critical micellar concentration) they form structures called micelles. The size and shape of micelles depend on the type, size, and stereochemistry of the detergent, as well as the aqueous environment that they occupy (ionic strength, pH, etc).

For the purification of all membrane proteins it is vital to maintain the concentration above the CMC, otherwise the micelle surrounding the membrane protein can disassemble leading to protein aggregation and inactivation. Whilst maintaining a level of detergent above the CMC is an important factor in protein stability, the addition of other agents can also dramatically enhance their stability.

Fortunately, the most widely used technique for purifying recombinant proteins, IMAC, performs well in most neutral detergents. Both nickel and cobalt matrices have been used for batch purification of GPCRs and StaRs with good success. However, it is noteworthy that the position of the His-tag (N- or C-terminal) can significantly affect the efficiency of binding to the resin. A number of other affinity chromatography techniques have also been investigated for the purification of GPCRs and are equally applicable to the purification of StaRs.

The use of other affinity tags such as strep and biotin tags have been used with varying degrees of success. Antibody affinity resins directed towards FLAG, TAP, and 1D4 tags have been explored. Lectin based chromatography (for example, wheat germ agglutinin, and heparin) can be used to purify GPCRs and is particularly useful where problems exist with respect to glycan heterogeneity. More classical techniques such as ion exchange (such as, Q-sepharose) and size exclusion chromatography (SEC) (such as, Superdex S200) can also be used, although the efficiency of protein separation by SEC is often poor in detergents with large micelles.

One of the most useful techniques in GPCR purification is the use of ligand affinity chromatography. Ligand affinity columns have been used for a number of years and have allowed GPCRs to be purified from native sources (Andre et al, 1983), a task that would ordinarily be particularly challenging due to their low natural abundance. Resins with covalently bound ligands such as XAC, ABT, and alprenolol have all been used to purify GPCRs. The major advantage of ligand affinity chromatography is that only functional receptors will bind to the resin. Therefore, the process is particularly useful for the purification of the conformationally biased StaR.

Mutants of a parent GPCR may therefore be produced in any suitable way and provided in any suitable form. Thus, for example, a series of specific mutants of the parent protein may be made in which each amino acid residue in all or a part of the parent protein is independently changed to another amino acid residue. For example, it may be convenient to make mutations in those parts of the protein which are predicted to be membrane spanning. The three-dimensional structure of rhodopsin is known (Li et al (2004) *J Mol Biol* 343, 1409-1438; Palczewski et al (2000) *Science* 289, 739-745), and it is possible to model certain GPCRs using this structure. Thus, conveniently, parts of the GPCR to mutate may be based on modelling. Similarly, computer programs are available which model transmembrane regions of GPCRs based on hydrophobicity (Kyle & Dolittle (1982) *J. Mol. Biol.* 157, 105-132), and use can be made of such models when selecting parts of the protein to mutate. Conventional site-directed mutagenesis may be employed, or polymerase chain reaction-based procedures well known in the art may be used. It is possible, but less desirable, to use ribosome display methods in the selection of the mutant protein.

Typically, each selected amino acid is replaced by Ala (ie Ala-scanning mutagenesis), although it may be replaced by any other amino acid. If the selected amino acid is Ala, it may conveniently be replaced by Leu. Alternatively, the amino acid may be replaced by Gly (ie Gly-scanning mutagenesis), which may allow a closer packing of neighbouring helices that may lock the protein in a particular conformation. If the selected amino acid is Gly, it may conveniently be replaced by Ala.

Although the amino acid used to replace the given amino acid at a particular position is typically a naturally occurring amino acid, typically an "encodeable" amino acid, it may be a non-natural amino acid (in which case the protein is typically made by chemical synthesis or by use of non-natural amino-acyl tRNAs). An "encodeable" amino acid is one which is incorporated into a polypeptide by translation of mRNA. It is also possible to create non-natural amino acids or introduce non-peptide linkages at a given position by covalent chemical modification, for example by post-translational treatment of the protein or semisynthesis. These post-translational modifications may be natural, such as phosphorylation, glycosylation or palmitoylation, or synthetic or biosynthetic.

Alternatively, mutants may be produced by a random mutagenesis procedure, which may be of the whole protein or of a selected portion thereof. Random mutagenesis procedures are well known in the art.

Conveniently, a mutant GPCR has one replaced amino acid compared to the parent protein (ie it is mutated at one amino acid position). In this way, the contribution to stability of a single amino acid replacement may be assessed. However, the mutant GPCR assayed for stability may have more than one replaced amino acid compared to the parent protein, such as 2 or 3 or 4 or 5 or 6 replacements.

Combinations of mutations in one GPCR may be appropriate such that multiple different mutations in a single mutant protein can lead to further stability. Thus, it will be appreciated that the method of selection can be used in an iterative way by, for example, carrying it out to identify single mutations which increase stability, combining those mutations in a single mutant GPCRs which is the GPCR then provided in part (a) of the method. Thus, multiple-mutated mutant proteins can be selected using the method.

A GPCR of the invention or parent GPCR from which a mutant is derived need not be the naturally occurring protein. Conveniently, it may be an engineered version which is capable of expression in a suitable host organism, such as *Escherichia coli*. For example, as described in WO 2009/081136, a convenient engineered version of the turkey β-adrenergic receptor is one which is truncated and lacks residues 1-33 of the amino acid sequence (ie $\beta AR_{34-424}$). The parent GPCR may be a truncated form of the naturally occurring protein (truncated at either or both ends), or it may be a fusion, either to the naturally occurring protein or to a fragment thereof. Alternatively or additionally, the parent GPCR, compared to a naturally-occurring GPCR, may be modified in order to improve, for example, solubility, proteolytic stability (eg by truncation, deletion of loops, mutation of glycosylation sites or mutation of reactive amino acid side chains such as cysteine). In any event, the parent GPCR is a protein that is able to bind to the selected ligand which ligand is one which is known to bind the naturally occurring GPCR. Conveniently, the parent GPCR is one which, on addition of an appropriate ligand, can affect any one or more of the downstream activities which are commonly known to be affected by G-protein activation.

It will be appreciated that the stability of a GPCR mutant is to be compared to a parent GPCR in order to be able to assess an increase in stability.

Increased stability of a mutant GPCR by comparison to a parent GPCR is conveniently measured by an extended lifetime of the mutant under the imposed conditions which may lead to instability (such as heat, harsh detergent conditions, chaotropic agents and so on). Destabilisation under the imposed condition is typically determined by measuring denaturation or loss of structure. This may manifest itself by loss of ligand binding ability or loss of secondary or tertiary structure indicators.

Typically, the mutant GPCR binds to a ligand (selected binding partner) with approximately equal affinity (that is to say typically within 2-3 fold) or greater affinity than does the parent receptor, when residing in the same conformation. For agonist-conformation mutants, the mutants typically bind the agonist-conformation specific binding partners with the same or higher affinity than the parent GPCR and typically bind antagonist-conformation specific binding partners with the same or lower affinity than the parent GPCR. Similarly for antagonist-conformation mutants, the mutants typically bind the antagonist-conformation specific binding partners with the same or higher affinity than the parent GPCR and typically bind agonist-conformation specific binding partners with the same or lower affinity than the parent GPCR.

Comparison of parent and mutant GPCRs can be conducted using binding assays well known in the art and as described, for example, below. Typically, $K_d$ values are calculated using conventional GPCR assays in membranes wherein the binding affinity at different compound concentrations is measured. Examples of suitable assays include surface plasmon resonance assays and competition assays which are well known in the art and are described below.

In one example of a testing procedure the mutant GPCR may be brought into contact with a ligand before being subjected to a procedure in which the stability of the mutant is determined (the mutant GPCR and ligand remaining in contact during the test period). Thus, for example, when the method is being used to select for mutant GPCRs which in one conformation bind to a ligand and which have improved thermostability, the receptor is contacted with the ligand before being heated, and then the amount of ligand bound to the receptor following heating may be used to express thermostability compared to the parent receptor. This provides a measure of the amount of the GPCR which retains ligand binding capacity following exposure to the denaturing conditions (eg heat), which in turn is an indicator of stability.

In order to experimentally determine a Kd then, the concentration of free ligand and bound ligand at equilibrium must be known. Typically, this can be done by using a radio-labelled or fluorescently labelled ligand which is incubated with the receptor (present in whole cells or homogenised membranes) until equilibrium is reached. The amount of free ligand vs bound ligand must then be determined by separating the signal from bound vs free ligand. In the case of a radioligand this can be done by centrifugation or filtration to separate bound ligand present on whole cells or membranes from free ligand in solution. Alternatively a scintillation proximity assay is used. In this assay the receptor (in membranes) is bound to a bead containing scintillant and a signal is only detected by the proximity of the radioligand bound to the receptor immobilised on the bead.

The affinity constant may also be determined in a functional assay ($K_s$). Here the receptor in a whole cell or membrane is activated by an agonist ligand and a response measured (e.g. mobilisation of intracellular calcium, G protein activation, increase or decrease in adenylate cyclise or cAMP, activation of a signal transduction pathway such as a MAP-kinase pathway or activation of gene transcription). The ability of an antagonist to inhibit agonist activity can be measured and for a competitive antagonist is equal to the affinity constant.

In an alternative example of a testing procedure, the mutant GPCR is subjected to a procedure in which the stability of the mutant is determined before being contacted with the ligand. Thus, for example, when the method is being used to select for mutant membrane receptors which in one conformation bind to a ligand and which have improved thermostability, the receptor is heated first, before being contacted with the ligand, and then the amount of ligand bound to the receptor may be used to express thermostability. Again, this provides a measure of the amount of the GPCR which retains ligand binding capacity following exposure to the denaturing conditions.

In both tests, it will be appreciated that the comparison of stability of the mutant is made by reference to the parent molecule under the same conditions.

It will be appreciated that in both of these tests, the mutants that are selected are ones which have increased stability when residing in the particular conformation compared to the parent protein.

A mutant GPCR may be selected which has increased stability to any denaturant or denaturing condition such as to any one or more of heat, a detergent, a chaotropic agent or an extreme of pH.

In relation to an increased stability to heat (ie thermostability), this can readily be determined by measuring ligand binding or by using spectroscopic methods such as fluorescence, CD or light scattering at a particular temperature. Typically, when the GPCR binds to a ligand, the ability of the GPCR to bind that ligand at a particular temperature may be used to determine thermostability of the mutant. It may be convenient to determine a "quasi $T_m$" ie the temperature at which 50% of the receptor is inactivated under stated conditions after incubation for a given period of time (eg 30 minutes). Mutant GPCRs of higher thermostability have an increased quasi Tm compared to their parents.

In relation to an increased stability to a detergent or to a chaotrope, typically the GPCR is incubated for a defined time in the presence of a test detergent or a test chaotropic agent and the stability is determined using, for example, ligand binding.

In relation to an extreme of pH, a typical test pH would be chosen (eg in the range 4.5 to 5.5 (low pH) or in the range 8.5 to 9.5 (high pH)).

Because relatively harsh detergents are used during crystallisation procedures, it is preferred that the mutant GPCR is stable in the presence of such detergents. The order of "harshness" of certain detergents is DDM, $C_{11} \rightarrow C_{10} \rightarrow C_9 \rightarrow C_8$ maltoside or glucoside, lauryldimethylamine oxide (LDAO) and SDS. It is particularly preferred if the mutant GPCR is more stable to any of $C_9$ maltoside or glucoside, $C_8$ maltoside or glucoside, LDAO and SDS, and so it is preferred that these detergents are used for stability testing.

Because of its ease of determination, it is preferred that thermostability is determined, and those mutants which have an increased thermostability compared to the parent protein with respect to the selected condition are chosen. It will be appreciated that heat is acting as the denaturant, and this can readily be removed by cooling the sample, for example by placing on ice. It is believed that thermostability may also be a guide to the stability to other denaturants or denaturing conditions. Thus, increased thermostability is likely to translate into stability in denaturing detergents, especially those that are more denaturing than DDM, eg those detergents with a smaller head group and a shorter alkyl chain and/or with a charged head group. We have found that a thermostable GPCR is also more stable towards harsh detergents.

When an extreme of pH is used as the denaturing condition, it will be appreciated that this can be removed quickly by adding a neutralising agent. Similarly, when a chaotrope is used as a denaturant, the denaturing effect can be removed by diluting the sample below the concentration in which the chaotrope exerts its chaotropic effect.

The mutant GPCRs may be prepared by any suitable method. Conveniently, the mutant protein is encoded by a suitable nucleic acid molecule and expressed in a suitable host cell. Suitable nucleic acid molecules encoding the mutant GPCR may be made using standard cloning techniques, site-directed mutagenesis and PCR as is well known in the art. Suitable expression systems include constitutive or inducible expression systems in bacteria or yeasts, virus expression systems such as baculovirus, semliki forest virus and lentiviruses, or transient transfection in insect or mammalian cells. Suitable host cells include *E. coli, Lactococcus lactis, Saccharomyces cerevisiae, Schizosaccharomyces pombe, Pichia pastoris, Spodoptera frugiperda* and *Trichoplusiani* cells. Suitable animal host cells include HEK 293, COS, S2, CHO, NSO, DT40 and so on. It is known that some GPCRs require specific lipids (eg cholesterol) to function. In that case, it is desirable to select a host cell which contains the lipid. Additionally or alternatively the lipid may be added during isolation and purification of the mutant protein. It will be appreciated that these expression systems and host cells may also be used in the provision of the mutant GPCR in part (a) of the selection method.

Molecular biological methods for cloning and engineering genes and cDNAs, for mutating DNA, and for expressing polypeptides from polynucleotides in host cells are well known in the art, as exemplified in "Molecular cloning, a laboratory manual", third edition, Sambrook, J. & Russell, D. W. (eds), Cold Spring Harbor Laboratory Press, Cold Spring Harbor, N.Y., incorporated herein by reference.

It is appreciated that it may be determined whether the selected or prepared mutant GPCR is able to couple to a G protein. It is also preferred if it is determined whether the selected or prepared mutant GPCR is able to bind a plurality of ligands of the same class as the selecting ligand with a comparable spread and/or rank order of affinity as the parent GPCR.

By "corresponding position or positions", we include the meaning of the position in the amino acid sequence of a second GPCR which aligns to the position in the amino acid sequence of the first GPCR, when the first and second GPCRs are compared by alignment, for example by using MacVector and Clustal W.

Having identified the corresponding position or positions in the amino acid sequence of a second GPCR, the amino acids at those positions are replaced with another amino acid. Typically, the amino acids are replaced with the same amino acids which replaced the amino acids at the corresponding positions in the mutant of the first parent GPCR (unless they are already that residue).

Mutations can be made in an amino acid sequence, for example, as described above and using techniques well-established in the art.

For the avoidance of doubt, the mutant GPCR may be extended or truncated, contain internal deletions or insertions or otherwise altered beyond introduction of stabilising mutations; for example by introduction or deletion of sites for posttranslational modification e.g. glycosylation or phosphorylation or fatty acylation. It may also be chemically modified synthetically, for example by peptide semisynthesis or crosslinking or alkylation. In any event, the mutant GPCR provided has increased stability in a particular conformation relative to its parent GPCR.

Preferably the GPCR is a mammalian GPCR. Conveniently, the GPCR is a human, mouse, rat or turkey GPCR.

Advantageously the GPCR of the invention is one selected from chemokine receptor 4 (CXCR4), chemokine receptor 2 (CCR2), Duffy antigen receptor for chemokines (DARC), angiotensin receptor, β1-adrenergic receptor (β1-AR), adenosine receptor, muscarinic receptor and neurotensin receptor (NTS1).

β-Adrenergic Receptor

β-adrenergic receptors are well known in the art. They share sequence homology to each other and bind to adrenalin.

In one embodiment, the GPCR is a wildtype or a mutant β-adrenergic receptor. The mutant β-adrenergic receptor when compared to the corresponding wild-type β-adrenergic receptor, has a different amino acid at a position which corresponds to any one or more of the following positions according to the numbering of the turkey β-adrenergic receptor as set out in FIG. 1: Ile 55, Gly 67, Arg 68, Val 89, Met 90, Gly 98, Ile 129, Ser 151, Val 160, Gln 194, Gly 197, Leu 221, Tyr 227, Arg 229, Val 230, Ala 234, Ala 282, Asp 322, Phe 327, Ala 334, Phe 338.

The mutant β-adrenergic receptor may be a mutant of any β-adrenergic receptor provided that it is mutated at one or more of the amino acid positions as stated by reference to the given turkey β-adrenergic receptor amino acid sequence.

It is particularly preferred if the mutant GPCR is one which has at least 20% amino acid sequence identity when compared to the given turkey β-adrenergic receptor sequence, as determined using MacVector and CLUSTALW (Thompson et al (1994) *Nucl. Acids Res.* 22, 4673-4680). More preferably, the mutant receptor has at least 30% or at least 40% or at least 50% amino acid sequence identity. There is generally a higher degree of amino acid sequence identity which is conserved around the orthosteric ("active") site to which the natural ligand binds.

Thus, a mutant turkey β-adrenergic receptor in which, compared to its parent, one or more of these amino acid residues have been replaced by another amino acid residue may be used. Mutant β-adrenergic receptors from other sources in which one or more corresponding amino acids in the parent receptor are replaced by another amino acid residue may also be used.

For the avoidance of doubt, the parent may be a β-adrenergic receptor which has a naturally-occurring sequence, or it may be a truncated form or it may be a fusion, either to the naturally occurring protein or to a fragment thereof, or it may contain mutations compared to the naturally-occurring sequenced provided that it retains ligand-binding ability.

By "corresponding amino acid residue" we include the meaning of the amino acid residue in another β-adrenergic receptor which aligns to the given amino acid residue in turkey β-adrenergic receptor when the turkey β-adrenergic receptor and the other β-adrenergic receptor are compared using MacVector and CLUSTALW.

FIG. 1 shows an alignment between turkey β-adrenergic receptor and human β1, β2 and β3 β-adrenergic receptors.

It can be seen that Ile 72 of human β1 corresponds to Ile 55 of turkey β-adrenergic receptor; Ile 47 of human β2 corresponds to Ile 55 of turkey β-adrenergic receptor; and Thr51 of human β3 corresponds to Ile 55 of turkey β-adrenergic receptor. Other corresponding amino acid residues in human β1, β2 and β3 can readily be identified by reference to FIG. 1.

It is preferred if the mutant β-adrenergic receptor has a different amino acid compared to its parent at more than one amino acid position since this is likely to give greater stability. Particularly preferred human β1 receptor mutants are those in which one or more of the following amino acid residues are replaced with another amino acid residue: K85, M107, Y244, A316, F361 and F372. Typically, the given amino acid residue is replaced with Ala or Val or Met or Leu or Ile (unless they are already that residue).

Mutant human β1 receptors which have combinations of 3 or 4 or 5 or 6 mutations as described above are preferred.

Particularly preferred human β2 receptor mutants are those in which one or more of the following amino acids are replaced with another amino acid residue: K60, M82, Y219, C265, L310 and F321. Typically, the given amino acid residue is replaced with Ala or Val or Met or Leu or Ile (unless they are already that residue).

Adenosine Receptor

Adenosine receptors are well known in the art. They share sequence homology to each other and bind to adenosine.

In one embodiment, the GPCR is a wildtype or mutant adenosine receptor. The mutant adenosine receptor when compared to the corresponding wild-type adenosine, has a different amino acid at a position which corresponds to any one or more of the following positions according to the numbering of the human adenosine $A_{2a}$ receptor as set out in FIG. 2: Gly 114, Gly 118, Leu 167, Ala 184, Arg 199, Ala 203, Leu 208, Gln 210, Ser 213, Glu 219, Arg 220, Ser 223, Thr 224, Gln 226, Lys 227, His 230, Leu 241, Pro 260, Ser 263, Leu 267, Leu 272, Thr 279, Asn 284, Gln 311, Pro 313, Lys 315, Ala 54, Val 57, His 75, Thr 88, Gly 114, Gly 118, Thr 119, Lys 122, Gly 123, Pro 149, Glu 151, Gly 152, Ala 203, Ala 204, Ala 231, Leu 235, Val 239.

The mutant adenosine receptor may be a mutant of any adenosine receptor provided that it is mutated at one or more of the amino acid positions as stated by reference to the given human adenosine $A_{2a}$ receptor amino acid sequence.

It is particularly preferred if the mutant GPCR is one which has at least 20% amino acid sequence identity when compared to the given human adenosine $A_{2a}$ receptor sequence, as determined using MacVector and CLUSTALW.

Preferably, the mutant GPCR has at least 30% or at least 40% or at least 50% or at least 60% sequence identity. Typically, there is a higher degree of sequence conservation at the adenosine binding site.

Thus, a mutant human adenosine $A_{2a}$ receptor in which, compared to its parent, one or more of these amino acid residues have been replaced by another amino acid residue may be used. Mutant adenosine receptors from other sources in which one or more corresponding amino acids in the parent receptor are replaced by another amino acid residue may also be used.

For the avoidance of doubt, the parent may be an adenosine receptor which has a naturally-occurring sequence, or it may be a truncated form or it may be a fusion, either to the naturally-occurring protein or to a fragment thereof, or it may contain mutations compared to the naturally-occurring sequence, provided that it retains ligand-binding ability.

By "corresponding amino acid residue" we include the meaning of the amino acid residue in another adenosine receptor which aligns to the given amino acid residue in human adenosine $A_{2a}$ receptor when the human adenosine $A_{2a}$ receptor and the other adenosine receptor are compared using MacVector and CLUSTALW.

FIG. 2 shows an alignment between human adenosine $A_{2a}$ receptor and three other human adenosine receptors (A2b, A3 and A1).

It can be seen that, for example, Ser 115 in the $A_{2b}$ receptor (indicated as AA2BR) corresponds to Gly 114 in the $A_{2a}$ receptor. Similarly, it can be seen that Ala 60 in the $A_3$ receptor (indicated as AA3R) corresponds to Ala 54 in the $A_{2a}$ receptor, and so on. Other corresponding amino acid residues in human adenosine receptors $A_{2b}$, $A_3$ and $A_1$ can readily be identified by reference to FIG. 2.

It is preferred that the particular amino acid in the parent is replaced with an Ala. However, when the particular amino acid residue in the parent is an Ala, it is preferred that it is replaced with a Leu.

It is preferred that the mutant adenosine receptor has a different amino acid compared to its parent at more than one amino acid position. Particularly preferred human adenosine A2b receptors are those in which one or more of the following amino acid residues are replaced with another amino acid residue: A55, T89, R123, L236 and V240. Typically, the given amino acid residue is replaced with Ala or Val or Met or Leu or Ile (unless they are already that residue).

Mutant human adenosine receptors which have combinations of 3 or 4 or 5 mutations as described above are preferred.

Particularly preferred human adenosine A3 receptors are those in which one or more of the following amino acid residues are replaced with another amino acid residue: A60, T94, W128, L232 and L236. Typically, the given amino acid residue is replaced with Ala or Val or Met or Leu or Ile (unless they are already that residue).

Neurotensin Receptor

Neurotensin receptors are known in the art. They share sequence homology and bind neurotensin.

In one embodiment, the GPCR is a wildtype or mutant neurotensin receptor. The mutant neurotensin receptor when compared to the corresponding wild-type neurotensin receptor, has a different amino acid at a position which corresponds to any one or more of the following positions according to the numbering of the rat neurotensin receptor as set out in FIG. 3: Ala 69, Leu 72, Ala 73, Ala 86, Ala 90, Ser 100, His 103, Ser 108, Leu 109, Leu 111, Asp 113, Ile 116, Ala 120, Asp 139, Phe 147, Ala 155, Val 165, Glu 166, Lys 176, Ala 177, Thr 179, Met 181, Ser 182, Arg 183, Phe 189, Leu 205, Thr 207, Gly 209, Gly 215, Val 229, Met 250, Ile 253, Leu 256, Ile 260, Asn 262, Val 268, Asn 270, Thr 279, Met 293, Thr 294, Gly 306, Leu 308, Val 309, Leu 310, Val 313, Phe 342, Asp 345, Tyr 349, Tyr 351, Ala 356, Phe 358, Val 360, Ser 362, Asn 370, Ser 373, Phe 380, Ala 385, Cys 386, Pro 389, Gly 390, Trp 391, Arg 392, His 393, Arg 395, Lys 397, Pro 399.

It is particularly preferred if the mutant GPCR is one which has at least 20% amino acid sequence identity when compared to the given rat neurotensin receptor sequence, as determined using MacVector and CLUSTALW. Preferably, the mutant GPCR has at least 30% or at least 40% or at least 50% amino acid sequence identity.

The mutant neurotensin receptor may be a mutant of any neurotensin receptor provided that it is mutated at one or more of the amino acid positions as stated by reference to the given rat neurotensin receptor amino acid sequence.

Thus, a mutant rat neurotensin receptor in which, compared to its parent, one or more of these amino acid residues have been replaced by another amino acid residue may be used. Mutant neurotensin receptors from other sources in which one or more corresponding amino acids in the parent receptor are replaced by another amino acid residue may also be used.

For the avoidance of doubt the parent may be a neurotensin receptor which has a naturally-occurring sequence, or it may be a truncated form or it may be a fusion, either to the naturally-occurring protein or to a fragment thereof, or it may contain mutations compared to the naturally-occurring sequence, providing that it retains ligand-binding ability.

By "corresponding amino acid residue" we include the meaning of the amino acid residue in another neurotensin receptor which aligns to the given amino acid residue in rat neurotensin receptor when the rat neurotensin receptor and the other neurotensin receptor are compared using MacVector and CLUSTALW.

FIG. 3 shows an alignment between rat neurotensin receptor and two human neurotensin receptors 1 and 2. It can be seen, for example, that Ala 85 of the human neurotensin receptor 1 corresponds to Ala 86 of the rat neurotensin receptor, that Phe 353 of the human neurotensin receptor 1 corresponds to Phe 358 of the rat neurotensin receptor, and so on. Other corresponding amino acid residue in the human neurotensin receptors 1 and 2 can readily be identified by reference to FIG. 3.

It is preferred that the particular amino acid in the parent is replaced with an Ala. However, when the particular amino acid residue in the parent is an Ala, it is preferred that it is replaced with a Leu.

It is preferred that the mutant neurotensin receptor has a different amino acid compared to its parent at more than one amino acid position. Particularly preferred human neurotensin receptors (NTR1) are those in which one or more of the following amino acid residues are replaced with another amino acid residue: Ala 85, His 102, Ile 259, Phe 337 and Phe 353. Typically, the given amino acid residues is replaced with Ala or Val or Met or Leu or Ile (unless they are already that residue).

Mutant neurotensin receptors which have combinations of 3 or 4 or 5 mutations as described above are preferred.

Muscarinic Receptor

Muscarinic receptors are known in the art. They share sequence homology and bind muscarine.

In one embodiment, the GPCR is a wildtype or mutant muscarinic receptor. The mutant muscarinic receptor when compared to the corresponding wild-type muscarinic receptor, has a different amino acid at a position which corresponds to any one or more of the following positions according to the numbering of the human muscarinic receptor M1 as set out in FIG. 4: Leu 65, Met 145, Leu 399, Ile 383 and Met 384.

It is particularly preferred if the mutant GPCR is one which has at least 20% amino acid sequence identity when compared to the given human muscarinic receptor sequence, as determined using MacVector and CLUSTALW. Preferably, the mutant GPCR has at least 30% or at least 40% or at least 50% amino acid sequence identity.

The mutant muscarinic receptor may be a mutant of any muscarinic receptor provided that it is mutated at one or more of the amino acid positions as stated by reference to the given muscarinic receptor amino acid sequence.

Thus, a mutant human muscarinic receptor in which, compared to its parent, one or more of these amino acid residues have been replaced by another amino acid residue may be used. Mutant muscarinic receptors from other sources in which one or more corresponding amino acids in the parent receptor are replaced by another amino acid residue may also be used.

For the avoidance of doubt the parent may be a muscarinic receptor which has a naturally-occurring sequence, or it may be a truncated form or it may be a fusion, either to the naturally-occurring protein or to a fragment thereof, or it may contain mutations compared to the naturally-occurring sequence, providing that it retains ligand-binding ability.

By "corresponding amino acid residue" we include the meaning of the amino acid residue in another muscarinic receptor which aligns to the given amino acid residue in human muscarinic receptor when the human muscarinic receptor and the other muscarinic receptor are compared using MacVector and CLUSTALW.

It is preferred that the particular amino acid is replaced with an Ala. However, when the particular amino acid residue is an Ala, it is preferred that it is replaced with a Leu.

Therapeutic Applications of GPCR Vaccines

GPCR vaccine targets have the potential to be of therapeutic benefit in a number of disease areas, such as cancer vaccines, e.g., CXCR4 is involved in metastasis; Kaposi's sarcoma-associated herpes virus GPCR (KSHv-GPCR aka ORF74), Epstein Barr virus-encoded BILF1 and Cytomegalovirus (CMV) are all indicated in cancers; infectious diseases, specifically the inhibition of viral entry, for example, CXCR4 in HIV, CCR2 and herpes simplex virus, the Duffy antigen receptor for chemokines (DARC) and the malarial parasite responsible for recurring malaria, *Plasmodium vivax*; and cardiovascular indications, such as Angiotensin receptor in hypertension and CXCR4 in WHIM syndrome.

In relation to a preferred example of the use of GPCR vaccines against cancer, CXCR4 is known to be involved in metastasis, where numerous studies have demonstrated the role of the SDF-1 (CXCL12)/CXCR4 axis in metastasis. For example, SDF-1 has been shown to be highly expressed in common metastatic locations, such as lymph nodes, bone marrow, lung and liver, and CXCR4 highly expressed on the cell surface of several tumour cells, eg, breast cancer cells (Müller et al, 2004). In addition, this axis plays an important and unique role in the regulation of stem/progenitor cell trafficking. SDF-1 regulates the trafficking of CXCR4$^+$ haemato/lymphopoietic cells, their homing/retention in major haemato/lymphopoietic organs and accumulation of CXCR4$^+$ immune cells in tissues affected by inflammation. In addition, CXCR4 plays an essential role in the trafficking of other tissue/organ specific stem/progenitor cells expressing CXCR4 on their surface, e.g., during embryo/organogenesis and tissue/organ regeneration. The SDF-1/CXCR4 axis also plays an important role in tumour vascularization (Ingold et al 2010). This suggests that new therapeutic strategies aimed at blocking the SDF-1-CXCR4 axis could have important applications in the clinic by modulating the trafficking of haemato/lymphopoietic cells and inhibiting the metastatic behaviour of tumour cells by the use of antagonists (Tsutsumi et al, 2007). Hence, a CXCR4 StaR vaccine could not only be utilised to block SDF-1/CXCR4 interaction thereby preventing metastasis, but also employed to mobilize a cancer patient's stem cells from the bone marrow to the periphery. Precedence for stem cell mobilisation has been provided by the use of Plerixafor (Mobozil), a bicyclam derivative, in conjunction with G-CSF for haematopoietic stem cell mobilisation in patients with lymphoma or multiple myeloma.

In an alternative embodiment the GPCR is a virally encoded GPCR. Preferably the GPCR is a GPCR encoded by any of Epstein Barr virus, cytomegalovirus, Kaposi's sarcoma-associated herpes virus, herpes simplex virus, and human immunodeficiency virus. When the GPCR is a GPCR of Kaposi's sarcoma-associated herpes virus the GPCR is preferably a full length GPCR and not an antigenic fragment thereof. It is also preferred that the GPCR is provided in an isolated form removed from membrane associated proteins and other membrane components such as lipoproteins, apolipoproteins, lipids, phosphoinositol lipids and liposaccharides.

In one embodiment, the GPCR is not provided in a lipoparticle.

Virally encoded GPCR targets implicated in cancer include:—

Kaposi's sarcoma-associated herpes virus GPCR (KSHv-GPCR aka ORF74) where KSHv-GPCR is a homologue of the human IL-8 receptor that signals constitutively, activates mitogen- and stress-activated kinases, and induces transcription via multiple transcription factors including AP-1 and NFKB. Furthermore, vGPCR causes cellular transformation in vitro and leads to KS-like tumors in transgenic mouse models. vGPCR has therefore become an exciting potential therapeutic target for KSHV-mediated disease (Cannon et al, 2004);

Epstein Barr virus-encoded BILF1, which is a member of a new family of related GPCRs exclusively encoded by γ1-herpesviruses. Immunocytochemistry and confocal microscopy reveals that BILF1 localizes predominantly to the plasma membrane, similar to the localisation of KSHV ORF74. Human and rhesus EBV-encoded BILF1 are highly potent constitutively active receptors, activating $G_{\alpha_i}$.

Furthermore, BILF1 is able to inhibit forskolin-triggered CREB activation via stimulation of endogenous G proteins in a pertussis toxin-sensitive manner, verifying that BILF1 signals constitutively through $G_{\alpha_i}$. It is thought that EBV may use BILF1 to regulate $G_{\alpha_i}$-activated pathways during viral lytic replication, thereby affecting disease progression (Paulsen et al, 2005);

Cytomegalovirus (CMV) encoded US28 binds CC chemokines. Cytomegalovirus (CMV), a beta herpes virus, is a widespread pathogen responsible for generally asymptomatic and persistent infections in healthy people. It may, however, cause severe disease in the absence of an effective immune response, as in immunologically immature and immunocompromised individuals (Lembo et al, 2004). Human CMV has been implicated in the etiology of several human cancers, in particular, cervical carcinoma and adenocarcinomas of the prostate and colon (Doniger et al, 1999). CMV has also been suggested to play a role in athlerosclerosis (Smit et al, 2003) where US28 is able to induce migration of smooth muscle cells, a feature essential for the development of this condition;

CCR5 and CXCR4GPCRs are involved in HIV. CXCR4 tropic virus is found in HIV patients, comprising <15% of virus in treatment-naive patients (Dau and Holodniy, 2009). Its clinical utility as a target for HIV was initially demonstrated by human genetics. Around 1-3% of Caucasian individuals (Samson et al, 1996) lack CCR5 expression, due to a deletion in the CCR5 gene. This has little effect on normal immune function however this population is highly protected against HIV infection.

CCR2 and herpes simplex virus where activation of chemokine expression and the role of CCR2 has been implicated in HSV biology and pathogenesis (Cook et al, 2004).

In another embodiment an important target for the GPCR vaccines of the invention is the Duffy antigen receptor for chemokines (DARC) and the malarial parasite responsible for recurring malaria, *Plasmodium vivax*. Although this is less virulent than *P. falciparum*, it is the most frequent and widely distributed cause of tertian malaria, frequently causes a severe complicated and long lasting illness and occasionally causing death through splenomegaly. 2.6 billion people in countries across Asia and South America live in areas endemic for *P. vivax* and there are around 50-70 million clinical episodes each year (Guerra et al, 2006; Mendis et al, 2001).

Treatment of malaria is usually the administration of chloroquine, however resistant forms of malaria to this drug are emerging, eg, Korea; artesunate is not approved for use in the US; atovaquone-proguanil is an alternative for patients unable to tolerate chloroquine. Quinine can be used for treatment but has an inferior outcome and primaquine is used for eradication of the liver stages, but requires a check on G6PD status to reduce the risk of haemolysis in the patient.

The Duffy blood group proteins Fya and Fyb act as receptors on erythrocytes for invasion by *P. vivax* (and *P. knowlesi*). Interaction with DARC is mediated by *P vivax* Duffy binding protein (PvDBP) and essential for junction formation—a key step in the invasion process by the merozoite parasite. Duffy negative individuals (which include the majority of individuals from Africa) are naturally highly resistant to this parasite (Tournamille et al, 1995). The receptor binding region of PvDBP is a conserved cysteine-rich region, known as PvRII. DARC-PvRII is the receptor/ligand interaction. Targeting the blood stage of this parasite has several advantages in that it is during these stages that disease/illness occurs. Therapies directed at the initial liver stage of infection could prevent infection per se however this is likely to be challenging to achieve. Therapies directed at the blood stages during which replication occurs are likely to be effective at preventing illness and complications as is found with the natural DARC deletions. Using the antagonist conformation of DARC as a vaccine could stimulate the production of naturally occurring antibodies blocking the DARC-PvRII interaction and subsequent infection.

Other medical conditions where a StaR vaccine would be of therapeutic benefit are exemplified by cardiovascular indications, such as Angiotensin receptor in hypertension and CXCR4 in WHIM syndrome where heterozygous mutations and truncations of the receptor's C terminus causes a congenital immunodeficiency disorder (McGuire et al 2010). Truncation of the receptor protein results in the inability of downregulation after stimulation. Thus, the receptor remains in an activated state (Lagane et al, 2008).

Exemplary GPCR Vaccine Compositions and Modes of Administration

The GPCRs and polynucleotides of the present invention may be delivered using an injectable sustained-release drug delivery system. These are designed specifically to reduce the frequency of injections. An example of such a system is Nutropin Depot which encapsulates recombinant human growth hormone (rhGH) in biodegradable microspheres that, once injected, release rhGH slowly over a sustained period.

The GPCR proteins and GPCR encoding polynucleotides of the present invention can be administered by a surgically implanted device that releases the drug directly to the required site. For example, Vitrasert releases ganciclovir directly into the eye to treat CMV retinitis. The direct application of this toxic agent to the site of disease achieves effective therapy without the drug's significant systemic side-effects.

Electroporation therapy (EPT) systems can also be employed for administration. A device which delivers a pulsed electric field to cells increases the permeability of the cell membranes to the drug, resulting in a significant enhancement of intracellular drug delivery.

GPCR proteins and GPCR-encoding polynucleotides of the invention can also be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of administration is the ReGel injectable system that is thermosensitive. Below body temperature, ReGel is an injectable liquid while at body temperature it immediately forms a gel reservoir that slowly erodes and dissolves into known, safe, biodegradable polymers. The active drug is delivered over time as the biopolymers dissolve.

Preferably, the pharmaceutical formulation of the present invention is a unit dosage containing a daily dose or unit, daily sub-dose or an appropriate fraction thereof, of the active ingredient.

The vaccine compositions of the invention can be administered by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the vaccine compositions of the invention can be administered alone but will generally be administered in admixture with a suitable pharmaceutical excipient diluent or carrier selected with regard to the intended route of administration and standard pharmaceutical practice.

The vaccine compositions of the invention can also be administered parenterally, for example, intravenously, intra-arterially, intraperitoneally, intra-thecally, intraventricularly, intrasternally, intracranially, intra-muscularly, intra-nasally, or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Generally, in humans, oral or parenteral administration is the preferred route, being the most convenient.

For veterinary use, the vaccine compositions of the invention are administered as a suitably acceptable formulation in accordance with normal veterinary practice and the veterinary surgeon will determine the dosing regimen and route of administration which will be most appropriate for a particular animal.

Preferred administration routes are: for either DNA or protein, intradermal, intramuscular or sub-cutaneous using a needleless device. Dosages will be in the range of:

DNA ranges are 100 µg to 6 milligrams (VGX-3100 for CIN2 and CIN3 surgically-treated patients)

Protein ranges from 100 µg to 3 milligrams (eg, DCVax).

The formulations of the vaccine compositions of the invention may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Preferred unit dosage formulations are those containing a daily dose or unit, daily sub-dose or an appropriate fraction thereof, of an active ingredient.

It should be understood that in addition to the ingredients particularly mentioned above the formulations of this invention may include other agents conventional in the art having regard to the type of formulation in question.

Advantageously, a GPCR protein and GPCR-encoding polynucleotide of the invention is administered alone. However it may also be presented as a pharmaceutical formulation, together with one or more acceptable carriers. The carrier(s) must be "acceptable" in the sense of being compatible with the GPCR and not deleterious to the recipients thereof. Typically, the carriers will be water or saline which will be sterile and pyrogen-free.

The following examples illustrate pharmaceutical formulations according to the invention in which the active ingredient is a GPCR protein and/or GPCR-encoding polynucleotide antibody of the invention.

Injectable Formulation

| | |
|---|---|
| Active ingredient | 0.200 g |
| Sterile, pyrogen free phosphate buffer (pH 7.0) to | 10 ml |

The active ingredient is dissolved in most of the phosphate buffer (35-40° C.), then made up to volume and filtered through a sterile micropore filter into a sterile 10 ml amber glass vial (type 1) and sealed with sterile closures and overseals.

Intramuscular Injection

| Active ingredient | 0.20 g |
|---|---|
| Benzyl Alcohol | 0.10 g |
| Glucofurol 75 ® | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (type 1).

It is appreciated that when a GPCR protein is used as a vaccine, the GPCR may be in complex with a ligand. An advantage of complexing the GPCR with a ligand is to enable the generation of antibodies with reduced side-effects. For example, when the GPCR is bound to a ligand, epitopes (e.g. T cell and B cell epitopes) in that ligand binding site are masked and so no antibodies specific for that binding site are generated; however, antibodies may still be generated against ligand binding sites where the epitopes remain unmasked.

By "ligand" we include any molecule which binds to the GPCR. Many suitable ligands are known, for example from WO 2008/114020 and Neubig et al (2003) *Pharmacol. Rev.* 55, 597-606, both of which are incorporated herein by reference.

Conveniently, the ligand is one that binds to a GPCR so as to mask epitopes in a binding site of a natural ligand, which ligand's activity is still desired after vaccination.

Preferably, the above-mentioned ligands are small organic or inorganic moieties, but they may be peptides or polypeptides.

Typically, the ligand binds to the GPCR protein with a $K_d$ of from mM to pM, such as in the range of from μM (micromolar) to nM. Generally, the ligands with the lowest Kd are preferred, and it is appreciated that the ligand should preferably remain bound to the GPCR protein following administration of the vaccine.

The ligand may be a peptidomimetic, a nucleic acid, a peptide nucleic acid (PNA) or an aptamer. It may be an ion such as $Na^+$ or $Zn^{2+}$, a lipid such as oleamide, or a carbohydrate such as heparin.

The ligand may be a polypeptide which binds to the GPCR. Such polypeptides (by which we include oligopeptides) are typically from $M_r$ 500 to $M_r$ 50,000, but may be larger. The polypeptide may be a naturally occurring GPCR-interacting protein or other protein which interacts with the GPCR, or a derivative or fragment thereof. The polypeptide ligand may conveniently be an antibody which binds to the GPCR. By the term "antibody" we include naturally-occurring antibodies, monoclonal antibodies and fragments thereof. We also include engineered antibodies and molecules which are antibody-like in their binding characteristics, including single chain Fv (scFv) molecules and domain antibodies (dAbs). Mention is also made of camelid antibodies and engineered camelid antibodies.

In one embodiment, the ligand is covalently joined to the GPCR. Some GPCRs (for example thrombin receptor) are cleaved N-terminally by a protease and the new N-terminus binds to the agonist site. Thus, such GPCRs are natural GPCR-ligand fusions.

The GPCR may alternatively be complexed with other molecules such as by synthetically modifying the GPCR by for example covalent attachment of moieties such as polyethylene glycol, to mask epitopes.

As an alternative to complexing the GPCR with a ligand to generate antibodies with reduced side-effects, the GPCR may be engineered to ablate at least one ligand binding site. Thus, in one embodiment, the GPCR is an engineered GPCR which, when compared to the wild type GPCR lacks at least one epitope in a first ligand binding site and preserves at least one epitope in a second ligand binding site. For example, this may be accomplished by removing T cell epitopes and/or B cell epitopes from ligand A's binding site, but leaving such epitopes in situ in ligand B's binding site. Upon vaccination, the GPCR would generate antibodies to the binding site of ligand B but not ligand A (i.e. leaving the ligand A-receptor function intact).

T-cell epitopes can be predicted using algorithms or by using standard T-cell-peptide MHC Class I assays to evaluate immunogenicity (Desmet et al, 2005 Proteins 58(1): 53-69). Similar algorithmic methods to predict B cell epitopes are known in the art.

By an engineered GPCR we include the meaning of a GPCR wherein one or more epitopes have been ablated using standard genetic engineering and recombinant technology techniques. Thus, the GPCR may be a mutant GPCR which compared to its parent GPCR has one or more different amino acid sequences to the respective amino acid sequences that define one or more epitopes in the parent GPCR. Preferably, the different amino acid sequences replacing those sequences in the parent GPCR are non-immunogenic. By an engineered GPCR we also include the meaning of a GPCR wherein one or more epitopes have been ablated by synthetically modifying the GPCR after its expression.

Use of GPCRs to Inhibit Activity of GPCR Binding Partners

As well as GPCRs having utility as vaccines, we have recognised that they may also be used to inhibit the activity of GPCR binding partners when desirable to do so. For example, autoantibodies targeting GPCRs are implicated in various disease conditions, and many toxins such as plant toxins and snake venoms target GPCRs. Thus, GPCRs may be used to neutralise the activity of such undesirable binding partners, for example by acting as a decoy receptor and/or aid the removal of the binding partners from a subject.

Accordingly, a further aspect of the invention provides a GPCR or a polynucleotide encoding said GPCR for use in inhibiting an activity of a GPCR binding partner in a subject.

Preferences for the GPCR include those described above. Most preferably, the GPCR is a mutant GPCR that has increased stability relative to its parent GPCR in a particular conformation, such as an agonist or antagonist conformation.

It will be appreciated, that when the GPCR is used to inhibit the activity of a given GPCR binding partner, the GPCR is one that binds to that GPCR binding partner. Preferably, the GPCR is one that binds selectively to that GPCR binding partner (i.e. to a greater extent than it binds to any other GPCR binding partner) and most preferably one derived from the same species as the GPCR binding partner in question. Thus, when the GPCR is used to inhibit the activity of a human GPCR binding partner, the GPCR is a human GPCR, and so on.

Typically, the GPCR binding partner is one that is present in a subject at a particular concentration that produces an undesirable effect in vivo. For example, the binding partner may be a GPCR autoantibody or it may be a toxin that binds to GPCRs or it may be an endogenous GPCR ligand, such as one that is present at above normal concentrations. Specific examples are provided below.

By 'an activity of a GPCR binding partner' we include the meaning of the GPCR binding partner's biological activity in vivo.

Typically, the activity is a GPCR signalling pathway modulating activity by virtue of the binding partner binding to a GPCR. This signalling pathway modulating activity can be assessed by any suitable assay known for the particular GPCR signalling pathway. For example, the activity may be measured by using a reporter gene to measure the activity of the particular signalling pathway. By a reporter gene we include genes which encode a reporter protein whose activity may easily be assayed, for example β-galactosidase, chloramphenicol acetyl transferase (CAT) gene, luciferase or Green Fluorescent Protein (see, for example, Tan et al., 1996 *EMBO J.* 15(17): 462942). Several techniques are available in the art to detect and measure expression of a reporter gene which would be suitable for use. Many of these are available in kits both for determining expression in vitro and in vivo. Alternatively, signalling may be assayed by the analysis of downstream targets. For example, a particular protein whose expression is known to be under the control of a specific GPCR signalling pathway may be quantified. Protein levels in biological samples can be determined using any suitable method known in the art. For example, protein concentration can be studied by a range of antibody based methods including immunoassays, such as ELISAs, western blotting and radioimmunoassay.

By 'an activity of a GPCR binding partner' we also include the meaning of the GPCR binding partner binding to endogenous GPCR in a subject. Binding activity can be assessed using routine binding assays known in the art.

By 'inhibits an activity of a GPCR binding partner' we include the meaning of reducing the activity of the GPCR binding partner or reducing the activity to a substantially undetectable level or abolishing the activity.

It is preferred if the GPCR inhibits an activity of a GPCR binding partner selectively. By 'inhibits selectively' we include the meaning that the GPCR has an $IC_{50}$ value for a particular GPCR binding partner which is lower than for other chemical moieties (e.g. GPCR binding partners). Preferably, the GPCR has an $IC_{50}$ value for a particular GPCR binding partner which is at least five or ten times lower than for at least one other chemical moiety (e.g. GPCR binding partner), and preferably more than 100 or 500 or 1000 or 5000 times lower.

It is appreciated that a GPCR may inhibit an activity of a GPCR binding partner either by binding to a GPCR binding partner in vivo so as to prevent the binding partner binding to endogenous GPCR (and thereby modulating GPCR signalling) and/or by binding to a GPCR binding partner so as to remove it from a subject ex vivo.

Applications of Inhibiting Activity of GPCR Binding Partner—Neutralisation/Removal of Anti-GPCR Antibodies Autoantibodies targeting GPCRs are associated with various pathological conditions in a similar manner to activating or inactivating mutations of GPCRs. As yet, it is unclear if the autoantibodies result from the primary target-damaging disease mechanism or if they are generated secondary to a pre-existing injury or infection, and this may well vary according to disease. Examples of disease conditions linked to agonist or antagonist GPCR autoantibodies include:—

Graves disease: TSH receptor;
Atherosclerosis: β2AR;
Cardiomyopathy:
  a) Allergic asthma—β2AR;
  b) Dilated cardiomyopathy—β1AR;
  c) Chagas' cardiomyopathy—β1AR and M2 muscarinic;
  d) Ischaemic cardiopathy—β1AR;

Hypertension:
  a) Refractory hypertension—Alpha1A-adrenergic receptor;
  b) Malignant hypertension—Alpha1A-adrenergic receptor;
  c) Pre-eclampsia (hypertension in pregnancy)—angiotensin II type I receptor;

Autoimmune Polyendocrine Syndrome Type 1: Calcium-sensing receptor;

Recipients of renal allografts with severe vascular rejection and malignant hypertension with no anti-HLA antibodies: Angiotensin II type I receptor. Although the epitopes for these autoantibodies are located on the same region of the molecule, there appears to be a distinction between the epitopes mapped in both conditions;

Diabetes: autoantibodies for angiotensin II type I receptor, β1AR and Alpha1A-adrenergic receptor have been reported in type 2 diabetes patient sera. The presence of these autoantibodies has implications for diabetic complications, such as hypertension and vascular damage;

Sjögrens syndrome: Muscarinic acetylcholine receptor;
Autoimmune encephalitis: $GABA_B$ receptor.

Thus, any of the mentioned GPCRs may be used to remove the corresponding GPCR autoantibodies and have therapeutic benefit according to the invention.

The production of GPCR autoantibodies is believed to stem from the degradation of GPCRs to peptides that complex with HLA class II molecules for presentation to the immune system. This then induces an autoimmune response that is precipitated in certain conditions.

Molecular mimicry may be responsible for the initial activation of T cells that are auto-reactive, as well as subsequent expansion of T cell memory cells. Evidence for this is provided by β1AR autoantibodies thought to be generated as a result of *Trypanosoma cruzi* infection, where a functional autoimmune response has been demonstrated against cardiac β1AR. Further, it has also been demonstrated that there is a structural basis for the cross-reaction between an antibody to the *T. cruzi* P213 protein and the β1AR receptor (Smulski et al 2006).

Additional supporting evidence for molecular mimicry is anti-$M_2$ AchR autoantibodies. These have been detected in patients with Chagas disease and have been affinity purified from polyclonal patient sera. A sub-population of affinity purified antibodies has also been isolated that recognise a cross-reactive epitope on both the β1AR and $M_2$AchR receptors that corresponds to a polyanionic domain of ECL2. This polyanionic region also corresponds to the cross-reactive epitope between the *T. cruzi* P2β protein and the β1AR receptor mentioned above.

Chagas disease results from infection with the parasite *T. cruzi* that is spread by biting insects. The disease is estimated to affect approximately eight million people in Latin America, of whom approximately 30-40 percent will develop serious cardiac disease, digestive disease, or both as a result of infection. It is recognized by the World Health Organization (WHO) as a neglected tropical disease and is also becoming an emerging health problem in non-endemic areas via migration of infected populations from endemic areas. Currently, only two drugs are approved for treatment: benznidazole and nifurtimox.

A yet further example of molecular mimicry is believed to be parvovirus B19 antibodies against VP2 epitopes, which have been associated with the generation of AT1R Abs in pre-eclampsia (Herse et al, 2009).

Immune responses raised against non-specific infections or local hypoxia (both of which effectively stimulate antibody production) can also induce tissue damage which is thought to have a role in generating anti-GPCR antibodies. These agonistic autoantibodies often target the second extracellular loop of the GPCR in question and activate the receptor. Significantly, it is possible for antagonists to abolish interaction of the autoantibodies with the receptor thereby preventing damage to the target tissue.

Further GPCR autoantibodies that have been implicated in disease are described below.

In Graves' disease, autoantibodies against the TSH receptor leads to excessive thyroid hormone synthesis and directly cause thyrotoxicosis and thyroid hyperplasia resulting in hyperthyroidism (and goitre) due to autoantibodies mimicking TSH binding to cause production of intracellular cAMP (Prabhakar et al, 2003). Some of these autoantibodies are reported to activate phospholipase A thereby contributing to goitre (Di Paola et al, 1997). The mechanism of disease also leads to orbital tissue inflammation and thyroid-associated opthalmopathy (Douglas et al, 2010). The ideal treatment for patients suffering from Graves' disease would correct the autoimmune responses in the thyroid and orbit of the eye so as to enable restoration of normal thyroid function and elimination of the opthalmopathy. However, this is not yet available and current treatments comprise anti-thyroid drugs, radioactive iodine and surgery. Immunosuppressive therapy would be nonspecific and thus create side effects. Therefore, using a TSH GPCR to remove and/or neutralise circulating autoantibodies would provide a much more satisfactory alternative for the patient.

Alpha 1AR, β1AR and AT1R autoantibodies have been implicated in cardiovascular and renal pathologies. These autoantibodies are thought to induce various cardiovascular and renal injuries, but the mechanisms of injury are not clear. Ultimately, induction of signal transduction pathways by alpha 1AR autoantibodies will lead to PKC-α in cardiomyocytes and Erk 1/2 kinases in vascular smooth muscle cells (both implicated in hypertension induced organ damage). These autoantibodies also induce short-term Ca2+ responses.

β1AR autoantibodies are better characterised than alpha 1AR autoantibodies and activate the β1AR receptor by stabilising the receptor agonist conformation, i.e. they act as agonists. The signalling pathways involved include those leading to cardiomyocyte toxicity. Direct evidence for this has been illustrated by inducing cardiomyopathy by immunising rats with β1AR extracellular loop epitopes, and then transferring the disease to healthy rats by passive transfer of the autoantibodies (Jahns et al, 2004).

Angiotensin AT1R autoantibodies are involved in Erk 1/2 kinase signalling pathway and directly influence endothelial and vascular smooth muscle cells. Autoantibodies against AT1R have been implicated in haemostasis and inflammation manifesting as graft rejection in renal transplantation, structural changes in the arterial wall associated with clotting and luminal narrowing, and placental abnormalities. Evidence for these changes includes an example where AT1R autoantibodies from women suffering pre-eclampsia were infused into pregnant mice that subsequently developed key symptoms of pre-eclampsia, including hypertension, proteinuria and pathological changes in the placenta (Zhou et al, 2010). AT1R agonistic autoantibodies have been demonstrated to stimulate sEng via receptor activation (Zhou et al, 2010) where the placenta was identified as the source contributing to sEng production. Soluble endoglin (sEng) is found in high circulating levels in pre-eclampsic women and levels directly correlate with disease severity. The induction of sEng by AT1R autoantibodies is mediated via TNFα, which subsequently leads to impaired placental angiogenesis.

Anti-calcium-sensing receptor (CaSR) antibodies have been detected in a subset of patients with autoimmune polyendocrine syndrome type 1 (APS1). CaSR maintains calcium homeostasis and regulates PTH synthesis and renal calcium excretion. These antibodies were characterised by their ability to increase both Ca2+-dependent ERK1/2 phosphorylation and inositol phosphate (IP) accumulation in CaSR-expressing HEK293 cells (Kemp et al, 2009). Such antibodies are likely to have a direct role in the pathogenesis of the condition. APS1 is caused by a rare autosomal recessive disorder caused by mutations in the autoimmune regulator gene (AIRE) and is characterised by multiple organ-specific autoimmunity, as well as ectodermal pathologies. Hypoparathyroidism occurs in 80% of patients and is associated with hypocalcemia, hyperphosphatemia and low serum levels of PTH. It has been suggested that these clinical symptoms could result from a humoral immune response to parathyroid cells.

Activating anti-CaSR autoAbs have also been described in a subset of patients suffering from autoimmune hypoparathyroidism (AH) as well as autoimmune hypocalciuric hypercalcemia (AHH) with one unique autoantibody reported as an allosteric modulator (Makita et al, 2007) and another as a blocking autoantibody that inhibited the calcium signalling pathways (Pallais et al, 2004). It is thought that disease pathogenesis in the subset of patients where activating autoantibodies have been described is the result of functional suppression of the parathyroid glands rather than irreversible destruction (Kemp et al, 2009). In fact, it has been observed that patients can still retain morphologically intact tissue (Kifor et al, 2004). Therefore, the removal of such autoantibodies could potentially restore residual function of the parathyroid tissue.

Autoantibodies against the muscarinic acetylcholine receptor (mAchR) are believed to be responsible for disease manifestations in Sjögren's syndrome. Autonomic nervous system (ANS) abnormalities are common in Sjögren's syndrome; failure of sympathetic and parasympathetic innervation of the exocrine glands, such as salivary and lachrymal glands, affects vascularity and secretory function. It is thought that this dysfunction is mediated by faulty muscarinic receptor signalling. Specifically, the type 3 receptor is responsible for saliva production and it has been reported that autoantibodies against the M3R are present in up to 90% patients. Most studies have focused on the extracellular loop 2 as the antigenic determinant, but more recently data has been described that suggests that the extracellular loop 3 possesses the functional epitope reactive with autoantibodies (Koo et al, 2008). In addition, it has also been demonstrated that affinity purified anti-M3R autoantibodies can block other antibodies from binding to the nerve ending junctions of epithelial cell membranes isolated from normal salivary glands.

Autoantibodies against mAchR have also been reported in the sera of patients in Stage 1 breast cancer; the study described the characterisation of immunoglobulin G purified from breast cancer patients and the ability of the IgG to modulate proliferation of MCF-7 breast cancer cells (Negroni et al 2010) by stimulation of the muscarinic signalling pathway. The authors demonstrated $M_3$ and $M_4$ receptor expression in MCF-7 cells and that the proliferative effect of the autoantibodies was due to $M_3$ receptor activation via phospholipase C-induced nitric oxide release by calcium-dependent nitric oxide synthases.

Autoantibodies to the GABA$_B$ receptor have been implicated in the pathogenesis of autoimmune encephalitis. It has even been suggested that these autoantibodies possess complement-dependent-cytotoxicity or CDC.

Hence, there is demand for a simple and effective strategy for the rapid reduction of these autoantibody titres. Extracorporeal plasma exchange (PE) has clinically validated the strategy of removing disease-causing autoantibodies as evidenced by the great improvement in patient disease status. However, PE is a blanket process removing all immunoglobulins and other plasma proteins in the process. Thus, using GPCRs to selectively reduce the activity of the particular autoantibodies either by aiding the selective removal of autoantibodies ex vivo and/or by neutralising their effect in vivo (e.g. by acting as a decoy receptor) would be of greater clinical significance and value for the patient.

Precedence for removing autoantibodies by immunoadsorption is provided by the studies of Wenzel et al 2008.

Precedence for an in vivo adsorption strategy has been exemplified by using nanodiscs incorporated with the acetylcholine receptor for the adsorption and removal from the circulatory system of autoantibodies prevalent in myasthenia gravis in a murine disease model (Sheng et al, 2010). Also, polyclonal ovine antibody fragments such as DigiFab™ and Digibind® are being investigated for the treatment of severe pre-eclampsia and eclampsia (a condition that occurs in 10% of pregnancies worldwide per year) as a means to combat autoantibodies.

Applications of Inhibiting Activity of GPCR Binding Partner—Neutralisation/Removal of Toxins GPCRs also have the potential to be of value in treating intoxication. It is well documented that a number of plant toxins and alkaloids, as well as several snake venoms, target GPCRs.

Toxins whose activity may be inhibited by GPCRs are discussed below.

A recent detailed study of plant toxins reviewed common sources of plant poisonings of dogs and cats in South Africa (Botha and Penrith, 2009). Although the study focussed on dogs and cats, it can nevertheless be extended to humans as many of these plant species are endogenous to other geographical locations or have been exported as ornamental garden plants across the world. The plant species included *Cannabis sativa* (toxin is Delta 9 THC targeting the CB1 receptor); *Datura stramonium* also known as Jimsonweed and the *Belladonna* or nightshade spp (toxin is atropine targeting the mAchR); and *Ornithogalum* spp which includes tulips, lilies and daffodils (toxin is calcium oxalate crystals). Calcium oxalate crystals are also present in the Araceae family and soluble calcium oxalate is found in numerous common garden plants, such as rhubarb. Soluble oxalate poisoning has been reported in several species of livestock.

Cardiac glycosides derived from digoxin found in *Digitalis* spp (Foxglove) can present a danger with regard to overdosing or deliberate self-poisoning. Common oleander (*Nerium oleander*) and particularly yellow oleander (*Thevetia peruviana*) are common garden plants that also contain cardiac glycosides. Oleaner poisoning kills by blocking acetylcholinesterase (Ach) leading to increase in Ach by over stimulation of muscarinic receptors. Patients develop digoxin-like toxicity because of the cardiac glycosides. Atropine administration can control the production of fluid (sweat, lungs, mouth), but it is unable to prevent acute respiratory failure. In this instance, rather than removing the plant toxin ex vivo using a GPCR, the strategy would be to remove excessive levels of acetylcholine in vivo using a muscarinc acid receptor. Thus, in this case, the GPCR binding partner is a GPCR ligand, the concentration of which has increased to undesirable levels due to the presence of a toxin. Some precedence has been set for this approach where Fab fragments have been used to specifically target digoxin neutralisation and clearance.

Various drugs are often involved with poisonings & toxicities, either after accidental overdosing or deliberate consumption, such as with recreational drugs.

For example, cannabinoid hyperemesis syndrome is characterized by chronic, heavy use of *cannabis*, recurrent episodes of severe nausea and intractable vomiting, and abdominal pain. Other than stopping *cannabis* use, there is no proven treatment. *Cannabis* intoxication can also cause psychosis with the risk of psychosis or even schizophrenia increasing with higher potency varieties.

The opioid family of receptors is probably the most obvious receptor class associated with toxin effects, in particular the μ-opioid receptor which is the major target of analgesics. Opioid poisoning may occur accidently with regard to pain management and the administration of analgesic. A higher dose may be required over time to maintain the same level of analgesia due to opioid-induced tolerance. At times, progressive disease may be the reason for higher opioid requirements. Morphine and methadone are used as opioid agonists and are often substances of abuse even in the rehabilitation treatment of heroin users. Here the danger of addiction and the link to overdosing is clear.

Bromo-DragonFLY is a psychedelic hallucinogenic drug related to the phenethylamine family. It is considered an extremely potent hallucinogen, only slightly less potent than LSD with a normal dose in the region of 200 μg to 800 μg, and has long duration of action up to several days. The hallucinogenic effect is mediated by its agonist activity at the $5\text{-}HT_{2A}$ serotonin receptor. Bromo-DragonFLY also has a high binding affinity for the $5\text{-}HT_{2B}$ and $5\text{-}HT_{2C}$ serotonin receptors, and is considered a non-subtype selective $5\text{-}HT_2$ agonist. However, it is actually twice as potent for $5\text{-}HT_{2C}$ receptors as for $5\text{-}HT_{2A}$, as well as being less than 5× selective for $5\text{-}HT_{2A}$ over $5\text{-}HT_{2B}$. The toxicity of Bromo-DragonFLY appears to be fairly high for humans when taken in doses above the therapeutic range. Another property of this compound is that it can be a long-acting efficacious vasoconstrictor, leading to necrosis and gangrene which can be delayed by several weeks after the initial overdose.

Other toxins that target GPCRs include the muscarinic toxin (MT) snake venoms that bind to muscarinic acetylcholine receptors (Potter et al 2001) and some recently described toxins that possess beta-blocking activity (Rajagopalan et al, 2007).

MTs have been isolated from the venom of the East African green mamba *Dendroaspis angusticeps* (toxins MT1-MT7), the black mamba *Dendroaspis polylepis* (toxins MTα, MTβ and MTγ), and the Chinese cobra *Naja atra*. A 3FTX described as a β-cardiotoxin with beta-blocker activity has been isolated from King cobra *Ophiophagus hannah* venom and characterised for functional activity. The genus *Dendroaspis* belongs to the Elapidae family which includes the cobra genus *Naja* and so it is not surprising that the venoms of the mambas and the cobras have similarities.

MT toxins are often described as three-finger toxins (3FTX) and are closely homologous to α-neurotoxins and are usually non-enzymatic. Interestingly, it has been reported that the Chinese cobra *Naja atra* venom also contains phospholipase $A_2$ activity that potentially targets mAchRs directly or induces acetylcholine release via another mechanism (Huang et al, 2008). All members of this family share a similar fold that consists of three finger-like loops made of a β-sheet structure that protrudes from a globular core and is stabilized by several intra-molecular disulphide bonds giving rise to a compact "β-cross motif".

MTs exhibit moderate to high selectivity among the mAchR receptor subtypes, for example MT7 is a highly potent and selective antagonist for the $M_1$ mAchR subtype with no detectable cross-specificity for the other subtypes (Fruchart-Gaillard et al, 2006), whereas the FTX MTα has also been reported to be a selective $α2_B$-adrenoreceptor antagonist with more potency for the $α2_B$-adrenoreceptor than for the muscarinic receptors (Koivula et al, 2010). Differences between the toxins do exist; m1-toxin1 and m4-toxin (MT3) are antagonists (Cuevas et al, 1997) whereas MT1 and MT2 are allosteric agonists (Jerusalinsky et al, 1995). There is variability in the binding affinities, where m1-toxin1 binds specifically and irreversibly to $M_1$ receptors, m4-toxin binds with over 100-fold high affinity to $M_4$ receptors than $M_1$ receptors, with other toxins binding reversibly and to more than one receptor subtype. It has been suggested that the C-terminal Lys of m1-toxin1 may contact an outer loop of the $M_1$ receptor (Krajejewski et al, 2001). Consequently, a decoy receptor engineered in a conformation designed to specifically bind m1-toxin1 and/or other high affinity binding toxins would be of tremendous utility for medical emergency treatment of potentially fatal envenomation that requires immediate hospitalisation.

Given the severe shortage of affordable antivenoms and antitoxins in the developing world, compounded by limited antidote development, GPCRs have the potential to be effective at treating envenomated subjects.

Precedence for the neutralisation of toxins is provided by an anti-digoxin Fab used to treat oleander poisoning. Anti-digoxin Fab began clinical trials in Sri Lanka in 1996-7 and was released in 2001 with stocks running out in 2002 due to affordability. The antitoxin Fab fragment markedly reduced case fatality and its absence resulted in a three-fold rise in deaths (Eddlestone et al, 2003). Other anti-toxin examples include anti-digoxin Fab fragments for the treatment of digoxin toxicity (Sinclair et al 1989), marketed as DigiFab and DigiBind, and ViperaTAb for combating cardiotoxins present in viper venom (some of which could potentially affect the β1AR receptor).

It is appreciated that intravenous injection of a GPCR as a decoy receptor would be most appropriate where immediate action is required for the neutralisation/detoxification process, as well as a simple first-on-scene treatment prior to transporting a patient for further emergency treatment. Further treatment may then include passing patient blood or plasma over an affinity column comprising a GPCR as a means of capturing and removing any remaining toxin in circulation.

Methods for Inhibiting Activity of GPCR Binding Partners

As discussed above, GPCRs may be used to inhibit the activity of GPCR binding partner by removing GPCR binding partners such as autoantibodies, toxins and endogenous ligands from a subject (ex vivo removal).

Thus, the invention provides a method of selectively removing a GPCR binding partner from a subject, the method comprising providing fluid from the subject containing the GPCR binding partner (e.g. autoantibody or toxin) and contacting the fluid with a GPCR so as to remove the GPCR binding partner from the fluid.

Similarly, the invention provides a method of inhibiting an activity of a GPCR binding partner in a subject, the method comprising selectively removing the GPCR binding partner from a subject extracorporeally by means of a GPCR.

The fluid from which the GPCR binding partner has been removed is usually re-introduced into the subject. Conveniently therefore, the method comprises (i) establishing an extracorporeal circulation system wherein whole blood or components thereof are contacted with a GPCR capable of binding to the GPCR binding partner to be removed so as to remove the GPCR binding partner (e.g. by affinity chromatography), and (ii) returning the contacted whole blood or components thereof into the original blood, wherein the contacted whole blood or components thereof contain substantially fewer GPCR binding partner (e.g. autoantibody, toxin or endogenous ligand) relative to the amount originally residing in the subject.

Preferences for the GPCR and GPCR binding partner include those described above. Conveniently, the GPCR is one that has increased stability in a particular conformation relative to a parent GPCR (e.g. in an agonist or antagonist conformation).

By 'selectively removing' we include the meaning that the GPCR binding partner in the fluid is removed to a greater extent than any other component of the fluid.

Preferably, only the GPCR binding partner is removed. For the avoidance of doubt, by 'removing' we also include the meaning of reducing the concentration of the GPCR binding partner in the fluid. Typically, the method reduces the concentration of the GPCR binding partner in the fluid at least by 5 times, 10 times, 50 times or 100 times, and most preferably the method reduces the concentration to an undetectable level.

Generally, the fluid is a blood fluid such as plasma or serum or whole blood. Typically, the fluid is blood plasma and the GPCR binding partner is selectively removed by plasma exchange.

The GPCR binding partner may be removed using affinity chromatography. Thus, in one embodiment, the fluid containing the GPCR binding partner is subjected to affinity chromatography using an adsorbent comprising a GPCR.

It is appreciated that the invention also provides an adsorbent for selectively removing a GPCR binding partner from a subject, which adsorbent comprises a GPCR.

As is well known in the art, a variety of matrix materials can be used in the adsorbent provided that it is inert. By "inert" we including the meaning that the matrix material does not have any negative impact on the various fluids used in affinity chromatography, such as blood plasma, binding buffers, regeneration buffers, or storage buffers and the like. Suitable matrix materials-include carbohydrates such as cross-linked modified agarose, silicates, glasses, and organic polyreaction products including polymers or copolymers. The matrix material may be present in any form such as spherical, planar or fibrous, and may be porous or non-porous. It may be present in the form of porous beads. Further, the matrix material is typically biocompatible, and additionally, exhibits substantially no leakage. Examples of a solid matrix material for GPCR immobilisation include polymers such as agarose; cellulose; polystyrene; Mono Q; Source; and activated affinity resins. For coupling the GPCR to the matrix material, the GPCR can be directly coupled onto the matrix material via a chemical reaction or indirectly coupled onto the matrix material using a spacer. Typically, the GPCR is coupled by the use of a N- or preferably a C-terminal tag, examples including but not limited to a His-tag (His6 or His10), a terminal Biotin and a FLAG tag. Preferably, the GPCR coupled to the matrix is a mutant GPCR that has increased conformational stability relative to its parent GPCR in a particular conformation (e.g. agonist).

As well as being used to remove GPCR binding partners ex vivo, GPCRs may also be used to inhibit the activity of a GPCR binding partner in vivo (i.e. in vivo neutralisation). Thus, the invention also provides a method of inhibiting an activity of a GPCR binding partner in a subject, the method comprising administering a GPCR or a polynucleotide encoding said GPCR to the subject. In this way, the GPCR may be used to remove the GPCR binding partner from the circulation by in vivo adsorption which neutralises the effect of the GPCR binding partner by preventing it from binding to endogenous GPCR. Typically, the method comprises administering purified GPCR protein to the subject.

Preferences for the GPCR and GPCR binding partner include those described above. Conveniently, the GPCR is one that has increased stability in a particular conformation relative to a parent GPCR (e.g. in an agonist or antagonist conformation).

In certain embodiments, the GPCR is administered alone.

Suitable formulations and routes of administration include those described above. Preferably, the GPCR is administered intravenously, for example using an intravenous drip.

The invention includes a method of combating a condition in which a GPCR binding partner is implicated, the method comprising carrying out a method of inhibiting the activity of a GPCR binding partner as defined above.

Similarly, the invention includes a GPCR for use in combating a condition in which a GPCR binding partner is implicated, and the use of a GPCR in the manufacture of a medicament for combating a condition in which a GPCR binding partner is implicated.

By a condition in which a GPCR binding partner is implicated, we include the meaning of any biological or medical condition or disorder in which at least part of the pathology is mediated by an activity of a GPCR binding partner, typically a GPCR signalling modulating activity by virtue of the binding partner binding to endogenous GPCR. The condition may be caused by the GPCR binding partner activity or may simply be characterised by the GPCR binding partner activity. It is expected that inhibiting a GPCR binding partner activity will prevent, ameliorate or treat the condition so characterised. Thus, by combating a particular disease or condition we include the meaning of reducing or alleviating symptoms in a patient (i.e. palliative use), preventing symptoms from worsening or progressing, combating the disorder (e.g. by inhibition or elimination of the causative agent), or prevention of the condition or disorder in a subject who is free therefrom.

Generally, the condition is an autoimmune disorder or evenomation or intoxication, such as any of those conditions described above.

The subject in the methods and uses of the invention may be a mammalian individual, such as a human, horse, dog, pig, cow, sheep, rat, mouse, guinea pig or primate. Preferably, the subject is a human.

In a separate aspect of the invention, antibodies generated to a particular GPCR can be conjugated to various drugs for targeted therapeutic intervention, for example, in the treatment of cancer. Particularly useful antibodies for this purpose would be camel antibodies. It is appreciated that the antibody would not necessarily need to have functional activity for this purpose provided that it retained specific binding for the receptor in question (e.g. for use in targeted radiotherapy). It will also be understood that targeted delivery of toxins, such as auristatins that are anti-tubulin drugs (Seattle Genetics—Antibody Drug Conjugate technology) or maytansinoids (Immunogen—Targeted Antibody Payload technology) would require internalisation.

The invention will now be described in more detail with respect to the following Figures and Examples wherein:

DESCRIPTION OF FIGURES

FIG. 1A-B—Alignment of the turkey β-adrenergic receptor (SEQ ID NO:1) with human β1 (SEQ ID NO:2), β2(SEQ ID NO:3) and 3(SEQ ID NO:4) receptors.

FIG. 2A-B—Alignment of human adenosine receptors. $AA2AR_{13}$human corresponds to SEQ ID NO:5; $AA2BR_{13}$human corresponds to SEQ ID NO:6; $AA3R_{13}$human corresponds to SEQ ID NO:7; and $AA1R_{13}$human corresponds to SEQ ID NO:8.

FIG. 3A-B—Alignment of neurotensin receptors. $NTR1_{13}$rat corresponds to SEQ ID NO:9; $NTR1_{13}$human corresponds to SEQ ID NO:10; and $NTR2_{13}$human corresponds to SEQ ID NO:11.

Figure 4A:
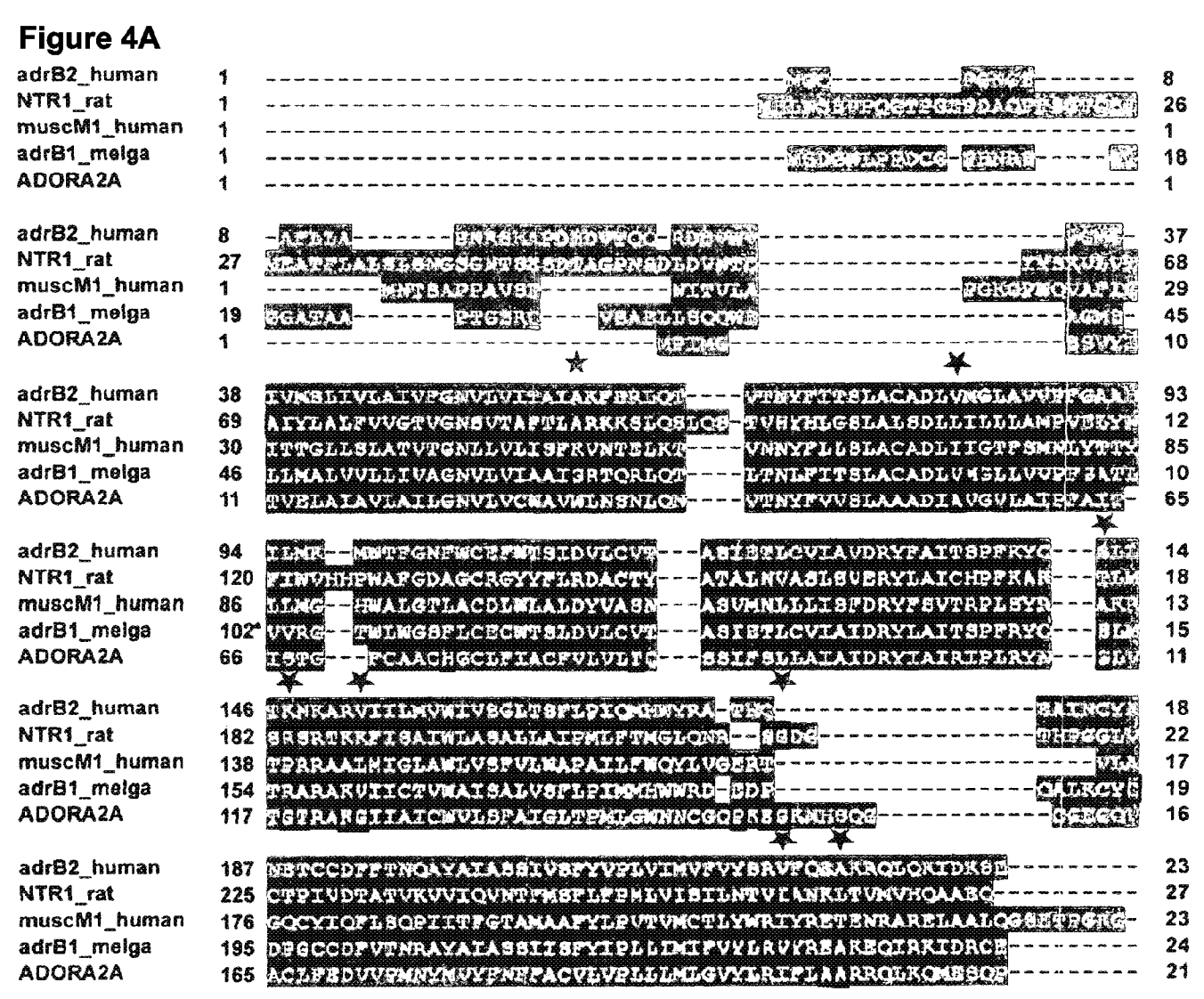

FIG. 4A-C—Multiple sequence alignment of human beta-2AR (SEQ ID NO:3), rat NTR1 (SEQ ID NO:9), turkey beta-1 AR (SEQ ID NO:1), human Adenosine A2aR and human muscarinic M1 (SEQ ID NO:12) receptors. In each sequence, thermostabilising mutations are marked with a box. Mutations occurring in two or more sequences are denoted with a star.

β1AR StaR expression is detected by an anti-tag antibody and represented by the green curve (marked G); the negative control, an irrelevant cDNA, is represented by the blue curve (marked B).

Figure 6C:
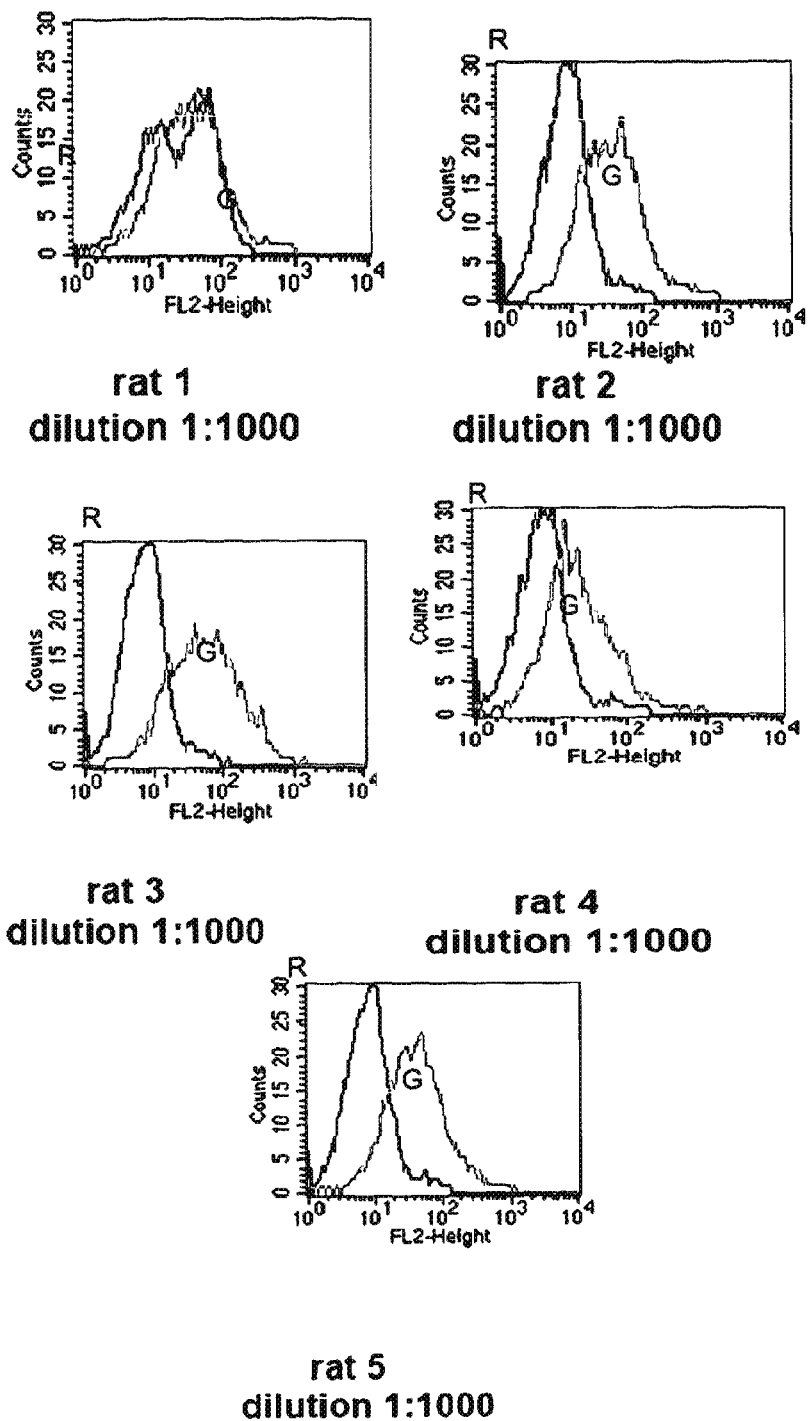

FIG. 6A-C—Evaluation of sera titre in immune response by FACS

A pre-immune sera sample (Mouse 1) was compared with an interim bleed to monitor the immune response. The green curve (marked G) represents β1AR StaR expressing cells; the red curve (marked R) represents cells transfected with an irrelevant cDNA. A significant immune response was observed in the immunised cohorts.

FIG. 7—Evaluation of sera titre in immune response by ELISA

His-tagged β1AR StaR (36 m23) was immobilised on a 96-well nickel chelate plate and sera samples diluted for analysis to evaluate binding to β1AR. In mice, boosting with StaR protein maintains titre at the same level or increases titre slightly.

Figure 8A:
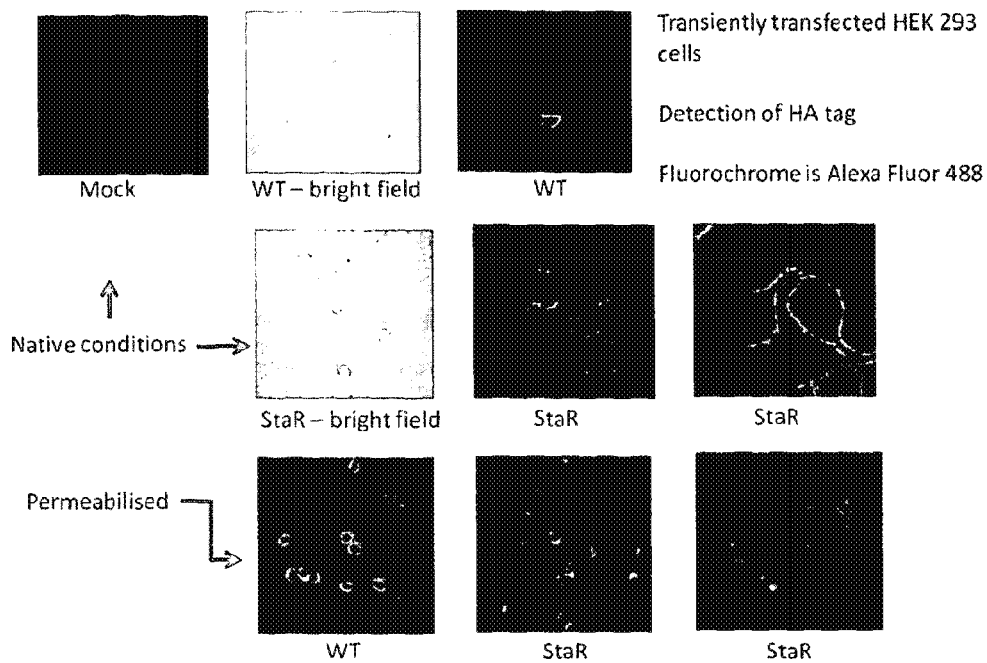
Figure 8B:
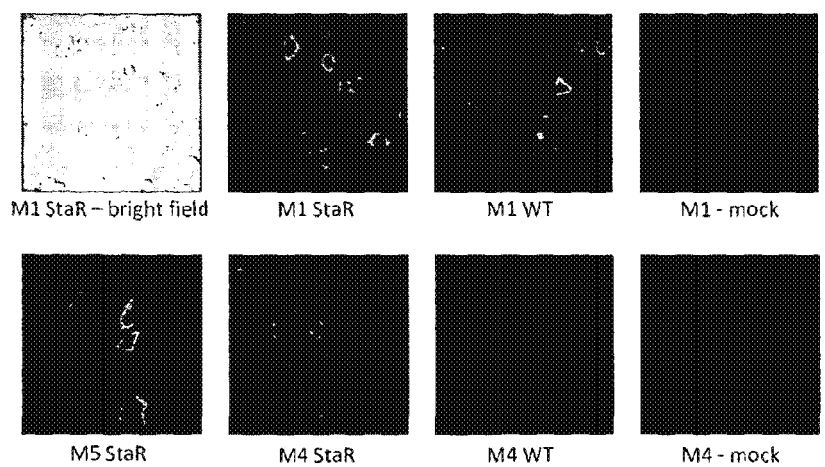
Figure 8C:
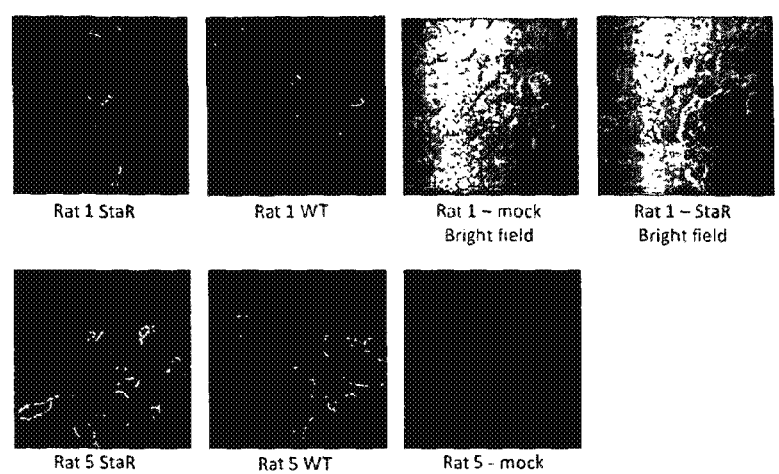

FIG. 8 A-C—Immunofluorescence

The immunofluorescence data demonstrates that expression and subcellular localisation of the StaR is similar to that observed with the wild-type receptor.

A. Controls—detection of N terminally HA-tagged WT and StaR.

B. Mouse sera—native conditions

C. Rat sera—native conditions

Figure 9C:
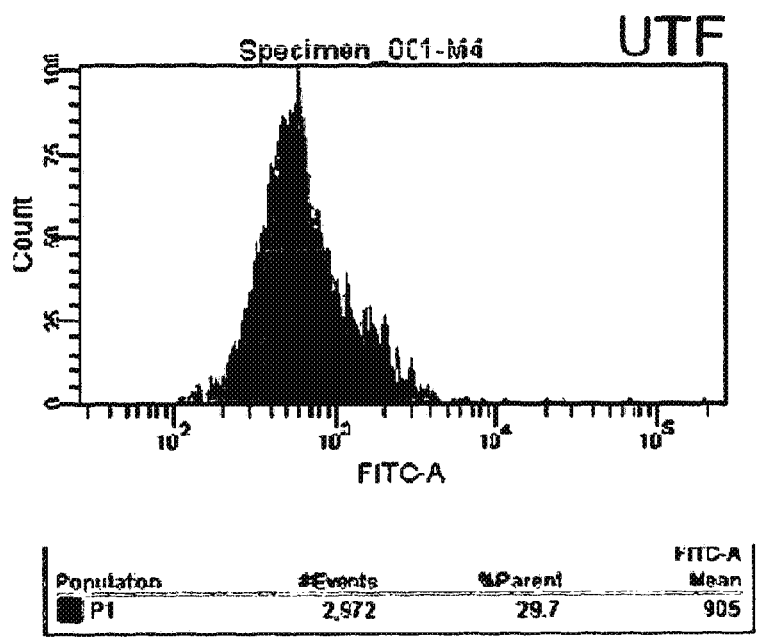

FIG. 9 A-C—FACS evaluation to eliminate cross-reactivity with B2AR

Cells were transiently transfected with either B1AR or B2AR. Mouse and rat sera samples were incubated with cells expressing B1AR, B2AR and untransfected cells and bound sera detected using anti-mouse Alexa Fluor 488 and anti-rat Alexa Fluor 488, respectively. FACS analysis was conducted using a FACS Canto II flow cytometer (BD Bioscience). The mean fluorescence intensity (MFI) was plotted as a bar chart for each sera sample (A) with the histogram profiles for the mouse 4 sera sample depicted in (B,C).

Figure 10:
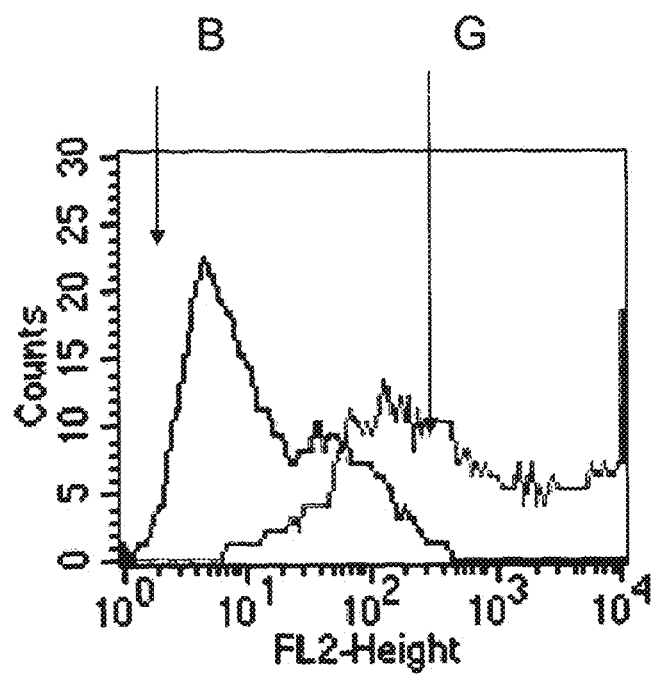

FIG. 10—Confirmation of cell surface expression in HEK293 Cells

NTS1 StaR expression is detected by an anti-tag antibody and represented by the green curve (G); the negative control, an irrelevant cDNA, is represented by the blue curve (B)

FIG. 11 A-B—Evaluation of sera titre in immune response—FACS Analysis:

A. Mice Immunised with StaR cDNA

The green curve represents sera from mice immunised with StaR cDNA binding to NTS1 StaR expressing cells; the blue curve represents the same sera sample binding to wild-type NTS1 expressing cell; the red curve represents cells transfected with an irrelevant cDNA. A significant immune response was observed in the immunised cohorts with the polyclonal sera binding similarly to wild-type and StaR receptor.

B. Mice Immunised with WT Receptor

The green curve represents sera from mice immunised with WT cDNA binding to NTS 1 StaR expressing cells; the blue curve represents the same sera sample binding to wild-type NTS1 expressing cell; the red curve represents cells transfected with an irrelevant cDNA. A significant immune response was observed in the immunised cohorts with the polyclonal sera binding similarly to wild-type and StaR receptor.

Figure 12:
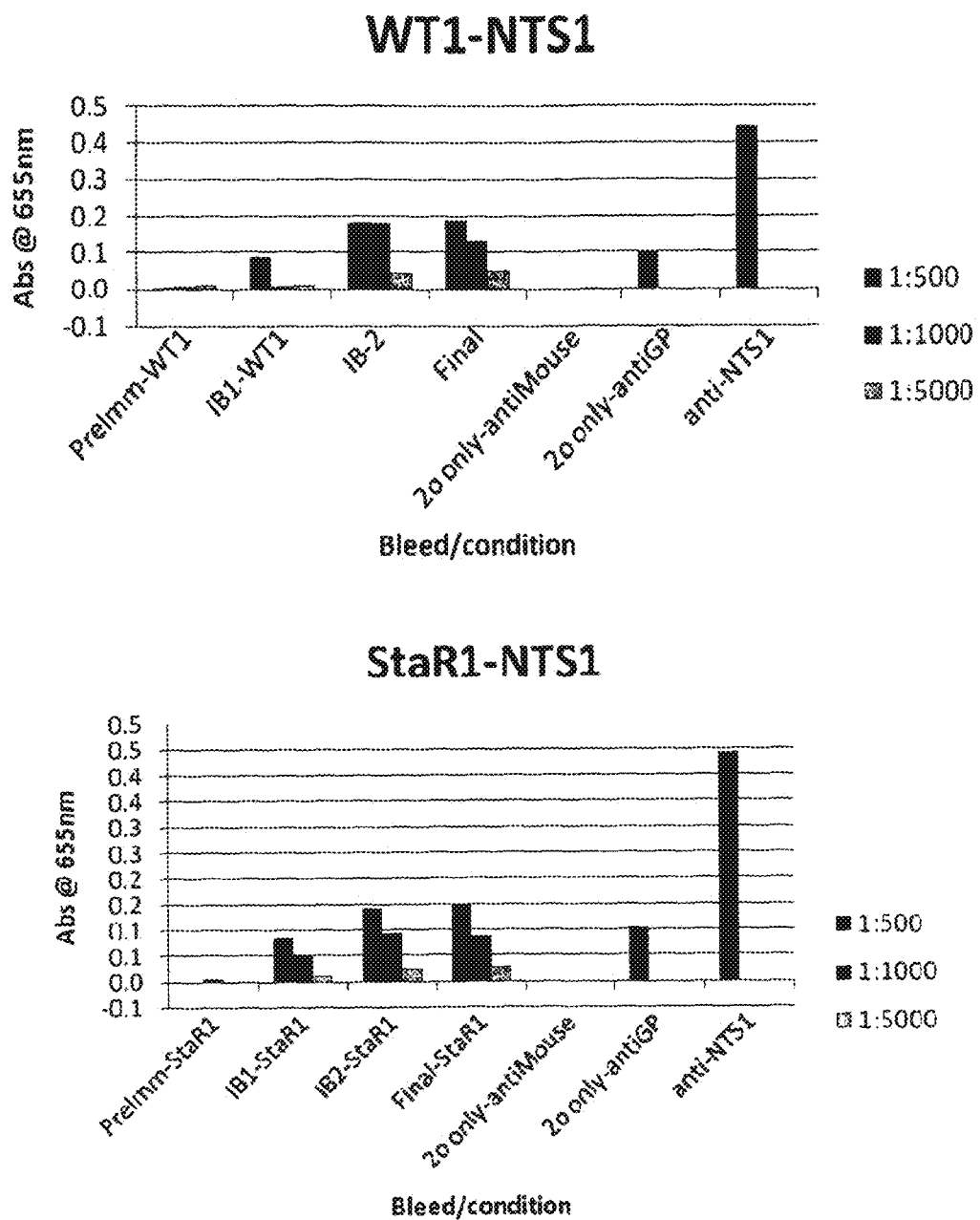

FIG. 12—ELISA analysis

Sera samples were analysed for binding to solubilised membrane preparations of neurotensin receptor immobilised to nickel chelate plate surfaces. Detection was using anti-mouse HRP conjugate with TMB substrate and a positive control was provided by an anti-neurotensin polyclonal that was detected using anti-guinea pig HRP conjugate. The ELISA data reflects the FACS analysis, ie, that the StaR DNA immunisation gave a similar antibody response to the WT DNA immunisation, where an increasing sera titre can be detected throughout the boosting period as shown by interim bleed 1 (IB1), interim bleed 2 (IB2) and the final bleed). Sera samples were evaluated at 3 different dilutions (1:500, 1:1000 and 1:5000).

Figure 13:
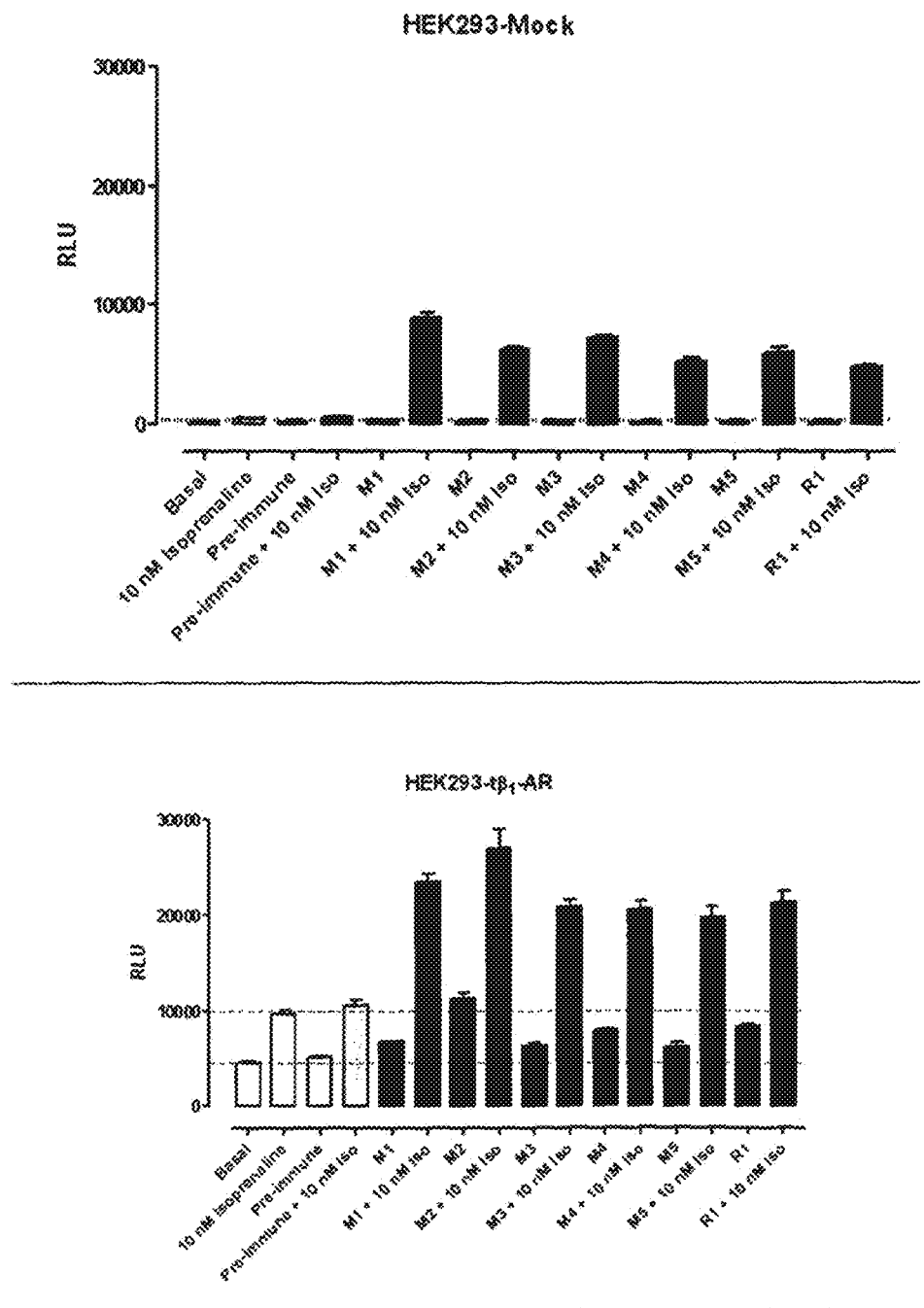

FIG. 13—Mouse and rat polyclonal functional evaluation

Figure 14:
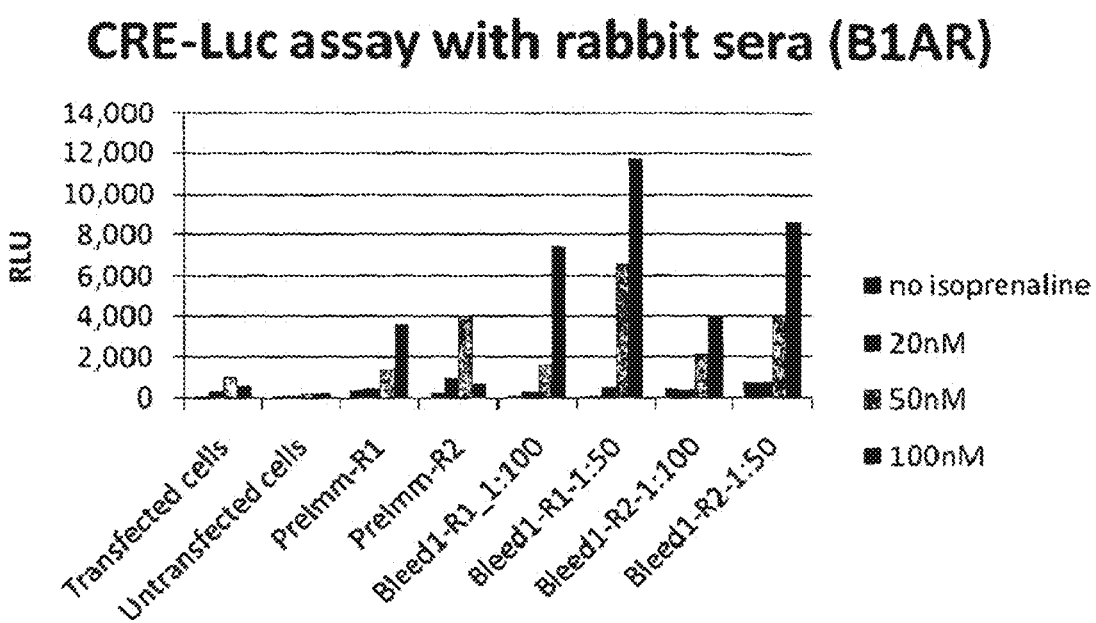

FIG. 14—Rabbit polyclonal functional analysis

Figure 15:
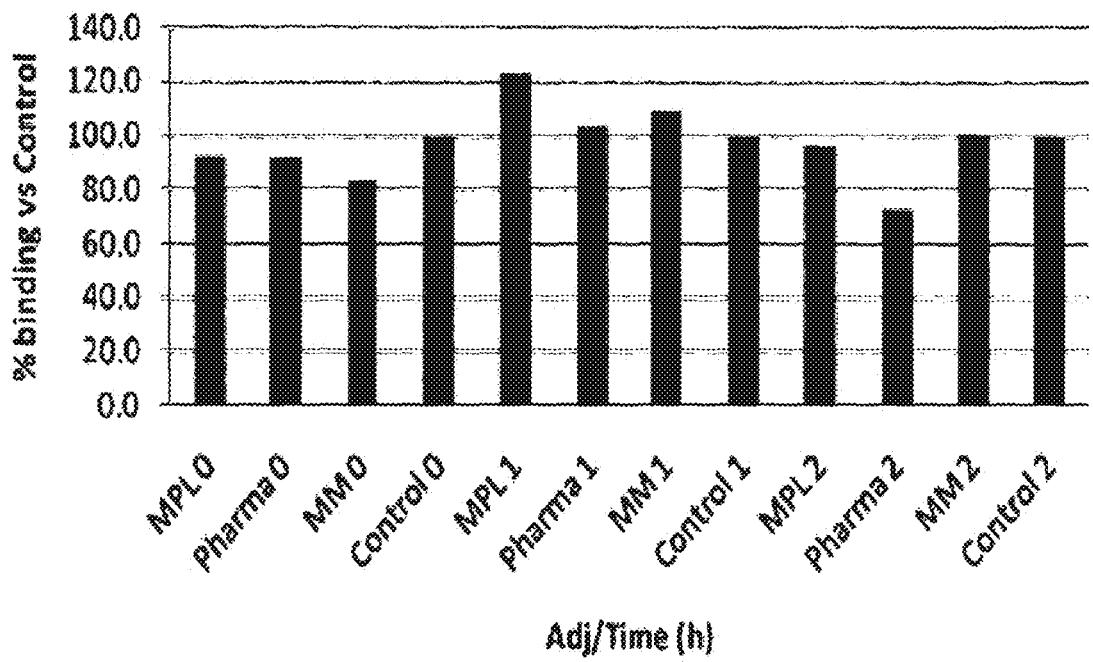

FIG. 15—Stability of β1AR StaR in presence of different adjuvants

FIG. 16—Evaluation of sera titre in immune response by FACS

Preimmune sera samples were compared with interim bleeds to monitor the immune response. The green curve (marked G) represents interim bleed on β1AR StaR expressing cells; the red curve (marked R) represents interim bleed on cells transferred with irrelevant cDNA, and the blue curve (marked B) represents pre-immune bleed on cells transfected with β1AR StaR.

FIG. 17—Evaluation of Sera Titre in Immune Response by ELISA

Figure 18A:
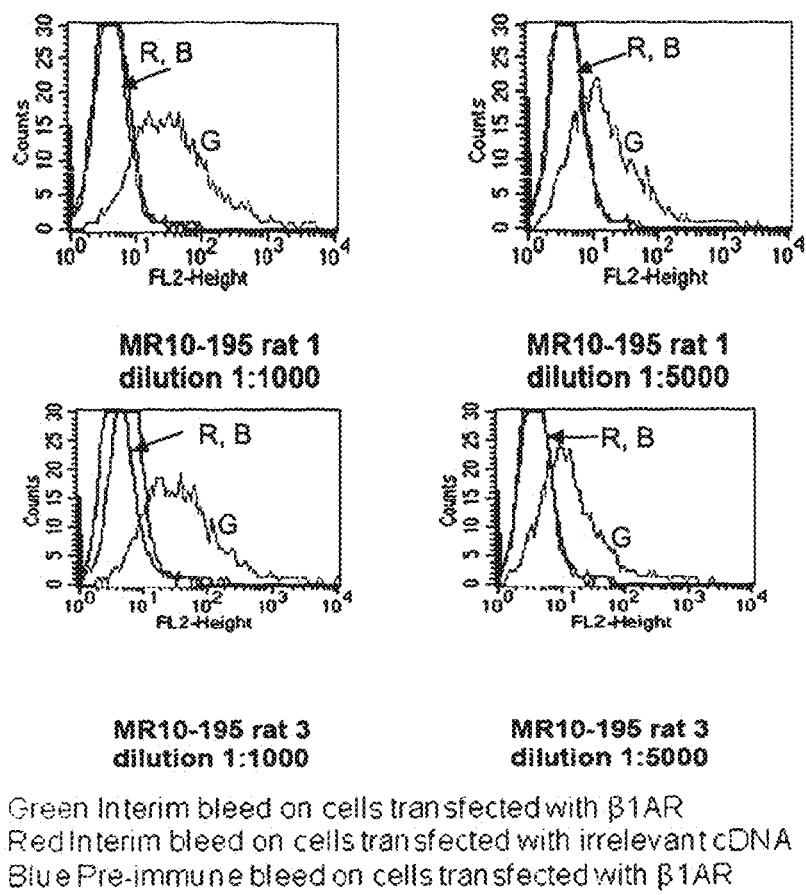
Figure 18B:
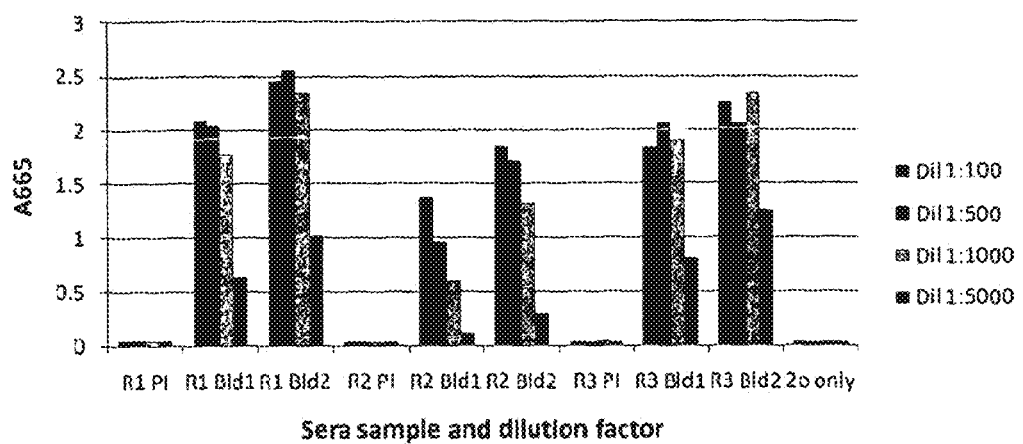

FIG. 18—Evaluation of Sera Titre Following Challenge with 81AR StaR Protein Plus MPL Adjuvant. (A) FACS analysis. The green curve (marked G) represents interim bleed on cells transfected with β1AR; the red curve (marked R) represents interim bleed on cells transfected with irrelevant cDNA; and the blue curve (marked B) represents pre-immune bleed on cells transfected with β1AR. (B) ELISA analysis.

Figure 20:
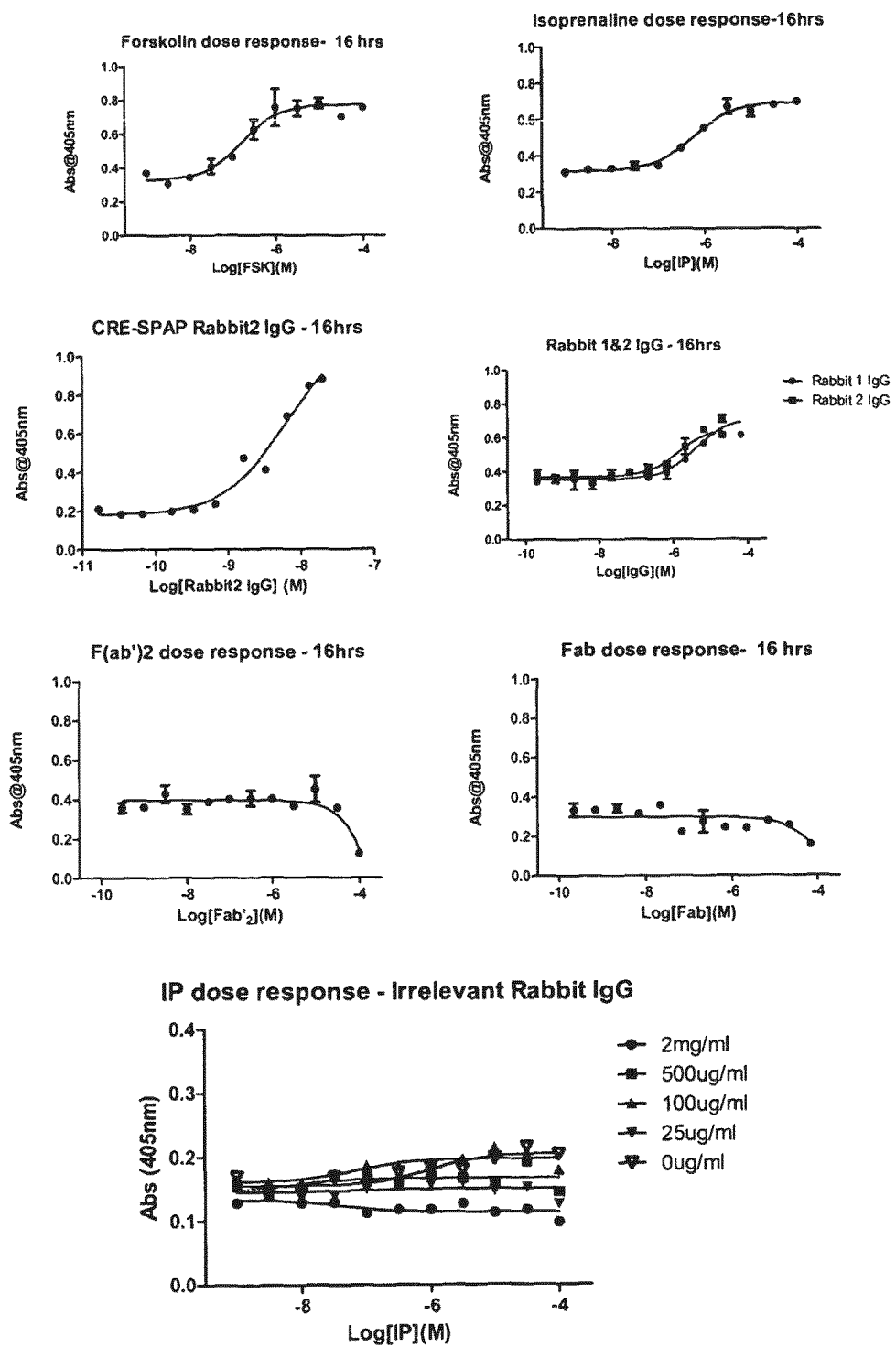
Figure 21:
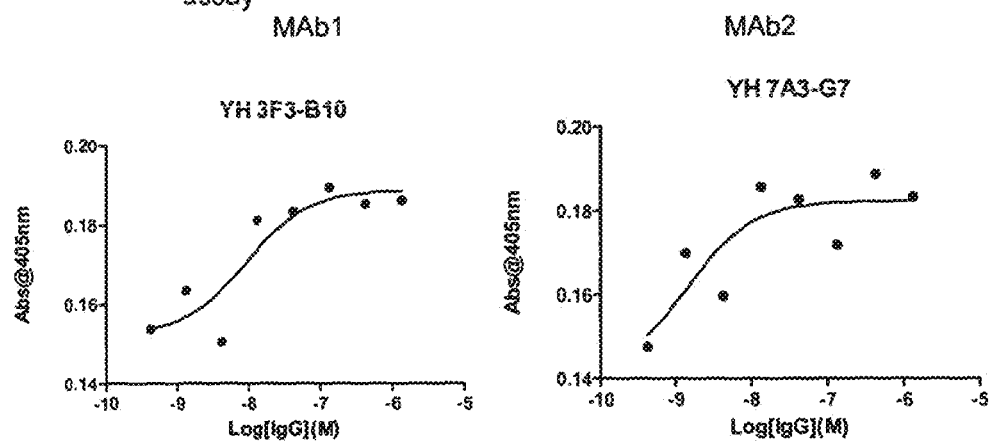
Figure 22:
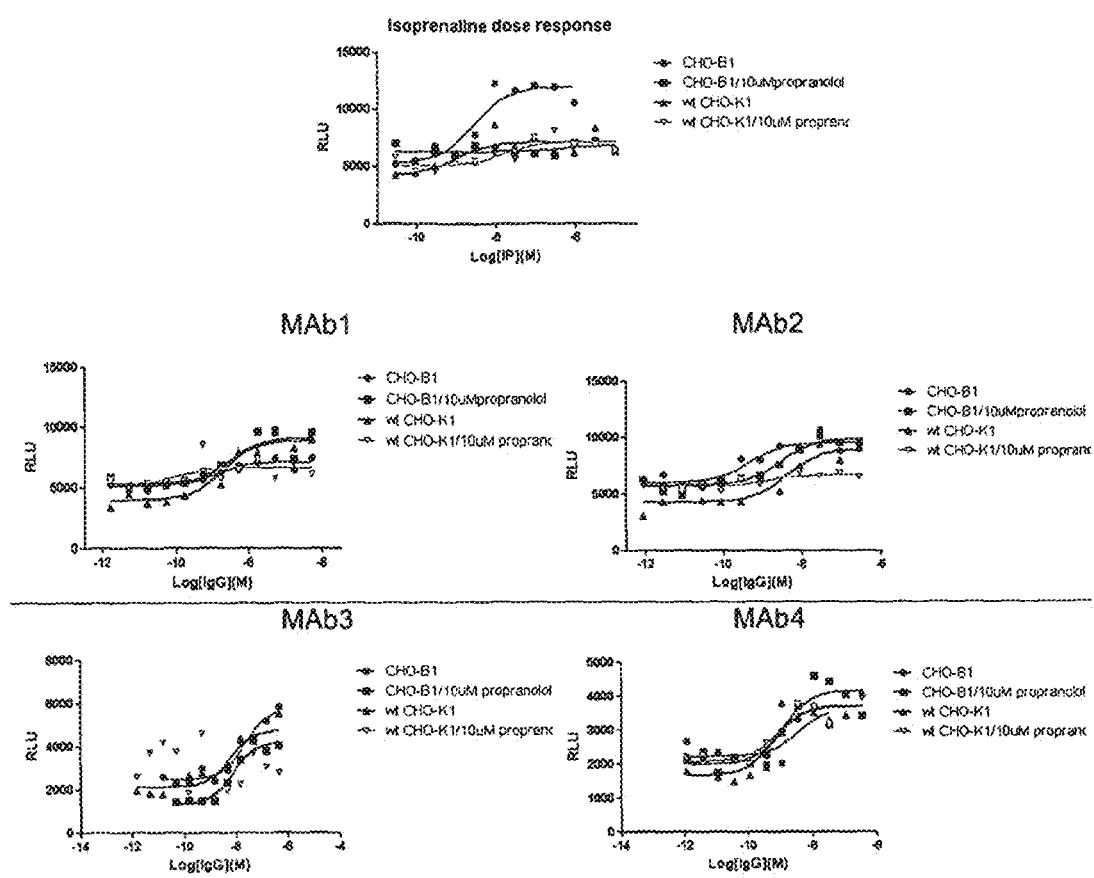
Figure 23:
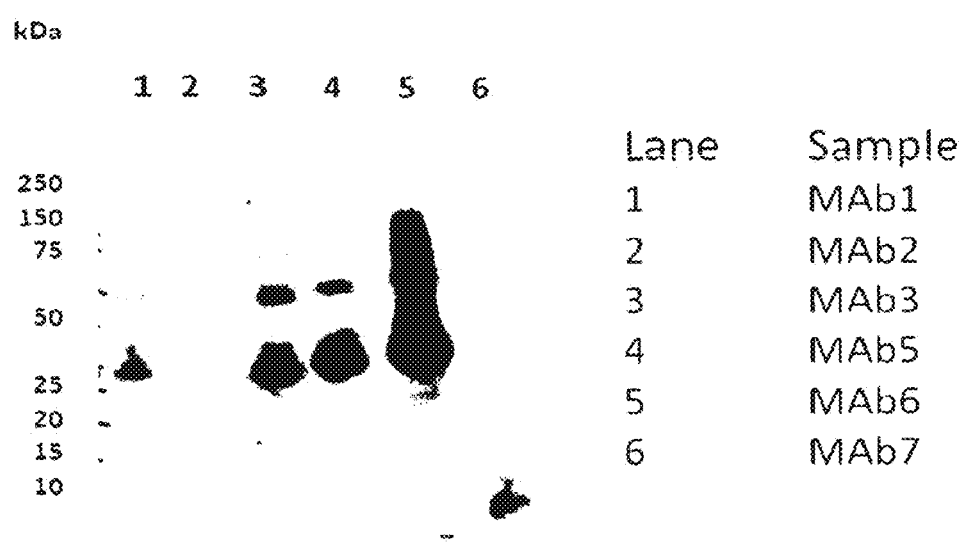
Figure 24:
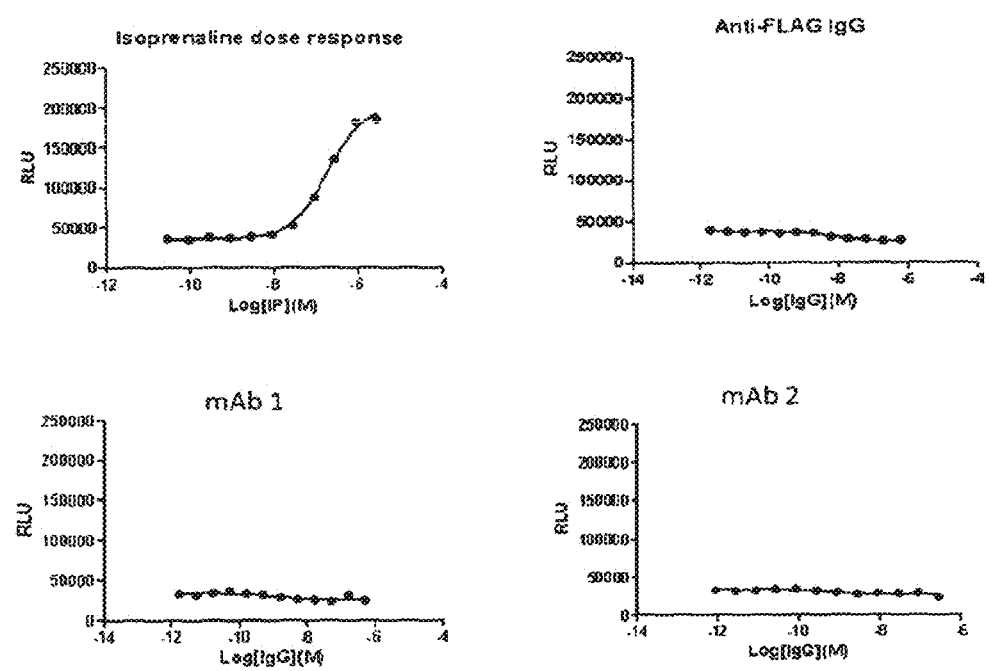
Figure 25:
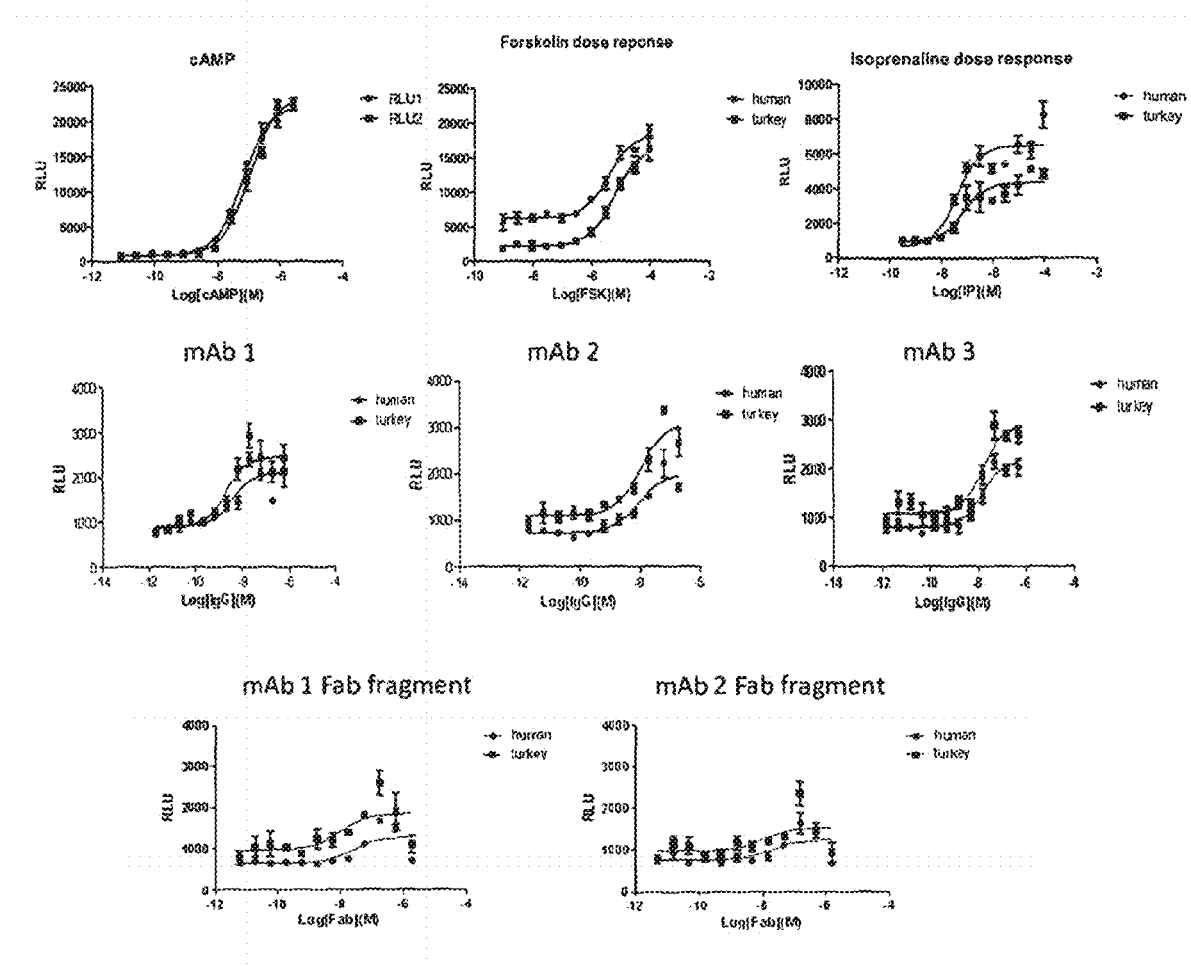

FIG. 19—Evaluation of sera titre in immune response of rabbit by (A) FACS and (B) ELISA FIG. 20—CRE SPAP cAMP evaluation of functional activity on polyclonal IgG and corresponding antibody fragments FIG. 21—Dose response assessment of monoclonal antibodies using the CRE-SPAP cAMP assay FIG. 22—Functional evaluation of monoclonal antibodies in the HitHunter cAMP assay FIG. 23—Western blot analysis to investigate conformational sensitivity FIG. 24—Evaluation of β-arrestin recruitment FIG. 25—Agonist activity with both turkey and human wild type receptors

EXAMPLES

Example 1

Immunisation with β1AR36 m23 StaR

Genetic Immunisation and Boosting with Protein

Figure 4B:
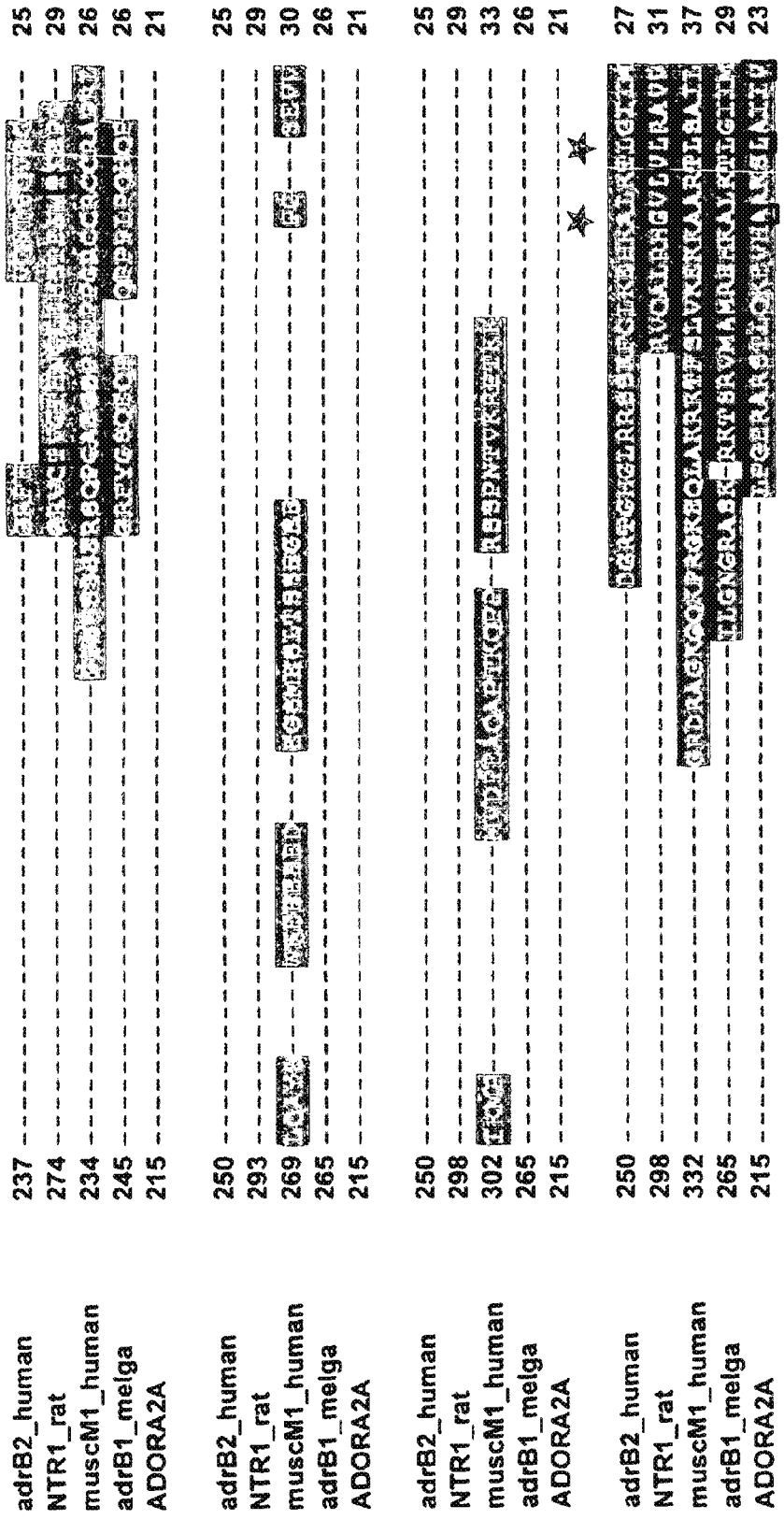
Figure 5:
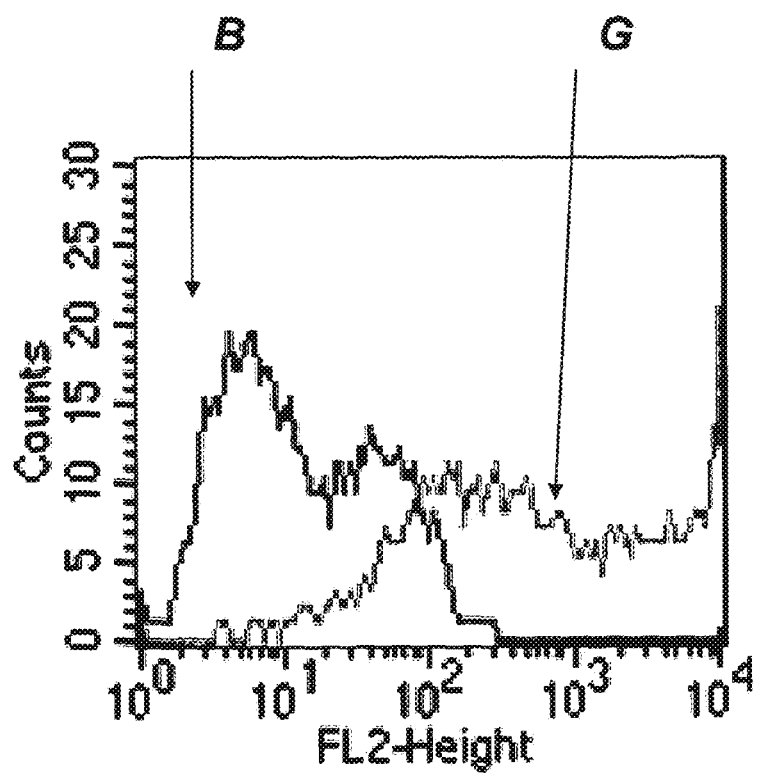
FIG. 5—Confirmation of cell surface expression (HEK293)

The β1AR36 m23 StaR is biased towards a neutral antagonist ground state conformation and as such is capable of signalling and can still produce a full agonist response. The cDNA corresponding to the antagonist conformation of β1AR StaR (Serrano-Vega et al P.N.A.S. vol. 105 (3): 877-882, 2008) was cloned into a genetic immunisation vector (Genovac) and cell surface expression confirmed via transient transfection of HEK293 cells (FIG. 5) prior to intradermal administration via the Gene Gun. The immunisations were conducted by a contract research organisation, Genovac using their proprietary immunisation and screening vectors.

The ovalbumin Th epitope is included in the immunisation vector sequence; this has been optimised for mouse immunisation. In addition, the immunisation and screening vectors differ by their detection tags thereby enabling discrimination between successful expression of immunisation and expression constructs, for example, by FACS analysis of sera on whole cells.

Balb-c mice and Wistar rats were immunised with 50 μg β1AR StaR cDNA construct for the primary challenge, followed by 3-6 boosts of 50 μg cDNA at two-weekly intervals, followed by a further 2-3 boosts using 50 μg purified β1AR StaR protein. Boosting is required for the in vivo affinity maturation by somatic hypermutation of the primary antibody response. The level of immune response was assessed at regular intervals by FACS analysis and ELISA (FIG. 6 and FIG. 7).

Evaluation of Sera Titre in Immune Response by FACS

A pre-immune sera sample (Mouse 1) was compared with an interim bleed to monitor the immune response. The green curve (marked G) represents MAR StaR expressing cells; the red curve (marked R) represents cells transfected with an irrelevant cDNA. A significant immune response was observed in the immunised cohorts (FIG. 6).

Evaluation of Sera Titre in Immune Response by ELISA

His-tagged β1AR StaR (36 m23) was immobilised on a 96-well nickel chelate plate and sera samples diluted for analysis to evaluate binding to β1AR. In mice, boosting with StaR protein maintains titre at the same level or increases titre slightly (FIG. 7).

Immunofluorescence

The immunofluorescence data demonstrates that expression and subcellular localisation of the StaR is similar to that observed with the wild-type receptor (FIG. 8)

FACS Evaluation to Eliminate Cross-reactivity with B2AR

Cells were transiently transfected with either B1AR or B2AR. Mouse and rat sera samples were incubated with cells expressing B1AR, B2AR and untransfected cells and bound sera detected using anti-mouse Alexa Fluor 488 and anti-rat Alexa Fluor 488, respectively.

FACS analysis was conducted using a FACS Canto II flow cytometer (BD Bioscience). The mean fluorescence intensity (MFI) was plotted as a bar chart for each sera sample (A) with the histogram profiles for the mouse 4 sera sample depicted in (B) (FIG. 9). This demonstrated the immune response produced a specific antibody response.

Example 2

Neurotensin Receptor (NTS1) StaR Agonist Conformation

Genetic Immunisation

The NTS1 StaR DNA was cloned into a genetic immunisation vector (Genovac) and cell surface expression confirmed via transient transfection of HEK293 cells (FIG. 6) prior to intradermal administration via the Gene Gun. (Shibata et al *J. Mol. Biol.* (2009) 390, 262-77).

Generally, balb-c mice were immunised with 50 μg NTS1 StaR cDNA construct or with the WT cDNA for the primary challenge, followed by 3-6 boosts of 50 μg cDNA at two-weekly intervals. The level of immune response was assessed at regular intervals by FACS analysis (FIG. 7).

Confirmation of Cell Surface Expression in HEK293 Cells

NTS1 StaR expression is detected by an anti-tag antibody and represented by the green curve (G); the negative control, an irrelevant cDNA, is represented by the blue curve (B) (FIG. 10).

Evaluation of Sera Titre in Immune Response—FACS Analysis:

The green curve represents sera from mice immunised with StaR cDNA binding to NTS1 StaR expressing cells; the blue curve represents the same sera sample binding to wild-type NTS1 expressing cell; the red curve represents cells transfected with an irrelevant cDNA.

Figure 11A:
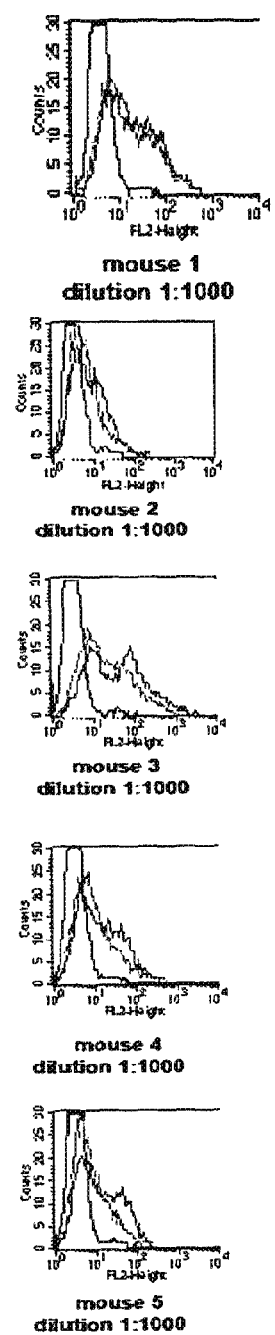

A significant immune response was observed in the immunised cohorts with the polyclonal sera binding similarly to wild-type and StaR receptor. (FIG. 11A)

Mice Immunised with WT Receptor—FACS Analysis:

The green curve represents sera from mice immunised with WT cDNA binding to NTS1 StaR expressing cells; the blue curve represents the same sera sample binding to wild-type NTS1 expressing cell; the red curve represents cells transfected with an irrelevant cDNA.

A significant immune response was observed in the immunised cohorts with the polyclonal sera binding similarly to wild-type and StaR receptor (FIG. 11B).

ELISA Analysis

Sera samples were analysed for binding to solubilised membrane preparations of neurotensin receptor immobilised to nickel chelate plate surfaces. Detection was using anti-mouse HRP conjugate with TMB substrate and a positive control was provided by an anti-neurotensin polyclonal that was detected using anti-guinea pig HRP conjugate.

The ELISA data reflects the FACS analysis, ie, that the StaR DNA immunisation gave a similar antibody response to the WT DNA immunisation, where an increasing sera titre can be detected throughout the boosting period as shown by interim bleed 1 (IB1), interim bleed 2 (IB2) and the final bleed. Sera samples were evaluated at 3 different dilutions (1:500, 1:1000 and 1:5000) (FIG. 12).

Example 3

Functional Data to Show Use of StaR GPCRs as Vaccine

Gene Gun Application

The Gene Gun methodology has been used for a number of vaccination studies. Particle-mediated epidermal delivery (PMED), or the gene gun, is a DNA vaccine delivery technology shown to induce protective levels of antibody and T-cell responses in animals and humans against a wide variety of diseases. This technique is advantageous for generating MAbs and leads to time and resource savings by eliminating the need to express and purify recombinant proteins commonly used for immunizations. Additionally, this approach has been successfully used to generate MAbs to a highly conserved protein. MAbs generated from mice immunized with an expression plasmid encoding human Fc fusion proteins demonstrate a bias toward binding conformational determinants due to the in vivo generation of native antigen. The MAb generation process involves the immunisation or vaccination against the antigen of choice, but then isolating the B cells responsible for secretion of the functional immunoglobulin is necessary.

Furthermore, the generation of hybridomas is required as part of this process or phage display techniques can be employed to create a combinatorial library representing the retrieved repertoire. In vaccination, only an immune response against the target antigen is required, with the host species using its immunoglobulin repertoire to tackle the foreign antigen and fight off disease.

The Gene Gun technology is increasingly being used for the intradermal application of DNA as a vaccination method, for example, this approach has been successfully applied to human and simian immunodeficiency virus epitopes in mice and rhesus macaques (Fuller et al 2007), influenza (Yager et al 2009), hepatitis B (Roberts et al 2005; Loudon et al 2010) and mouse melanoma associated antigens (Surman et al 1998).

Enhancing the Immune Response

In addition, GM-CSF can be co-administered as DNA, ie, a genetic adjuvant, in order to enhance the immune response. This can be species-specific and has been demonstrated to increases mucosal and systemic immunogenicity of an H1N1 influenza DNA vaccine administered into the epidermis of Non-Human Primates (Loudon et al, 2010). Other methods of enhancing the immune response can be used, for example, tetanus (Herrington et al 1987) and diphtheria toxoids (Del Giudice & Rappuoli, 1999) as adjuvants, the use of Th epitopes incorporated as part of the expression construct, as has been shown for the PADRE Th epitope (Ghochikyan et al, 2006) and the ovalbumin Th epitope (Chambers & Johnstone, 2003) in rodents. Other CD4+ epitopes have been identified from patient or immunized populations and implemented in HIV (Ribeiro et al, 2010) and malarial vaccine development (Calvo-Calle et al, 2006), or even more recently developed adjuvants, such as, monophosphoryl lipid A. The strategy used for implementation of the adjuvant could either take the form of genetic components or formulations of compounds that would need to be compatible with StaR integrity.

StaRs as Vaccines

The use of StaR protein or DNA as an effective vaccine can be demonstrated by the functional activity generated in the host's immune response, ie, polyclonal antibodies.

Three species have been immunised primarily via Gene Gun vaccination/immunisation using the β1AR-m23 StaR (Serrano-Vega et al, 2008). This StaR contains 6 point mutations that increase the thermostability of the receptor by 21° C. above the wild-type receptor.

One read-out that can be employed to assess the functional activity of the resulting sera is the impact on cAMP signalling. The CRE-luc reporter assay was employed where the CRE response from activation of AC-cAMP-PKA pathway is the read-out.

Subsequent analysis revealed that the polyclonal sera demonstrated both agonistic synergy with the agonist compound isoprenaline as well as agonist activity alone when the assay was conducted on wild-type B1AR transfected HEK293 cells (FIG. 13). This activity could be detected early on in the immunisation protocol as demonstrated by the data generated from the rabbit analysis (FIG. 14). No activity was detected in any of the pre-immune sera samples.

The first interim bleeds were initially evaluated only on transfected cells to assess if any functional response could be observed at this stage of immunisation. Duplicate data points for both polyclonal sera samples indicate that there are antibody specificities present that confer agonistic activity in synergy with isoprenaline in this preliminary investigation, where 1 μM forskolin stimulation of transfected cells yielded ~40,000 RLU and on non-transfected cells was ~20,000 RLU. Note—this is the first interim bleed, so differences may become more apparent in Rabbit 1 Bleed 2 sera and in the final bleed.

Mouse (M1-M5) and Rat (R1) Polyclonal Functional Analysis

The resulting polyclonal sera can activate wild-type receptors and potentiate receptor response to isoprenaline. This latter effect is also detectable in untransfected HEK293s, where endogenous levels of β1AR are low, suggesting activity at human receptor.

Hence the use of a GPCR of the invention or a GPCR-encoding polynucleotide as a vaccine has been shown to achieve a desired effect, in this case agonism of the receptor.

Example 4

Immunisation with β1AR36 m23 StaR—Further Data

Further experiments based on those described in Example 1 were conducted and the results are discussed below.

Adjuvant/StaR Stability

The B1AR StaR was combined with a number of different adjuvants and investigated for stability at 37° C. over the course of two hours in a ligand binding assay. The adjuvants evaluated were monophosphoryl lipid A (MPL), MM (marketed for generating mouse monoclonals Gerbu) and Pharma (Gerbu). All adjuvants were tested in combination with the StaR protein and demonstrated good stability after 2 hours incubation as compared with the control sample, suggesting compatibility with StaR immunogen at body temperature (FIG. 15).

Repeat B1AR Study (DNA+Protein) to Demonstrate Strategy is Robust and Reproducible The repeat β1AR study was to demonstrate that this approach is reproducible for generating agonistic polyclonal sera and identifying positive hybridomas. Changes were implemented from the initial study (see Example 1) using a shorter more stringent immunisation protocol. Balb-c mice and Wistar rats underwent genetic immunization using the Gene Gun for the initial DNA priming and boosting (4×50 μg DNA), followed by a shorter boosting phase using protein (2×50 μg StaR protein). Interim bleeds were taken at this stage and binding profiles assessed by FACS and ELISA.

Second Sera Test FACS:

The rat cohort exhibited a stronger immune response than observed in the first study and the mouse cohort also showed a robust immune response as determined by FACS. Both cohort sera samples also demonstrated specificity as evaluated by binding profiles on B1AR expressing cells and cells expressing an irrelevant cDNA, with no background binding detected in pre-immune sera (FIG. 16).

Second Sera Test ELISA

It can be clearly observed from Bleed 1 to Bleed 2 that the effect of the StaR protein boost has had a strong positive impact on the sera titre in both cohorts as evaluated by ELISA (FIG. 17).

B1AR StaR Protein Plus MPL Adjuvant—FACS and ELISA

B1AR StaR protein was formulated in MPL adjuvant using a 1:1 ratio. Balb-c mice and Wistar rats were immunized by intraperitonel injection where the immunization protocol used protein priming and boosting to Interim Bleed 1 (4×50 μg StaR protein), followed by a shorter boosting phase using protein to Interim Bleed 2 (2×50 μg StaR protein). A significant immune response was observed (FIG. 18).

Functional Antibody Response Also Generated in Rabbits

Agonistic antibodies have also been generated in a third host species (New Zealand White rabbits) using the genetic immunization strategy only (Gene Gun). The initial DNA challenge plus standard boosting was followed by second short boosting period. Sera were assessed for binding to B1AR by ELISA and FACS (FIG. 19), as well as functional evaluation in the cell-based CRE-luciferase reporter assay (FIG. 14). A robust immune response was seen with functional activity being detected as early as the first interim bleed. The sera demonstrate agonistic activity in synergy with isoprenaline.

Example 5

Functional Data to Show Use of StaR GPCRs as Vaccine

Experiments to characterise the functionality of both polyclonal and monoclonal antibodies are described below.

CRE-SPAP cAMP Assay

Agonist activity of the IgG can be demonstrated in a variety of assay formats used to measure increases in cAMP. An alternative assay to the CRE-luciferase receptor assay (see Examples 3 and 4) is the CRE-SPAP (secreted placental alkaline phosphatase) reporter assay. SPAP is secreted from cells so it can be measured by sampling the culture media and can be separated from endogenous alkaline phosphatases due to its thermal stability. The method used is briefly described as follows:

Cells, media: Chinese hamster ovary (CHO) cells stably expressing a CRE-SPAP reporter gene and wild type turkey $\beta_1$ receptor were grown to confluence in 96-well plates. Once confluent, the media were removed and replaced with 100 μl of serum-free media (ie, DMEM/F12 containing 2 mM L-glutamine), and the cells were incubated for a further 24 hrs at 37° C. in 5% $CO_2$.

Method: On the day of experimentation, the serum-free media was removed and replaced with 100 μl of serum-free media/100 μM IBMX or 100 μl of serum-free media/100 μM containing antagonists at the final required concentration, and the cells were incubated for 30 min at 37° C./5% $CO_2$. Ten microliters of agonist (diluted in serum free media) were then added to each well, and the plate was incubated at 37° C./5% $CO_2$ for 5-16 hrs.

Evaluation of Polyclonal Antibodies

The CRE-SPAP assay was used to assess functional activity of purified rabbit polyclonal IgG. After 16 hrs, the media and ligand/antibody were removed, 40 μl of serum-free media (no IBMX) were added to each well, and the cells were incubated for a further 1 hr at 37° C. The plates were then incubated at 65° C. for 30 min to destroy any endogenous phosphatases. The plates were then cooled to 37° C. One hundred microliters of 5 mM 4-nitrophenyl phosphate (Sigma) was added to each well, and the plates were incubated at 37° C. until the yellow colour developed. The plates were then read on Polar Star plate reader at 405 nm. Forskolin and isoprenaline were included in parallel as controls. The data in FIG. 20 represents experiments performed in duplicate and analysed using GraphPad Prism.

Both polyclonal IgG samples demonstrate agonistic activity. However, the corresponding F(ab')$_2$/Fab antibody fragments generated by enzymatic digestion showed no sign of agonistic activity, with a decrease of absorbance at the highest sample concentration. This decrease may be due to protein aggregation at a high protein concentration. As a control, no functional activity was detected for an irrelevant rabbit IgG in the same assay, either in the presence or absence of isoprenaline as would be expected.

The data suggests that the full-length antibody is necessary for agonist functional activity. Supporting evidence that bivalent intact IgG mediate receptor cross-linking/dimerisation is provided by a recent report that describes the evaluation of autoantibodies (in the form of polyclonal immunoglobulin G) to M2 muscarinic acetylcholine receptor in Chagas' disease (Beltrame et al, 2011). Agonist functional activity was observed as assessed by BRET, however the corresponding Fab fragment (monovalent) did not produce this effect.

Evaluation of Monoclonal Antibodies

The CRE-SPAP assay has also been used to analyse monoclonal antibodies generated from the hybridoma fusions. At least two monoclonals derived from a DNA+protein immunisation strategy in mice demonstrated agonist functional activity (FIG. 21). It should be noted that in order to retrieve monoclonal specificities responsible for a high level of functional response observed in the polyclonal samples, a greater number of fusions could be conducted as well as many more hybridoma clones created and screened.

HitHunter XS+ cAMP Assay

The DiscoveRX HitHunter assay kit uses the enzyme fragment complementation (EFC) technology with two fragments of *E. coli* β-galactosidase: a large protein fragment (enzyme acceptor, EA) and a small peptide fragment (enzyme donor, ED). Separately, these fragments are inactive, but in solution they rapidly complement to form active β-gal enzyme, which can hydrolyze substrate to produce a luminescent signal. In this assay, cAMP from cell lysates and ED-labeled cAMP compete for antibody binding sites. Unbound ED-cAMP is free to complement EA to form active enzyme, which subsequently produces a luminescent signal. The amount of signal produced is directly proportional to the amount of cAMP in the standard or cell lysate.

Cells were plated in 96-well format at densities of 25,000 cells/well and the 2 Reagent Addition Protocol was used for cAMP standard and sample measurement. The observed trend represents three separate experiments with all data analysed using GraphPad Prism.

Evaluation in this assay format revealed a number of mouse monoclonal IgG clones that exhibited agonist activity (FIG. 22). The mAbs possessing the greatest agonist activity, with low nanomolar EC$_{50}$ potencies of 0.5-1.5 nM, were all derived from the DNA+protein immunisation study. This includes the apparent conformationally sensitive antibody MAb2 (as deduced by Western analysis, ie, no binding observed, refer to FIG. 23).

It is evident that the potency of a number of the mAbs is significantly greater than that of the polyclonal IgG preparation, reflecting the bias or proportion of particular specificities responsible for the functional activity within the polyclonal sera versus the single specificity of a monoclonal antibody.

Monoclonal mouse and rat IgGs were analysed by Western blot to identify potential conformationally sensitive antibodies. Truncated (no N terminus present), purified β$_1$AR-36M23 was diluted 1000-fold to 14 μg/ml and 22 μl of that sample was mixed with 2 μl 1M DTT with 8 μl 4×LDS Sample buffer, loaded into 4-20% Tris-Glycine SDS PAGE and subjected to electrophoresis. The gel was transferred onto nitrocellulose membrane and binding detected with monoclonal IgG at 10 μg/ml concentration and secondary anti-mouse or anti-rat HRP conjugates.

The Western blot analysis shown in FIG. 23 reveals that one mouse IgG (MAb2—Lane 2) did not show any binding. All the other IgGs bound to the truncated β$_1$AR in the Western analysis suggesting that these monoclonal IgGs bind to a linear epitope. MAb2 is probably a conformationally sensitive IgG, which binds to the native full length (FACS) or truncated (ELISA) receptor, but not to the denatured (Western) protein. All the other IgG bound to the native protein in ELISA as well.

Ablating Agonist Activity with the Antagonist Propranolol

Further functional evaluation was investigated in parallel to assess if agonist activity could be ablated by an antagonist, such as propranolol. The data shown in FIG. 22 clearly demonstrates that the isoprenaline dose response can be significantly decreased with 10 μM propranolol, with a distinct shift to the right for all the four mAbs in the presence of propanolol. In addition, it can also be observed that there appears to be a low level of endogenous activity on non-transfected CHO-K1 cells that is also ablated by propranolol.

Example 6

Functional Data to Show Use of StaR GPCRs as Vaccine

PathHunter β-Arrestin Evaluation:

This Example describes the use of the DiscoveRX PathHunter assay kit for the evaluation of β-arrestin recruitment. This screening assay measures receptor activation via G-protein dependent and independent signalling, as GPCR mediated β-arrestin signalling may occur regardless of G-protein coupling, and is an enzyme fragment complementation method. It is possible to identify agonism, antagonism and allosteric modulation if the receptor recruits β-arrestin.

Cells, Media:

Pre-validated frozen cell-division arrested cells stably transfected with both wild type human β$_1$AR and β-arrestin (Product code: 93-0488E2) were supplied with the assay kit (Product code: 93-0446E1). These were plated in 100 μl/well proprietary media supplied with the kit (Optimised Cell Culture media) according to the manufacturer's recommendations. Cells were incubated at 37° C./5% CO$_2$ for 24 hrs prior to the assay.

Ligands, Antibodies:

Ligands and IgG samples were prepared on the day of the assay; all dilutions were made in the media supplied with the kit. Forskolin and isoprenaline were used as positive controls and anti-FLAG mouse mAb was used for the negative control.

Method:

Half-log dilutions (12 data points) of the ligands and mAbs were made in 10 μl proprietary media and added directly to the cells, which were already in 100 μl culture media. Cells were incubated for 90 minutes at 37° C./5% CO$_2$. 55 μl of working detection reagent was added to the wells and plates were incubated at RT for 90 min. Luminescence was read on a Polar Star plate reader and data analysed using GraphPad Prism.

The resulting data shown in FIG. 24 demonstrates that isoprenaline is able to recruit β-arrestin as previously shown (Andresen, 2011); neither the negative control antibody (anti-FLAG) nor the mAb panel showed activity, suggesting that activation of the receptor by the mAb, which leads to stimulation of cAMP, does not result in recruitment of β-arrestin. This dissociation between G protein activation (leading to cAMP signalling) and β-arrestin recruitment is known as biased agonism (Andresen, 2011). It suggests that the mAb stabilises a different active conformation to isoprenaline.

Evaluation cAMP Stimulation Using Human $\beta_1$AR Transfected Cells:

This assessment verified that the lack of activity in the β-arrestin assay was because the mAb panel shows pathway selectivity, rather than due to species differences between turkey receptor (used in the previous studies) and human $\beta_1$AR (as there is only ~60% sequence homology).

The HitHunter XS+cAMP assay was used as described previously, utilising both Chinese hamster ovary (CHO) cells stably expressing wild type turkey $\beta_1$ receptor and CHO cells transiently transfected with wild type human $\beta_1$ receptor. Intact IgG and the corresponding Fab fragments were evaluated.

The data in FIG. 25 clearly demonstrates that a mAb that can agonise the turkey $\beta_1$ receptor can also agonise the human $\beta_1$ receptor. This adds further credence to previous observations made with polyclonal sera on endogenous human $\beta_1$ receptor (FIG. 13). In addition, it was also confirmed that the dimeric intact IgG format was necessary for agonism, as agonist activity for the monomeric Fab format was either ablated or greatly reduced. This outcome also confirms the observation that the mAb panel stimulates cAMP production but not β-arrestin recruitment.

Another observation is that the agonist maximal response observed with the human receptor is not as high as that observed for the turkey receptor (which was used as the antigen for immunisation). This may reflect sequence differences between the two species of receptor. Such an effect has been described in a pharmacological evaluation that used correlation analysis of the log $K_D$s from a large panel of ligands to the human and turkey $\beta_1$ receptors to assess differences and similarities (Baker et al 2010). Alternatively, this may be due to differences in receptor expression or coupling efficiency to signalling pathways

REFERENCES

1. S. H. White (2004) *Protein Sci* 13, 1948-1949.
2. C. G. Tate (2001) *FEBS Lett* 504, 94-98.
3. R. Grisshammer, C. G. Tate (1995) *Q Rev Biophys* 28, 315-422.
4. J. U. Bowie (2001) *Curr Opin Struct Biol* 11, 397-402.
5. F. W. Lau, S, Nauli, Y. Zhou, J. U. Bowie (1999) *J Mol Biol* 290, 559-564.
6. Y. Zhou, J. U. Bowie (2000) *J Biol Chem* 275, 6975-6979.
7. S. Faham, D. Yang, E. Bare, S. Yohannan, J. P. Whitelegge, J. U. Bowie (2004) *J Mol Biol* 335, 297-305.
8. Y. Yarden, H. Rodriguez, S. K. Wong, D. R. Brandt, D. C. May, J. Burnier, R. N. Harkins, E. Y. Chen, J. Ramachandran, A. Ullrich, et al (1986) *Proc. Natl. Acad. Sci. USA* 83, 6795-6799.
9. T. Warne, J. Chirnside, G. F. Schertler (2003) *Biochim Biophys Acta* 1610, 133-140.
10. E. M. Parker, E. M. Ross (1991) *J Biol Chem* 266, 9987-9996.
11. E. M. Parker, K. Kameyama, T. Higashijima, E. M. Ross (1991) *J Biol Chem* 266, 519-527.
12. W. J. Degrip (1982) *Methods in Enzymology* 81, 256-265.
13. K. Palczewski, T. Kumasaka, T. Hori, C. A. Behnke, H. Motoshima, B. A. Fox, I. Le Trong, D. C. Teller, T. Okada, R. E. Stenkamp, et al (2000) Science 289, 739-745.
14. J. Li, P. C. Edwards, M. Burghammer, C. Villa, G. F. Schertler (2004) *J Mol Biol* 343, 1409-1438.
15. R. Jaenicke, G. Bohm (1998) *Current Opinion in Structural Biology* 8, 738-748.
16. J. Tucker, R. Grisshammer (1996) *Biochem J* 317 (Pt 3), 891-899.
17. W. Schaffner, C. Weissmann (1973) *Anal. Biochem.* 56, 502-514.
18. C. G. Tate (1998) *Methods Enzymol* 296, 443-455.
19. H. M. Weiss, R. Grisshammer (2002) *Eur J Biochem* 269, 82-92.
20. Rasmussen, S. G., Choi, H. J., Rosenbaum, D. M., Kobilka, T. S., Thian, F. S., Edwards, P. C., Burghammer, M., Ratnala, V. R., Sanishvili, R., Fischetti, R. F., Schertler, G. F., Weis, W. I. and Kobilka, B. K. (2007) *Nature* 15, 383-387.
21. Cherezov, V., Rosenbaum, D. M., Hanson, M. A., Rasmussen, S. G., Thian, F. S., Kobilka, T. S., Choi, H. J., Kuhn, P., Weis, W. I., Kobilka, B. K. and Stevens, R. C. (2007) *Science* 318:1258-1265.
22. Minneman, K. P., Weiland, G. A. and Molinoff, P. B. (1980) *Mol Pharmacol* 17:1-7.
23. Parker, E. M., Swigart, P., Nunnally, M. H., Perkins, J. P. and Ross, E. M. (1995) *J Biol Chem* 270:6482-6487.
24. Schofield D J, Pope A, Clementel V, Buckell J, Chapple S D J, Clarke K F, Conquer J S, Crofts A M, Crowther S R E, Dyson M R, Flack G, Griffin G J, Hooks Y, Howat W J, Kolb-Kokocinski A, Kunze S, Martin C D, Maslen G L, Mitchell J M, O'Sullivan M, Perera R L, Roake W, Shadbolt S P, Vincent K J, Warford A, Wilson W E, Xie J, Young J L, McCafferty J (2007) Application of phage display to high throughput antibody generation and characterisation. Genome Biology. 8 (11) R254
25. Chapple S D, Crofts A M, Shadbolt S P, McCafferty J, Dyson M R. (2006) Multiplexed expression and screening for recombinant protein production in mammalian cells. BMC Biotechnol. 2006 Dec. 22; 6:49. http://www.biomedcentral.com/1472-6750/6/49
26. Martin C, Rojas G, Mitchell J N, Vincent K J, Wu J, McCafferty J, Schofield D J (2006) A simple vector system to improve performance and utilisation of recombinant antibodies. BMC Biotechnology 6:46 doi:10.1186/1472-6750-6-46 http://www.biomedcentral.com/1472-6750/6/46/abstract
27. Warne et al (2008) Structure of a β adrenergic G protein coupled receptor Nature 454: 486-491
28. Francesca Magnani, Yoko Shibata, Maria J. Serrano-Vega, and Christopher G. Tate Proc Natl Acad Sci USA. (2008) 105, 10744-10749. Co-evolving stability and conformational homogeneity of the human adenosine $A_{2a}$ receptor
29. Maria J. Serrano-Vega, Francesca Magnani, Yoko Shibata, and Christopher G. Tate Proc Natl Acad Sci USA. (2008) 105, 877-882. Conformational thermostabilization of the β1-adrenergic receptor in a detergent-resistant form
30. Yoko Shibata, Jim F. White, Maria J. Serrano-Vega, Francesca Magnani, Amanda L. Aloia, Reinhard Grisshammer and Christopher G. Tate J Mol Biol (2009) 390, 262-77. Thermostabilization of the neurotensin receptor NTS1
31. Anja Müller, Bernhard Homey, Hortensia Soto, Nianfeng Ge, Daniel Catron, Matthew E Buchanan, Terri McClanahan, Erin Murphy, Wei Yuan, StephenN Wagner, Jose Luis Barrera, Alejandro Mohar, Emma Verastegui and Albert Slotnik Nature (2001) 410, 50-56.
32. Involvement of chemokine receptors in breast cancer metastasis
33. Barbara Ingold, Eva Simon, Ute Ungethum, Ralf-Jürgen Kuban, Berit M. Müller, Amelie Lupp, Ulf Neumann, Matthias P. A. Ebert, Carsten Denkert, Wilko Weichert, Stefan Schulz, Christoph
34. Röcken PLoS one (2010) 5 (April) e10087. Vascular CXCR4 expression—a novel antiangiogenic target in gastric cancer?
35. Hyun Kyung Kim, Maria De La Luz Sierra, Cassin Kimmel Williams, A. Virginia Gulino, and Giovanna Tosato Blood (2006)108, 812-820. G-CSF down-regulation of CXCR4 expression identified as a mechanism for mobilization of myeloid cells
36. Hiroshi Tsutsumi, Hirokazu Tamamura and Nobutaka Fujii. Letters in Drug Design & Discovery (2007) 4, 20-26. Inhibitors of the chemokine receptor CXCR4: chemotherapy of AIDS, metastatic cancer, leukemia and rheumatoid arthritis
37. Mark L Cannon and Ethels Cesarman Oncogene (2004) 23, 514-523. The KSHV G protein-coupled receptor signals via multiple pathways to induce transcription factor activation in primary effusion lymphoma cells
38. Sarah J. Paulsen, Mette M. Rosenkilde, Jesper Eugen-Olsen, and Thomas N. Kledal J Virology (2005) 79, 536-546. Epstein-Barr Virus-Encoded BILF1 Is a Constitutively Active G Protein-Coupled Receptor
39. David Lembo, Manuela Donalisio, Anders Hofer, Maura Cornaglia, Wolfram Brune, Ulrich Koszinowski, Lars Thelander, and Santo Landolfo J Virology (2004) 78, 4278-4288. The Ribonucleotide Reductase R1 Homolog of Murine Cytomegalovirus Is Not a Functional Enzyme Subunit but Is Required for Pathogenesis
40. Jay Doniger, Sumitra Muralidhar, and Leonard J. Rosenthal Clin Microbiol Rev (1999) 12, 367-82. Human cytomegalovirus and human herpesvirus 6 genes that transform and transactivate
41. Smit M J, Vink C, Verzijl D, Casarosa P, Bruggeman C A, Leurs R. Current Drug Targets (2003) 4, 431-41. Virally encoded G protein-coupled receptors: targets for potentially innovative anti-viral drug development
42. Edward A. Berger, Philip M. Murphy and Joshua M. Farber. Annu Rev Immunol (1999) 17, 657-700. Chemokine receptors as HIV-1 coreceptors: roles in viral entry, tropism, and disease
43. Birgitt Dau and Mark Holodniy. Drugs (2009) 69, 31-50. Novel targets for antiretroviral therapy
44. Michel Samson Frédérick Libert Benjamin J. Doranz Joseph Rucker Corinne Liesnard Claire-Michèle Farber Sentob Saragosti Claudine Lapouméroulie Jacqueline Cognaux Christine Forceille Gaetan Muyldermans Chris Verhofstede Guy Burtonboy Michel Georges Tsuneo Imai Shalini Rana Yanji Yi Robert J. Smyth Ronald G. Coltman Robert W. Doms Gilbert Vassart & Marc Parmentier Nature (1996) 382, 722-725. Resistance to HIV-1 infection in caucasian individuals bearing mutant alleles of the CCR-5 chemokine receptor gene
45. Jeffrey M. Jacobson, Michael S. Saag, Melanie A. Thompson, Margaret A. Fischl, Ralph Liporace, Richard C. Reichman, Robert R. Redfield, Carl J. Fichtenbaum, Barry S. Zingman, Mahesh C. Patel, Jose D. Murga, Suzanne M. Pemrick, Paul D'Ambrosio, Marti Michael, Hans Kroger, Hieu Ly, Yakov Rotshteyn, Robert Buice, Stephen A. Morris, Joseph J. Stavola, Paul J. Maddon, Alton B. Kremer, and William C. Olson J Infect Diseases (2008) 198, 1345-52. Antiviral Activity of Single-Dose PRO140, a CCR5 Monoclonal Antibody, in HIV-Infected Adults
46. William Olson and Jeffrey Jacobson. Curr Opin HIV & AIDS (2009) 4, 104-111. CCR5 monoclonal antibodies for HIV-1 therapy
47. Amit Mor, Eugenia Segal, Brenda Mester, Boris Arshava, Osnat Rosen, Fa-Xiang Ding, Joseph Russo, Amnon Dafni, Fabian Schvartzman, Tali Scherf, Fred Naider, and Jacob Anglister Biochemistry (2009)48, 3288-3303. Mimicking the structure of the V3 epitope bound to HIV-1 neutralizing antibodies
48. Jean K. Lim, Christine Y. Louie, Carol Glaser, Cynthia Jean, Bernard Johnson, Hope Johnson, David H. McDermott, and Philip M. Murphy J Infect Dis (2008) 197, 262-265. Genetic deficiency of chemokine receptor CCR5 is a strong risk factor for symptomatic West Nile virus infection: a meta-analysis of 4 cohorts in the US epidemic
49. Elin Kindberg, Aukse Mickiene, Cecilia Ax, Britt Åkerlind, Sirkka Vene, Lars Lindquist, Åke Lundkvist, and Lennart Svensson. J Infect Dis (2008) 197, 266-269. A deletion in the chemokine receptor 5 (CCR5) gene is associated with tickborne encephalitis
50. W James Cook, Martha F Kramer, Russell M Walker, Timothy J Burwell, Holly A Holman, Donald M Coen and David M Knipe. Virol J (2004) 1:5 Persistent expression of chemokine and chemokine receptor RNAs at primary and latent sites of herpes simplex virus 1 infection
51. Carlos A Guerra, Robert W Snow & Simon I Hay. Adv Parasitol (2006) 62, 157-179. Defining the global spatial limits of malaria transmission in 2005
52. Kamini Mendis, Barbara J Sina, Paola Marchesini & Richard Carter. Am J Trop Med Hyg (2001) 64, 97-106. The neglected burden of *Plasmodium vivax* malaria
53. Christophe Tournamille, Yves Colin, Jean Pierre Cartron & Caroline Le Van Kim C. Nat Genet (1995) 10, 224-228. Disruption of a GATA motif in the Duffy gene promoter abolishes erythroid gene expression in Duffy-negative individuals
54. Peter J. Mc Guire, Charlotte Cunningham-Rundles, Hans Ochs and George A. Diaz Clin Immunol (2010) in press Oligoclonality, impaired class switch and B-cell memory responses in WHIM syndrome
55. Bernard Lagane, Ken Y. C. Chow, Karl Balabanian, Angélique Levoye, Julie Harriague, Thierry Planchenault, Françoise Baleux, Nathalie Gunera-Saad, Fernando Arenzana-Seisdedos, and Françoise Bachelerie (2008) Blood 112, 34-44. CXCR4 dimerization and β-arrestin-mediated signaling account for the enhanced chemotaxis to CXCL12 in WHIM syndrome
56. Marullo S, Delavier-Klutchko C, Eshdat Y, Strosberg A D, and Emorine L, Human $b_2$-adrenergic receptors expressed in *Escherichia coli* membranes retain their pharmacological properties. Proc Natl Acad Sci USA, 1988; 85(20): 7551-5.
57. Grisshammer R, Duckworth R, and Henderson R, Expression of a rat neurotensin receptor in *Escherichia coli*. Biochem J, 1993; 295 (Pt 2): 571-6.
58. Tucker J and Grisshammer R, Purification of a rat neurotensin receptor expressed in *Escherichia coli*. Biochem J, 1996; 317 (Pt 3): 891-9.

59. Weiss H M and Grisshammer R, Purification and characterization of the human adenosine $A_{2a}$ receptor functionally expressed in *Escherichia coli*. Eur J Biochem, 2002; 269(1): 82-92.
60. Mancia F and Hendrickson W A, Expression of recombinant G-protein coupled receptors for structural biology. Mol Biosyst, 2007; 3(10): 723-34.
61. Grisshammer R and Tucker J, Quantitative evaluation of neurotensin receptor purification by immobilized metal affinity chromatography. Protein Expr Purif, 1997; 11(1): 53-60.
62. Niebauer R T, White J F, Fei Z and Grisshammer R. Characterization of Monoclonal Antibodies Directed Against the Rat Neurotensin Receptor NTS1. Journal of Receptors and Signal Transduction 2006; 26, 395-415.
63. Patenge N and Soppa J, Extensive proteolysis inhibits high-level production of eukaryal G protein-coupled receptors in the archaeon Haloferax volcanii. FEMS Microbiol Lett, 1999; 171(1): 27-35.
64. Jaakola V P, Rehn M, Moeller M, Alexiev U, Goldman A, and Turner G J, G-protein-coupled receptor domain overexpression in *Halobacterium salinarum*: long-range transmembrane interactions in heptahelical membrane proteins. Proteins, 2005; 60(3): 412-23.
65. Niu Y, Kong J, and Xu Y, A Novel GFP-Fused Eukaryotic Membrane Protein Expression System in *Lactococcus lactis* and Its Application to Overexpression of an Elongase. Curr Microbiol, 2008.
66. Roy A, Shukla A K, Haase W, and Michel H, Employing *Rhodobacter sphaeroides* to functionally express and purify human G protein-coupled receptors. Biol Chem, 2008; 389(1): 69-78.
67. Hamilton S R and Gerngross T U, Glycosylation engineering in yeast: the advent of fully humanized yeast. Curr Opin Biotechnol, 2007; 18(5): 387-92.
68. Huang L Y, Umanah G, Hauser M, Son C, Arshava B, Naider F, and Becker J M, Unnatural amino acid replacement in a yeast G protein-coupled receptor in its native environment. Biochemistry, 2008; 47(20): 5638-48.
69. Feng W, Cai J, Pierce W M, Jr., and Song Z H, Expression of CB2 cannabinoid receptor in *Pichia pastoris*, Protein Expr Purif, 2002; 26(3): 496-505.
70. Sander P, Grunewald S, Reilander H, and Michel H, Expression of the human D2S dopamine receptor in the yeasts *Saccharomyces cerevisiae* and *Schizosaccharomyces pombe*: a comparative study. FEBS Lett, 1994; 344(1): 41-6.
71. Cherezov V, Rosenbaum D M, Hanson M A, Rasmussen S G, Thian F S, Kobilka T S, Choi H J, Kuhn P, Weis W I, Kobilka B K, and Stevens R C, High-resolution crystal structure of an engineered human $b_2$-adrenergic G protein-coupled receptor. Science, 2007; 318(5854): 1258-65.
72. Rasmussen S G, Choi H J, Rosenbaum D M, Kobilka T S, Thian F S, Edwards P C, Burghammer M, Ratnala V R, Sanishvili R, Fischetti R F, Schertler G F, Weis W I, and Kobilka B K, Crystal structure of the human $b_2$ adrenergic G-protein-coupled receptor. Nature, 2007; 450(7168): 383-7.
73. Jaakola V P, Griffith M T, Hanson M A, Cherezov V, Chien E Y, Lane J R, Ijzerman A P, and Stevens R C, The 2.6 angstrom crystal structure of a human $A_{2A}$ adenosine receptor bound to an antagonist. Science, 2008; 322(5905): 1211-7.
74. Warne T, Serrano-Vega M J, Baker J G, Moukhametzianov R, Edwards P C, Henderson R, Leslie A G, Tate C G, and Schertler G F, Structure of a $b_1$-adrenergic G-protein-coupled receptor. Nature, 2008.
75. Harrison R L and Jarvis D L, Protein N-glycosylation in the baculovirus-insect cell expression system and engineering of insect cells to produce "mammalianized" recombinant glycoproteins. Adv Virus Res, 2006; 68: 159-91.
76. Marheineke K, Grunewald S, Christie W, and Reilander H, Lipid composition of *Spodoptera frugiperda* (Sf9) and *Trichoplusia ni* (Tn) insect cells used for baculovirus infection. FEBS Lett, 1998; 441(1): 49-52.
77. Gimpl G, Klein U, Reilander H, and Fahrenholz F, Expression of the human oxytocin receptor in baculovirus-infected insect cells: high-affinity binding is induced by a cholesterol-cyclodextrin complex. Biochemistry, 1995; 34(42): 13794-801.
78. Ames R S, Formwald J A, Nuthulaganti P, Trill J Jg, Foley J J, Buckley P T, Kost T A, Wu Z N, and Romanos M A, BacMam recombinant Baculoviruses in G protein-coupled receptor drug discovery. Receptors & Channels, 2004; 10(3-4): 99-107.
79. Lundstrom K, Wagner R, Reinhart C, Desmyter A, Cherouati N, Magnin T, Zeder-Lutz G, Courtot M, Prual C, Andre N, Hassaine G, Michel H, Cambillau C, and Pattus F, Structural genomics on membrane proteins: comparison of more than 100 GPCRs in 3 expression systems. J Struct Funct Genomics, 2006; 7(2): 77-91.
80. Reeves P J, Kim J M, and Khorana H G, Structure and function in rhodopsin: A tetracycline-inducible system in stable mammalian cell lines for high-level expression of opsin mutants. Proceedings of the National Academy of Sciences of the United States of America, 2002; 99(21): 13413-13418.
81. Klammt C, Schwarz D, Lohr F, Schneider B, Dotsch V, and Bernhard F, Cell-free expression as an emerging technique for the large scale production of integral membrane protein. FEBS J, 2006; 273(18): 4141-53.
82. Straub R E, Frech G C, Joho R H, and Gershengorn M C, Expression cloning of a cDNA encoding the mouse pituitary thyrotropin-releasing hormone receptor. Proc Natl Acad Sci USA, 1990; 87(24): 9514-8.
83. Eroglu C, Cronet P, Panneels V, Beaufils P, and Sinning I, Functional reconstitution of purified metabotropic glutamate receptor expressed in the fly eye. EMBO Rep, 2002; 3(5): 491-6.
84. Tateno M, Toyooka M, Shikano Y, Takeda S, Kuwabara N, Sezutsu H, and Tamura T, Production and Characterization of the Recombinant Human μ-Opioid Receptor from Transgenic Silkworms. J Biochem, 2009; 145(1): 37-42.
85. Mayfield S P, Manuell A L, Chen S, Wu J, Tran M, Siefker D, Muto M and Marin-Navarro J. *Chlamydomonas reinhardtii* chloroplasts as protein factories. Current Opinion in Biotechnology, 2007, 18:1-8
86, Dance A. From pond scum to pharmacy shelf. Nature Medicine, 2010, 16, 146-149
87. Rosenbaum D M, Cherezov V, Hanson M A, Rasmussen S G, Thian F S, Kobilka T S, Choi H J, Yao X J, Weis W I, Stevens R C, and Kobilka B K, GPCR engineering yields high-resolution structural insights into $b_2$-adrenergic receptor function. Science, 2007; 318(5854): 1266-73.
88. Andre C, De Backer J P, Guillet J C, Vanderheyden P, Vauquelin G, and Strosberg A D, Purification of muscarinic acetylcholine receptors by affinity chromatography. EMBO J, 1983; 2(4): 499-504.
89. Fuller D H, Shipley T, Allen T M, Fuller J T, Wu M S, Horton H, Wilson N, Widera G, Watkins D I. (2007) Immunogenicity of hybrid DNA vaccines expressing hepatitis B core particles carrying human and simian immunodeficiency virus epitopes in mice and rhesus macaques. Virology 364: 245-255
90. Yager E J, Dean H J, Fuller D H. (2009) Prospects for developing an effective particle-mediated DNA vaccine against influenza. Expert Rev Vaccines 8: 1205-1220
91. Roberts L K, Barr L J, Fuller D H, McMahon C W, Leese P T, Jones S. (2005) Clinical safety and efficacy of a powdered Hepatitis B nucleic acid vaccine delivered to the epidermis by a commercial prototype device. Vaccine 23: 4867-4878
92. Loudon P T, Yager E J, Lynch D T, Narendran A, Stagnar C, Franchini A M, Fuller J T, White P A, Nyuandi J, Wiley C A, Murphey-Corb M, Fuller D H. (2010) GM-CSF Increases Mucosal and Systemic Immunogenicity of an H1N1 Influenza DNA Vaccine Administered into the Epidermis of Non-Human Primates. PLoS ONE 5(6): e11021
93. Surman D R, Irvine K R, Shulman E P, Allweis T M, Rosenberg S A, Restifo N P (1998) Generation of polyclonal rabbit antisera to mouse melanoma associated antigens using gene gun immunization. J. Immunol. Methods. 214: 51-62.
94. Smulski C, Labovsky V, Levy G, Hontebeyrie M, Hoebeke J and Levin M J. FASEB J 2006 20: 1396-1406
95. Herse F, Verlohren S, Wenzel K, Pape J, Muller D N, Modrow S, Wallukat G, Luft F C, Redman C W and Dechend R. Hypertension. 2009 53: 393-8.
96. Prabhakar B S, Bahn R S and Smith T J. Endocrine Reviews 2003 24: 802-835.
97. Di Paola et al, 1997-Di Paola R, Menzaghi C, De Filippis V, Corda D and Di Cerbo A. J Clin Endocrinol Metab. 1997 82: 670-3.
98. Douglas R S, Afifiyan N F, Hwang C J, Chong K, Haider U, Richards P, Gianoukakis A G and Smith T J. J Clin Endocrinol Metab. 2010 95: 430-8.
99. Jahns R, Boivin V, Hein L, Triebel S, Angermann C E, Ertl G and Lohse M J. J Clin Invest. 2004 113: 1419-29.
100. Zhou C C, Irani R A, Zhang Y, et al, 2010). Zhou C C, Irani R A, Zhang Y, Blackwell S C, Mi T, Wen J, Shelat H, Geng Y J, Ramin S M, Kellems R E and Xia Y. Circulation. 2010 121: 436-44.
101. Kemp E H, Gavalas N G, Krohn K J, Brown E M, Watson P F and Weetman A P. J Clin Endocrinol Metab. 2009 94: 4749-56.
102. Makita N, Sato J, Manaka K, Shoji Y, Oishi A, Hashimoto M, Fujita T and Iiri T. Proc Natl Acad Sci USA. 2007 104: 5443-5448.
103. Pallais J C, Kifor O, Chen Y B, Slovik D and Brown E M. N Engl J. Med. 2004 351: 362-9.
104. Kifor O, McElduff A, LeBoff M S, Moore F D Jr, Butters R, Gao P, Cantor T L, Kifor 1 and Brown E M. J Clin Endocrinol Metab. 2004 89: 548-56.
105. Koo N Y, Li J, Hwang S M, Choi S Y, Lee S J, Oh S B, Kim J S, Lee E B, Song Y W and Park K. Rheumatology (Oxford). 2008 47: 828-33.
106. Negroni M P, Fiszman G L, Azar M E, Morgado C C, Espanol A J, Pelegrina L T, de la Torre E and Sales M E. J Clin Immunology. 2010 30: 474-484.
107. Wenzel K, Haase H, Wallukat G, Derer W, Bartel S, Homuth V, Herse F, Hubner N, Schulz H, Janczikowski M, Lindschau C, Schroeder C, Verlohren S, Morano I, Muller D N, Luft F C, Dietz R, Dechend R and Karczewski P. PLoS One 2008 3:e3742
108. Sheng J R, Grimme S, Bhattacharya P, Stowell M H B, Artinger M, Prabhakar B S and Meriggioli M N. Exp Neurology. 2010, 225: 320-7
109. Botha C J and Penrith M-L. J I S Afri. Vet Ass. 2009 80: 63-74.
110. Potter L. T Life Sciences. 2001 68: 2541-2547.
111. Rajagopalan N, Pung Y F, Zhu Y Z, Wong P T H, Kumar P P and Kini R M. FASEB J. 2007 21: 3685-3695
112. Huang L-F, Zheng J-B, Xu Y, Song H-T and Yu C-X. Toxicon. 2008 51: 1008-1016.
113. Fruchart-Gaillard C, Mourier G, Marquer C, Menez A and Servent D. Mol. Pharmacol. 2006 69: 1641-1651.
114. Koivula K, Rondinelli S and Näsman J. Toxicon. 2010 56: 440-447.
115. Cuevas and Adams. J. Neurophysiol. 1997 78: 1903-1912.
116. Jerusalinsky D, Kornisiuk E, Bernabeu R, Izquierdo I and Cervenansky C. Toxicon. 1995 33: 389-397.
117. Krajejewski J L, Dickerson I M and Potter L T. Mol. Pharmacol. 2001 60: 725-731.
118. Eddleston M, Senarathna L, Mohammed F, Buckley N, Juszczak E, Sheriff M H, Ariaratnam A, Rajapakse S, Warrell D and Rajakanthan K. Lancet. 2003 362: 1041-4.
119. Sinclair A J, Hewick D S, Johnston P C, Stevenson I H and Lemon M. Br J Clin Pharmacol. 1989 28: 352-356
120. S P Beltrame, S R Auger, C R Bilder, C I Waldner and Goin J C. Clin Exp Immunol 2011 164 Modulation of M(2) muscarinic receptor-receptor interaction by immunoglobulin G antibodies from Chagas' disease patients The listing or discussion of an apparently prior-published document in this specification should not necessarily be taken as an acknowledgement that the document is part of the state of the art or is common general knowledge.

The invention claimed is:

1. A pharmaceutical formulation comprising a vaccine comprising a mutant G protein-coupled receptor (GPCR) having increased stability in a particular conformation relative to its parent GPCR or a polynucleotide encoding said mutant GPCR wherein the vaccine is capable of antagonising or agonising a GPCR in vivo.

2. A formulatiom according to claim 1, further comprising an adjuvant.

3. A formulation according to claim 1, wherein the GPCR is complexed to a ligand.

4. A formulation according to claim 1, wherein the GPCR is an engineered GPCR which, when compared to the wild-type GPCR, lacks at least one epitope in a first ligand binding site and preserves at least one epitope in a second ligand binding site.

5. A formulation according to claim 1, wherein the GPCR has increased stability in the antagonist conformation, or in the agonist conformation.

6. A formulation according to claim 1 wherein the GPCR is a mammalian GPCR.

7. A formulation according to claim 6 wherein the GPCR is a human, mouse or rat GPCR.

* * * * *